US010626375B2

(12) United States Patent
Yeh

(10) Patent No.: US 10,626,375 B2
(45) Date of Patent: Apr. 21, 2020

(54) DISEASE CONTROL OF THE PLANT BACTERIAL PATHOGENS CAUSING CITRUS CANKER AND RICE BLIGHT

(71) Applicant: AUXERGEN, INC., Baltimore, MD (US)

(72) Inventor: Ting-Yu Yeh, Baltimore, MD (US)

(73) Assignee: Auxergen, Inc., Baltimore, MD (US)

(*) Notice: Subject to any disclaimer, the term of this patent is extended or adjusted under 35 U.S.C. 154(b) by 72 days.

(21) Appl. No.: 15/321,942

(22) PCT Filed: Jun. 24, 2015

(86) PCT No.: PCT/US2015/374880
§ 371 (c)(1),
(2) Date: Dec. 23, 2016

(87) PCT Pub. No.: WO2015/200519
PCT Pub. Date: Dec. 30, 2015

(65) Prior Publication Data
US 2018/0105801 A1   Apr. 19, 2018

Related U.S. Application Data

(60) Provisional application No. 62/016,972, filed on Jun. 25, 2014.

(51) Int. Cl.
*C12N 7/00* (2006.01)
*A01N 63/40* (2020.01)
*A61K 35/76* (2015.01)
*C12N 15/86* (2006.01)

(52) U.S. Cl.
CPC .............. *C12N 7/00* (2013.01); *A01N 63/40* (2020.01); *A61K 35/76* (2013.01); *C12N 15/86* (2013.01); *C12N 2795/14143* (2013.01); *C12N 2795/14162* (2013.01)

(58) Field of Classification Search
None
See application file for complete search history.

(56) References Cited

U.S. PATENT DOCUMENTS

| 3,052,606 | A | 9/1962 | Gierer |
| 2007/0292395 | A1 | 12/2007 | Jackson |
| 2009/0234101 | A1 | 9/2009 | Ladner |
| 2010/0068185 | A1 | 3/2010 | Reber |
| 2011/0143997 | A1 | 6/2011 | Henry |
| 2013/0122549 | A1 | 5/2013 | Lu |

FOREIGN PATENT DOCUMENTS

WO   WO2006050193 A2   5/2006

OTHER PUBLICATIONS

Jalap et al., GenEmbl Database, Acc. No. CP003778, Genome Announc 1 (3), E00235-13 (2013).*
Jalap et al., Genome Announcements, May/Jun. 2013, vol. 1, Issue 3, pp. 1-2.*

Casadevall A, Day LA. DNA packing in the filamentous viruses fd, Xf, Pf1 and Pf3. Nucleic Acids Res. Apr. 10, 1982;10(7):2467-81.
Chen FC, Koopmans G, Wiseman RL, Day LA, Swinney HL. Dimensions of Xf virus from its rotational and translational diffusion coefficients. Biochemistry. Apr. 1, 1980;19(7):1373-6.
Cheng CM, Wang HJ, Bau HJ, Kuo TT. The primary immunity determinant in modulating the lysogenic immunity of the filamentous bacteriophage cf. J Mol Biol. Apr. 16, 1999;287(5):867-76.
Dai H, Chow TY, Liao HJ, Chen ZY, Chiang KS. Nucleotide sequences involved in the neolysogenic insertion of filamentous phage Cf16-v1 into the Xanthomonas campestris pv. citri chromosome. Virology. Dec. 1988;167(2):613-20.
Dai H, Tsay SH, Kuo TT, Lin YH, Wu WC. Neolysogenization of Xanthomonas campestris pv. citri infected with filamentous phage Cf16. Virology. Feb. 1987;156(2):313-20.
Exconde, O.R. Yield losses due to bacterial leaf blight of rice. Philippines Agriculture 1973; 57, 128-140.
Feng TY, Tu J, Kuo TT. Characterization of deoxycytidylate methyltransferase in Xanthomonas oryzae infected with bacteriophage Xp12. Eur J Biochem. Jun. 1, 1978;87(1):29-36.
Frangione B, Nakashima Y, Konigsberg W, Wiseman RL. The amino acid sequence of the major coat protein subunit of the filamentous virus Xf. FEBS Lett. Dec. 15, 1978;96(2):381-4.
Gottwald, T.R. 2000. Citrus canker. The Plant Health Instructor. DOI: 10.1094/PHI-I-2000-1002-01. Updated 2005.
Kuo TT, Chao YS, Lin YH, Lin BY, Liu LF, Feng TY. Integration of the DNA of filamentous bacteriophage Cflt into the chromosomal DNA of its host. J Virol. Jan. 1987;61(1):60-5.
Kuo TT, Chiang CC, Chen SY, Lin JH, Kuo JL. A long lytic cycle in filamentous phage Cf1tv infecting Xanthomonas campestris pv. citri. Arch Virol. 1994;135(3-4):253-64.
Kuo TT, Huang TC, Chow TY. A filamentous bacteriophage from Xanthomonas oryzae. Virology. Nov. 1969;39(3):548-55.
Kuo TT, Huang TC, Teng MH. 5-Methylcytosine replacing cytosine in the deoxyribonucleic acid of a bacteriophage for Xanthomonas oryzae. J Mol Biol. Jul. 14, 1968;34(2):373-5.
Kuo TT, Lin YH, Huang CM, Chang SF, Dai H, Feng TY. The lysogenic cycle of the filamentous phage Cflt from Xanthomonas campestris pv. citri. Virology. Feb. 1987;156(2):305-12.
Kuo TT, Lin YT. Xf phage invading the host cells with their protein coats. J Gen Virol. Aug. 1976;32(2):241-7.
Kuo TT, Tan MS, Su MT, Yang MK. Complete nucleotide sequence of filamentous phage Cf1c from Xanthomonas campestris pv. citri. Nucleic Acids Res. May 11, 1991;19(9):2498.

(Continued)

*Primary Examiner* — Phuong T Bui
(74) *Attorney, Agent, or Firm* — Miles & Stockbridge P.C.; David R. Schaffer

(57) ABSTRACT

The present invention describes applications and methods (1) to use bacterophage Cf and its variants to prevent and treat the citrus canker pathogen, *Xanthomonas citri* subsp. *citri*; (2) to engineer recombinant Cf phages that the infectivity is controllable without being harmful to the rest of environment; (3) to engineer and produce recombinant Cf phages with longer storage shelf life; (4) to use Cf phage as a vector for the introduction and insertion of foreign genetic material into *Xanthomonas citri* subsp. *citri*. genome; (5) to use and engineer Xp12 and Xf bacteriophages to inhibit *Xanthomonas oryzae* pv. *oryzae*, the causal agent of the rice blight disease.

5 Claims, 19 Drawing Sheets

Specification includes a Sequence Listing.

(56) References Cited

OTHER PUBLICATIONS

Kuo TT, Tu J. Enzymatic synthesis of deoxy-5-methyl-cytidylic acid replacing deoxycytidylic acid in Xanthomonas pryzae phage Xp12DNA. Nature. Oct. 14, 1976;263(5578):615.

Mao, R, Zheng J, Zhang R. Side effects of copper fungicides on Amblyseius cucumeris by laboratory bioassays. Bulletin of Insectology. 2011, 64 (1):69-72.

Marzec CJ, Day LA. DNA and protein lattice-lattice interactions in the filamentous bacteriophages. Biophys J. May 1983;42(2):171-80.

Marzec CJ, Day LA. A theory of the symmetries of filamentous bacteriophages. Biophys J. Mar. 1988;53(3):425-40.

Marzec CJ, Day LA. An electrostatic spatial resonance model for coaxial helical structures with applications to the filamentous bacteriophages. Biophys J. Dec. 1994;67(6):2205-22.

Mather MW, McReynolds LM, Yu CA. An enhanced broad-host-range vector for gram-negative bacteria: avoiding tetracycline phototoxicity during the growth of photosynthetic bacteria. Gene. Apr. 14, 1995;156(1):85-8.

Nelson M. and McClelland M. Effect of site-specific methylation on DNA modification methyltransferases and restriction endonucleases. Nucleic Acids Res. 1991; 19: 2045-71.

Niño-Liu, DO, Roland PC, Bogdanove, AJ. Xanthomonas oryzae pathovars: model pathogens of a model crop. Mol Plant Pathol 2006, 7(5): 303-324.

Oshiro EE, Nepomuceno RS, Faria JB, Ferreira LC, Ferreira RC. Site-directed gene replacement of the phytopathogen Xanthomonas axonopodis pv. citri. J Microbiol Methods. Apr. 2006;65(1):171-9.

Sega, GA. A review of the genetic effects of ethyl methanesulfonate. Mutat Res. Sep.-Nov. 1984;134(2-3):113-42.

Shieh GJ, Lin CH, Kuo JL, Kuo TT. Characterization of an open reading frame involved in site-specific integration of filamentous phage Cf1t from Xanthomonas campestris pv. citri. Gene. May 26, 1995;158(1):73-6.

Thomas GJ Jr, Day LA. Conformational transitions in Pf3 and their implications for the structure and assembly of filamentous bacterial viruses. Proc Natl Acad Sci U S A. May 1981;78(5):2962-6.

Thomas GJ Jr, Prescott B, Day LA. Structure similarity, difference and variability in the filamentous viruses fd, Ift IKe, Pf1 and Xf. Investigation by laser Raman spectroscopy. J Mol Biol. Apr. 5, 1983;165(2):321-56.

Thomas GJ Jr, Prescott B, Opella SJ, Day LA. Sugar pucker and phosphodiester conformations in viral genomes of filamentous bacteriophages: fd, If1, IKe, Pf1, Xf, and Pf3. Biochemistry. Jun. 14, 1988;27(12):4350-7.

Tseng YH, Lo MC, Lin KC, Pan CC, Chang RY. Characterization of filamentous bacteriophage ☐Lf from Xanthomonas campestris pv. campestris. J Gen Virol. Aug. 1990;71 (8):1881-4.

Van Brunt J. Amplifying genes: PCR and its alternatives. Biotechnology (NY). Apr. 1990;8(4):291-4.

Wang HJ, Cheng CM, Wang CN, Kuo TT. Transcription of the genome of the filamentous bacteriophage cf from both plus and minus DNA strands. Virology. Apr. 10, 1999;256(2):228-32.

Wang RY, Ehrlich M. 5-methyl-dCTP deaminase induced by bacteriophage XP-12. J Virol. Apr. 1982;42(1):42-8.

Wen FS, Tseng YH. Nucleotide sequence determination, characterization and purification of the single-stranded DNA-binding protein and major coat protein of filamentous phage ☐Lf of Xanthomonas campestris pv. campestris. J Gen Virol. Jan. 1994;75 (1):15-22.

Wiseman RL, Day LA. Different packaging of DNA in the filamentous viruses Pf1 and Xf. J Mol Biol. Nov. 5, 1977;116(3):607-11.

Yang MK, Kuo TT. A physical map of the filamentous bacteriophage Cf genome. J Gen Virol. Jul. 1984;65 (7):1173-81.

Yang, MK, Su, WC, Kuo TT. High efficient transfection of Xanthomonas campestris by electroporation. 1991; Bot Bull. Academia Sinica 32: 197-203.

Yang MK, Yang YC. The A protein of the filamentous bacteriophage Cf of Xanthomonas campestris pv. citri. J Bacteriol. May 1997;179(9):2840-4.

Dai H, Chiang KS. Kuo, TT. Characterization of a New Filamentous Phage Cf from Xanthomonas citri. J. Gen. Virol. 1980, 46, 277-89.

Yang, MK, huang, HM, Yang, YC, Su, WC. Molecular cloning and expression of the coat protein genes of Cf, a filamentous bacteriophage of Xanthomonas campestris pv. citri. Bot. Bull. Acad. Sin. (1995) 36: 207-214.

Kuo TT, Chow TY, Lin YT. A new thymidylate biosynthesis in Xanthomonas oryzae infected by phage Xp12. Virology. Apr. 30, 1982;118(2):293-300.

International Search Report dated Nov. 12, 2015 for International Application No. PCT/US2015/037488.

Written Opinion of the International Search Authority dated Dec. 11, 2015 for International Application No. PCT/US2015/037488.

Ahmad, A. A., Askora, A., Kawasaki, T., Fujie, M., & Yamada, T. The filamentous phage XacF1 causes loss of virulence in Xanthomonas axonpodis pv. citri, the causative agent of citrus canker disease. Frontiers in Microbiology. Jul. 1, 2014; 5:321.

Ehrlich, M., Lin, F. H., Ehrlich, K., Brown, S. L., & Mayo, J. A. Changes in macromolecular synthesis in Xanthomonas pryzae infected with bacteriophage XP-12. Journal of Virology. Sep. 1977;23(3):517-523.

Lin JY, Wu CC, Kue TT. Amino acid analysis of the coat protein of the filamentous bacterial virus xf from Xanthomona pryzae. Virology. Jul. 1971;45(1):38-41.

\* cited by examiner

```
                                    5'--------
TGACGACGAA   TTGCAGAGCT   ATGCGCTATG   GCACATCTGG   ATGGCGGCGA
-239                                                      -190
                                                       5'-
ATGGATGGCG   AAAATTCAGG   CCGAAGCAGC   GGCATCGCCG   GCTGAAAAAG
-189                                                      -140
─────────
CGCTATGGCG   ATCAGTGTTG   GACAGGCTAA   GCGCGGCCGC   CGCGGTGGTC
-139                                                       -90
GCGCTGCTGG   TCCTGGCGGT   ACACACAGGG   GCGCATGAGC   CGGTGCTAGC
-89                                                        -40
                                    ═           ═══════>    <═══════
GGCCCTCTCG   CCGGTAGCCC   TTACCCACCC   TCTATACATT  ATGCGAAGTG
-39                                              0          +10
TGCTGTTGAC   GCTGCTGTGC   GCCCTGGCGG   CCTATCACTG   CTGCTCCCTC
+11                                                        +60
CACAGGAAGC   GGACTGGACA   ATGACGCTAG   ACACGTACGA   TCGCGTAGAC
+61                                                       +110
CTGACGGCCC   TTGGGCCGGT   TTTGGTTTTC   ACCGGCACCG   CTTCTTCACC
+111                                            ─────── -3'  +160
CCGGAGAATT   ACGACATCGA   ACCGTGCGAT   ATGCGGTATT   CGGCGCTGAC
+161                                                      +210
ATGCGCGATC   GCACGCGAAT   GGTCACTGTT   GATGTCAGAA   GAACGCAATG
+211                                                      +260
```

FIG. 2B

```
CATGCAAGCT   TACTCAACGG   CGCCCCGTC    CGCGTGGACT   CGGGCTCGGT
-139                                                       -90
 -3'
ATTGACCATC   GCTGGCTGAG   GCGGGCGGCG   CGGTGCAGCC   GCAAGTGAAA
-89                                                        -40
                                     ═          ═══════>    <═══════
TCAAAGAGAA   GCACGAACAA   TATTTGACAT   AATATACATT  ATGCGAAATT
-39                                              0          +10
GGCCGCGTCC   CCGTACGGGC   CGGCGCCATG   TGCACTGCAG   CTCGAGCACC
+11                                                        +60
AGGCAGAACA   GTTCCGCACC   GCCAGGCTGA   TGCAGTCCCT   GACGTCAGGC
+61                                                       +110
```

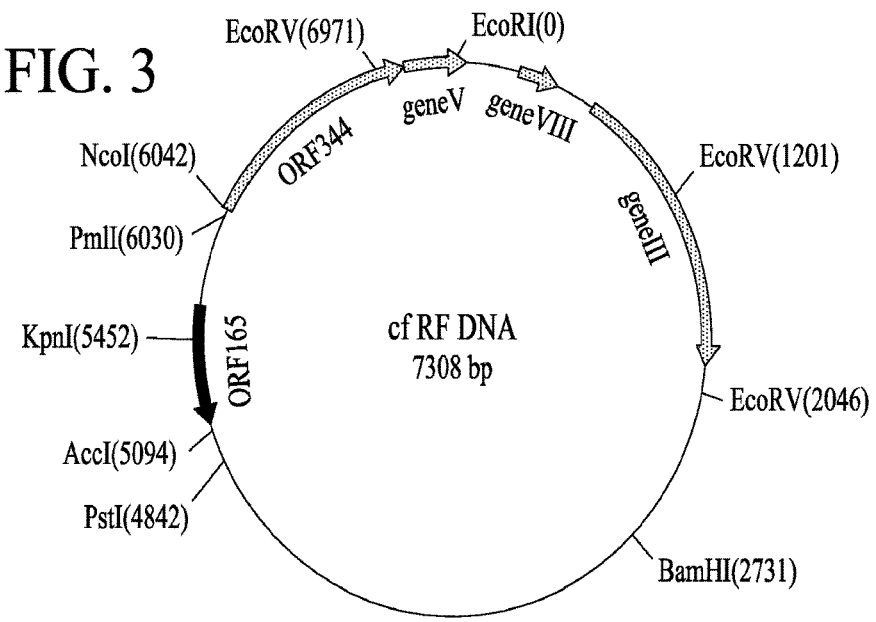

```
              NcoI            PmlI
gccacgatagaactccatggcccatggcagcgttacgtgcatcagcagcatcggtgcgcgatgcaaa
atagctctgttcaacagcgttgccgttgacgacgatggtcaagacgtaaatgcggggggccgccctgc
actcgagctggcgcaatcatccatgcaacagatcgagactcagccacgacgcacctcgagatatgag
atagcgaccaatgaggcttgatcaatttgagcaaccatcgcgtcgtgcttgagatcaagacaccaac
agatcacagcgacgattgcgtacccggtgagcacgcagatcgacacgagaatgtgcagcgccaaaag
ctggcccaggaccgaatatggatgcacggtgtagccccctcccctgccccttgacgcggaccccgga
                                             cf-tv1      A
gggggagccgggggtgcgcggtgcttagggttgcctaagcacgggagcATGTATAGTTTTCACTGTCC
         ———————————— 49-bp deletion in cf-tv2 ———————— M  Y  S  F  H  C  P
TCTCTGTCAAGAAAAACCTGTCATGGACCATGTAAATAATTTGCTTGACACCGTGCGCAAGTCGTGC
 L  C  Q  E  K  P  V  M  D  H  V  N  N  L  L  D  T  V  R  K  S  C
GCCATACCGTCAGACAACATGTTGAGCAAAAAAATTGGAGTGACGCGGGCGCTGATAAGCGGCTGGC
 A  I  P  S  D  N  M  L  S  K  K  I  G  V  T  R  A  L  I  S  G  W  R
        KpnI
GCGTTGGCCGGTACCCGTGGCCTGACGCACGAATTGCAGAGCTATGCGCTATGCCACATCTGGATGG
   V  G  R  Y  P  V  P  D  A  R  T  A  E  L  Y  A  M  A  M  L  D  G
CGGCGAATGGATGGCGAAAATTCACGCCGAAGCAGCGGCATCGCCGGCTGAAAAAGCGCTATGGCGA
  G  E  W  M  A  K  I  M  A  E  A  A  A  S  P  A  E  K  A  L  W  R
TCAGTGTTGGACAGGCTAAGCGCGGCCGCCGCGGTGGTCGCGCTGCTGGTCCTGGCGGTACACACAG
  S  V  L  D  R  L  S  A  A  A  A  V  V  A  L  L  V  L  A  V  R  T  G
                                                              AccI
GGGCGCATGAGGCGCTGCTAGCGGCCCTCTCGCCGGTAGCCGTTACCCACCCTCTATACATTATGCG
   A  E  E  A  L  L  A  A  L  S  P  V  A  V  T  H  P  L  Y  T  M  R
AACTGTGCTGTTGACGCTGCTGTGCGCCCTGGCGGCCTATCACTGCTGGTCCCTCCACAGGAAGCGC
   S  V  L  L  T  L  L  C  A  L  A  A  Y  R  C  W  S  L  H  R  K  R
ACTGGACAATGAcgctagacacctacgatcgcgtagacctgaccggcccttgggccggttttggttt
 T  G  Q  -
tcaggggcaccggttcttcaccccggagaattacgacatcgaaccgtgcgatatgcggtattgggcg
ctgacatgcgcgatcgcacgggaatggtcactgttgatgtcagaagaacgcaatgcgcgatcggcga
atcctcgaaagcctactgccacaagatctccagggtctcgtttgtctcgaggcgcagacgtgatcta
           pstI
tctgcgggacgtgctgctgca
```

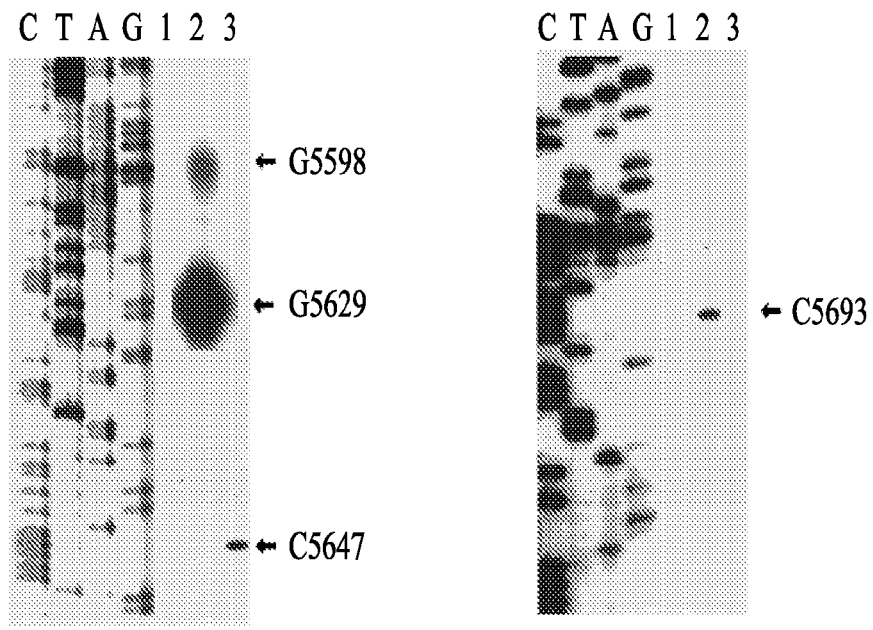

FIG. 5A gtacc aggta ctgtc caaaa agaac tgtct ctcct gtcac ttttg ata
catgg tccat gacag gtttt tcttg acaga gagga cagtG aaaac tat
                         -35                          -10
                                                cM1(G5598)

ORF 165
  ↓                    49-bp deletion in cf-tv2
tgtac gaggg cacga atccg ttggg attcg tggcg cgtgg gggcc gagg
acatg ctccc Gtgct taggc aaccc taagc accgc gcacc cccgg ctcc
        cM1(G5629)

cM2(5693)
gga ggccc caggc gcagt tcccc gtcCc ctccc ccgat gtggc acgt
cct ccggg gtccg cgtca agggg caggg gaggg ggcta caccg tgca

Cf2
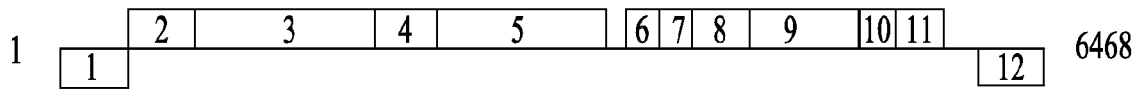
phiLf
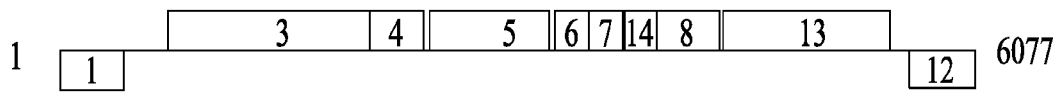
1. Cf1cp7-like protein
2. Chloride channel EriC
3. Zot protein, gI
4. Minor coat protein, gVI
5. Minor coat protein A
6. Major coat protein B
7. Minor coat protein, gIX
8. ssDNA-binding protein
9. Replication protein RstA
10. Hypothetical protein
11. Hypothetical protein
12. Cf1c 18.2 kDa protein
13. Replication intiation protein
14. Minor coat protein, gVII
FIG. 13A

FIG. 13B

Major Coat protein B

```
                                                             Identity    Expect
                                                               76%       3e-13
Cf2      1  MGDILSGLSAADAVTAVGAAALTALVGFTKWGAKKVAGFFG   42
            MGDIL+G+S A+A  TA++ AAA+IALVGFTKWGAKKVA FFG
phiLf    1  MGDILTGVSGAEAATAMIAAAAITALVGFTKWGAKKVASFFG   42
```

Minor Coat protein A

```
                                                             28%        2e-16
Cf2      3    VILSALCTLVIALCAISPAHAADSFSQAFAKCMNDASAYQVKDTNLITSPGTCVDKVTEA  62
              V+++A  L++ LC+ S AHAA   + +A++ CM  AS  K+ ++  +P    +
Cf1c    30    VVVAACFGLLLQLCSGS-AHAAVDQGEAYSLCMKFASDMVAKNPDMRRMPSCRSRRAFQ-  87

Cf2     63    TGKYYQCQYSAAAYY-QGPVSVVTCGDYPYDNENNC--KNAPPLTNVSVRGSIYA----C  115
                Y CQY A  Y       SV TCGDY YD++  C  +E+ L  +     Y      C
Cf1c    88    ----YTCQYEAIPYVGKSQWSVDTCGDYSYDDQYTCASRNSNKLADAA---PWYTPPPNC  140

Cf2    116    SWQCQYTMNSAGGVDVCMGGGADLYCAAKNWSPTGQEC-----------QQGDAVPS    161
              + CQ     S   G + GG  Y  K+ +  G  C                ++ DA
Cf1c   141    ISGCQVQGTSFSGDN-----GGVKTY-GMKDRTYNGSICTPTKPTNDIGELQEEKNDATKE 195

Cf2    162    GIHEPDKQTCSSTGGAYAECTREDGTHCVTGAAGSTLCWKPELTGPRQTA  211
              E       C++ +G    C++  +C T ++G T CWKP  TG + A
Cf1c   196    KAPE----CTALGSGQTACLKPNGDYCATASSGKTFCWKPAETGKKTDA  240
```

```
                                                             73%        2e-36
Cf2    303    SPTGDLYTKSDKTVESVVSRFATQVRATPLAGGIASFMTVPSGGSCFVFSLGASKWWDAM  362
              +P+ +LY  KS KTVESV+S+F TQVR TP+  GI  FM VPSGGSCPVFSLGASKWWDAM
phiLf  292    APMSELYKKSGKTVESVLSKFNTQVRGTPMVAGIGDFMKVPSGGSCPVFSLGASKWWDAM  351

Cf2    363    MIDFHCSGTFLTFLRACGWV  382
              I+FHC G FL FLRA GWV
phiLf  352    TINFHCGGDFLAFLRAAGWV  371
```

```
         GTA GCC GTT ACC CAC CCT CTA TAC ATT ATG CGA AGT
Cf1c
     131  V   A   V   T   H   P   L   Y   I   M   R   S  142

GTA GCC GTT ACC CAC CCT CTA TAC ATT ATG CGA AGT
XacF1
     117  V   A   V   T   H   P   L   Y   I   M   R   S  128

GAG TCG AGT GCG TAT AGT CTG TAT ATT ATG TCA AAT
Cf2*
     119  E   S   S   A   Y   S   L   Y   I   M   S   N  130

CTC GCC CTA ACG GCA CCT TCT ATA CAT TAT GCG AAA
phiLf
     140  L   A   L   T   A   P   S   I   H   Y   A   K  151

CTC GCC ATA ACG CCA ACC GTC TAT ACA TTA TGC GAA
Xf
     134  L   A   I   T   P   T   V   Y   T   L   C   E  145
```

\*Core integration sequence is not TATACATTATGCGAA

FIG. 14

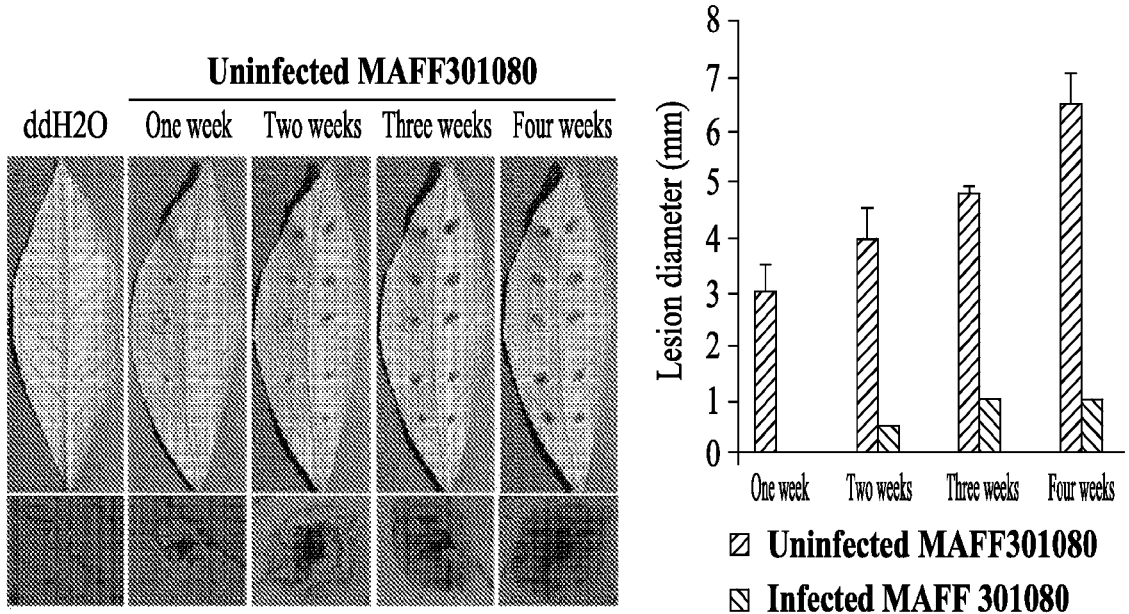
FIG. 17B
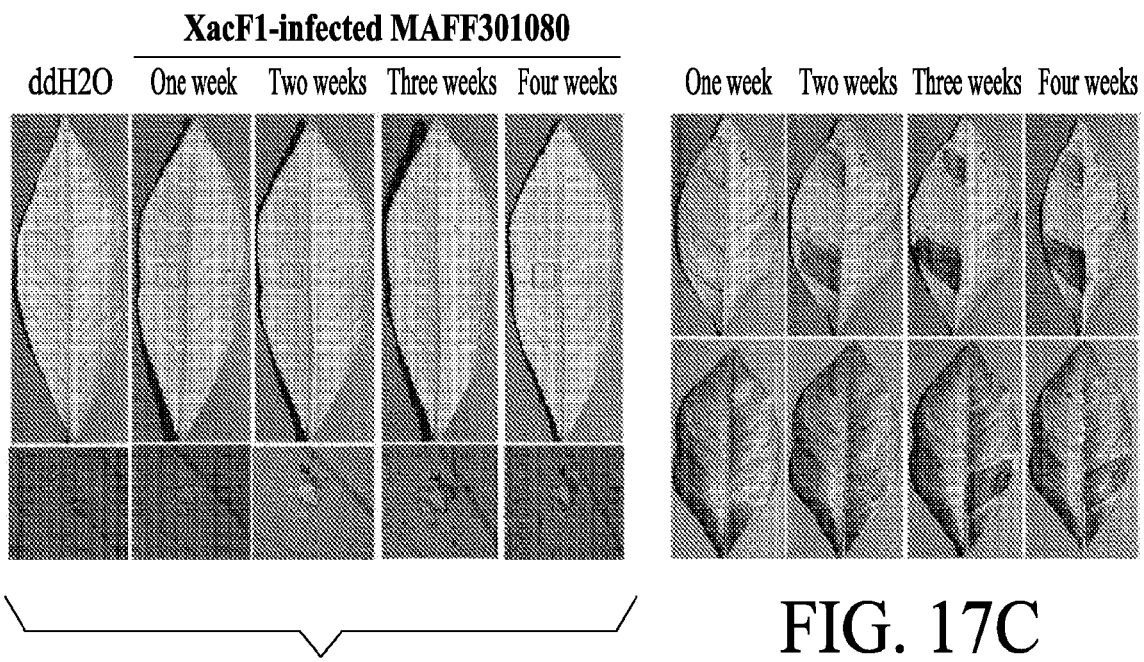
FIG. 17C
FIG. 17A

US 10,626,375 B2

DISEASE CONTROL OF THE PLANT BACTERIAL PATHOGENS CAUSING CITRUS CANKER AND RICE BLIGHT

CROSS REFERENCE TO RELATED APPLICATIONS

This application claims priority to U.S. Provisional Application No. 62/016,972 filed, Jun. 25, 2014, the contents of which are incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 19, 2018, is named T9215-20856US01_Sequence listing_ST25.txt and is 136 kb in size.

FIELD

The disclosure provides novel genes that encode pesticidal proteins. These proteins and the nucleic acid sequences that encode them are useful in controlling and treating plant bacterial pathogens associated with plant diseases, such as citrus canker and rice blight.

BACKGROUND

*Xanthomonas* is a genus of Proteobacteria, many of which cause plant diseases that leads to major economic loss. This application describes novel methods using native or genetic engineered bacteriophages to inhibit *Xanthomonas* infection in the field.

Citrus canker is caused by a bacterial pathogen, *Xanthomonas citri* subsp. *citri* (formly *X. axonopodis* pv. *citri*, or *X. campestris* pv. *citri*), and is one of the most devastating diseases on citrus plants. Infection causes lesions on the leaves, stems, and fruit of citrus trees, including lime, oranges, and grapefruit. Canker significantly affects the vitality of citrus trees, causing leaves and fruit to drop prematurely. A fruit infected with canker is generally too unsightly to be sold.

Citrus canker disease was first recorded in South East Asia in 1827, and it is extremely persistent when it becomes established in an area. Citrus groves have been destroyed in attempts to eradicate the disease. Some areas of the world have eradicated citrus canker and others have ongoing eradication programs, but the disease remains endemic in most areas where it has appeared. Because of its rapid spread, high potential for damage, and impact on export sales and domestic trade, citrus canker is a significant threat to all citrus-growing regions. Many countries like the United States and Brazil are currently suffering from canker outbreaks. The first introduction of citrus canker in Florida was in 1910 on trifoliate rootstock seedlings imported from Japan. The disease spread around the Gulf Coast from Texas to Florida and further north to South Carolina. Citrus canker has been a serious problem in Florida since the last outbreak which began in 1995. This disease is now also present in Japan, South and Central Africa, the Middle East, Bangladesh, the Pacific Islands, some countries in South America. In Florida alone, costs of running eradication program from 1995 through 2005 plus compensation to commercial growers and homeowners for residential citrus destroyed is approaching $1 billion dollars. Under the current citrus canker quarantine instituted by USDA/APHIS at the end of 2013, the interstate movement of citrus plants and plant parts other than fruit remains prohibited in the US. (Gottwald, 2000).

Copper-based products have been to be an effective means of controlling citrus canker. However, copper has been shown to stimulate the growth of mite populations in citrus tree (Mao et. al. 2011). Additionally, copper buildup on the citrus groves and copper-resistant pathogens are also potential problems. Developing a new science-based approach for managing and eradicating citrus canker in the field is emergent and critical.

Bacteriophage (or called "phage" in this application interchangeably) is a naturally occurring virus that that infects and replicates within bacteria. The replication of a bacteriophage may have a "lytic cycle" or a "lysogenic cycle", and a few viruses are capable of carrying out both. With lytic phages, bacterial cells are broken open (lysed) and destroyed after immediate replication of the phage. As soon as the cell is destroyed, the phage progeny can find new hosts to infect. Lytic phages have been used for over 90 years as an alternative to antibiotics in the former Soviet Union and Central Europe, as well as in France. They are seen as a possible therapy against multi-drug-resistant strains of many bacteria. In contrast, the lysogenic cycle does not result in immediate lysing of the host cell. Lysogenic viral genome will integrate with host DNA and replicate along with it fairly harmlessly, or may even become established as a plasmid. The virus remains dormant until host conditions deteriorate, then the endogenous phages (known as "prophages") become active. At this point they initiate the reproductive cycle, resulting in lysis of the host cell. As the lysogenic cycle allows the host cell to continue to survive and reproduce, the virus is reproduced in all of the cell's offspring.

A novel filamentous bacteriophage Cf was first isolated from citrus canker pathogen, *Xanthomonas citri* subsp. *citri*, by Dai et al. in Taiwan (Dai, et al., 1980) and has been studied for decades. Cf bacteriophage and its variants have several unique characteristics with its host bacteria, making it become a novel reagent to prevent and inhibit citrus canker disease in this application:

(1) Unlike other filamentous single-stranded DNA bacteriophages that replicate independently and separately from the host genomic DNAs, two Cf phage variants (Cf1t and Cf16) can integrate their DNAs into its *Xanthomonas* host genome (Kuo et al., 1987a, Dai, et al, 1988). Only one copy of Cf1t or Cf16 DNA was stably integrated per host chromosome and become lysogenic, which they replicate together with host genome during bacteria growth (Dai et al., 1987; Kuo et al., 1987b).

(2) In contrast to Cf16, one Cf variant called Cf16-v1 was exceedingly unstable during the integration in host DNA genome, and it produces clear plaques and kills host cells. Only 4% of the infected bacterial cells, rather than 95% as in the case of Cf16, retained the phage genome (Dai, et al, 1987).

(3) The integration region of Cf16-v1 phage and host attachment sites (attP and attB) shared an identical 15-bp "core," 5'-TATACATTATGCGAA-3'. The sequence characteristics indicate that insertion of Cf16-v1 into host genome was accomplished by a site-specific recombination mechanism (Dai et al., 1988).

(4) A virulent Cf variant called Cf1c, was derived from of Cf1t and has been sequenced. The phage yield is higher than Cf1t, and the infected host bacteria growth is drastically reduced (Kuo et al., 1991). Sequence data revealed mutations located in the upstream region of an open reading frame (ORF165) which might encode a 18.2-kDa protein. When the ORF165 in Cf1t was disrupted, this recombinant phage can kill bacteria and form clear plaques (Shieh, et al., 1991).

(5) After *Xanthomonas* host genome was integrated with Cf1t phage DNA, the bacteria is "immuned" and is no longer susceptible to another Cf phage infection. A variant, Cf1tv (or Cf-tv1), that only lyses cell and its DNA never integrates into host DNA genome, was also isolated. Cf1tv has been proven able to superinfect the immuned bacteria that already contain Cf inside. After infected with Cf1tv, bacterial cell division was seriously affected and finally stopped (Kuo et al., 1994). The region that causes this superinfection activity of Cf1tv and similar variant Cf-tv2 has also been mapped (Wang et al., 1999; Cheng et al., 1999).

A Cf phage variant named XacF1 that shares 99% sequence homology with Cf1c was also isolated from *Xanthomonas citri* and reported in Japan in July 2014 (Ahmad, et al., 2014). Infection by XacF1 phage caused several physiological changes to the bacterial host cells, including lower levels of extracellular polysaccharide production, reduced motility, slower growth rate, and dramatic reduction in virulence (Ahmad, et al., 2014) (FIG. 17).

Despite that bacteriophages have been used as a tool to kill bacteria in several studies and patents (U.S. 2010/0068185 A1, 3/2010; U.S. Patent No. 2007/0292395 A1, 12/2007), the specific tool toward to citrus canker disease is unavailable to date. The novel properties make Cf phage and its variants described above become powerful reagents to eradicate citrus canker pathogen in the field.

During our work surveying new phages that can potentially inhibit citrus canker pathogen, a new prophage Cf2 is also identified that integrates within genomic sequence of *Xanthomonas citri* (strain Aw 12879) and is described in this invention. Cf2 phage DNA integrates within genomic sequence of citrus canker pathogen *Xanthomonas citri* (strain Aw 12879) and exists as a prophage. The genome of Cf2 prophage is 6453 nucleotide in size, smaller than Cf1c (7303 nucleotide) or Cf variant XacF1 (7325 nucleotide). Cf2 shares 88% nucleotide sequence homology and has similar gene organization with other filamentous phage phiLf, indicating that Cf2 is also a lysogenic ssDNA phage that belongs to Inoviridae family (FIG. 13A).

Sequence analysis reveals that Cf2 phage contains 12 putative protein-coding genes, including Cf1cp7-like protein, chloride channel EriC, Zot protein gI, minor coat protein gVI, gIX and A, major coat protein B, ssDNA binding protein gV, RstA-type replication protein, 2 hypothetical proteins, and a protein similar to Cf 18.2 kDa (ORF165) protein. Importantly, Cf2 shares only very limited sequence homology (less than 10%) with Cf or its variant XacF1 phage, indicating that it is a new lysogenic phage that infects citrus canker pathogen *X. citri*.

Unlike Cf or phiLf phage, Cf2 phage contains RstA-type replication initiation protein (FIG. 13A). RstA-type replication initiation protein is also found in other lysogenic phages such as phiSMA6, phiSMA7, and phiSMA9 phages that infect bacterial host *Stenotrophomonas maltophilia* and *Xylella fastidiosa* related to *Xanthomonas*. It suggests that Cf2 may require different host factors for its replication. The amino acid sequence of major coat protein B of Cf2 phage shares 76% identity to phiLf phage (FIG. 13B). Characterization of minor coat protein A of Cf2 exhibits novel chimeric properties. Its C-terminus amino acid 303 to 382 is 73% identical to phiLf coat protein A. However, N-terminal amino acid 3 to 211 of Cf2 coat protein A shares 28% identity to Cf homologue (FIG. 12B). Since host specificity of Cf or phiLf phage for *X. citri* and *X. campestris* is mediated by minor coat protein A (Yang and Yang, 1997), this result also suggests that the determinant domain of coat protein A for phage-host specificity is located at its N-terminus.

Cf2 phage DNA also integrates into host bacterial genome at attP sequence located at the C-terminus of 18.2 kDa protein similar to Cf ORF165. Similar location of attP sequence is also found in other lysogenic ssDNA filamentous phages, such as Cf1c, XacF1, phiLf, and Xf (FIG. 14). However, Cf2 contains a different 13-bp core attP sequence (5'-TAATTATGTCAAA-3') (SEQ ID NO: 64) in comparison to 15-bp core attP sequence (5'-TATACATTATGCGAA-3') (SEQ ID NO: 63) identified in other lysogenic filamentous phages (FIG. 14).

The region of DNA sequence and organization that causes superinfection activity of Cf1tv and Cf-tv2 is located at the upstream sequence of ORF165 that contains a predicted promoter region encoding cM1 and cM2 transcripts (FIG. 3, FIG. 5B, FIG. 15) (Cheng et al., 1999). The 49 base pair deletion of Cf-tv2 is upstream of ORF 165. The T in the start codon of ORF165 is mutated of the single base substitution to A in Cf1tv. This T is also located next to −10 consensus TATA box of a predicted promoter for cM1 transcript (FIG. 5B). In addition, the virulent Cf variant XacF1 also contains G to A substitution at this −10 TATA box, which is one nucleotide downstream to Cf1tv mutant (Ahmad, et al., 2014) (FIG. 15). These results lead to the conclusion that this predicted promoter is the determinant for phage immunity.

Cf2 and Cf phage shares almost no sequence homology in their entire genome except the starting 58 nucleotides of cM2 transcript of Cf is 95% identical to Cf2. The −35 and −10 consensus sequences are also found in the upstream of ORF162 in Cf2 (FIG. 15), indicating that the critical region for phage immunity is also conserved in Cf2. These findings suggest that Cf2 can be also engineered into a virulent variant as a bio-control reagent against citrus canker pathogen.

This invention describes the applications of Cf and Cf2 and their variant bacteriophages to infect and kill *Xanthomonas citri* subsp. *citri*, including producing Cf and Cf2 phages in an industrial laboratory and used in citrus groves.

The infectivity of Cf phages requires its minor coat protein A (Yang and Yang, 1997). When Cf genome loses its coat protein A gene, it no longer produces infectious phage particles, and becomes harmless to its bacterial host. Loss of infectivity in the coat protein A-mutated Cf phage can be completely rescued in the presence of minor coat protein A when co-expressed by the other vector. This provides a great system to generate recombinant Cf phages that cannot infect other new bacteria after killing the first bacterial cell they encounter. Unlike other bacteriophage patents in effect so far, this invention also includes a new method to make recombinant Cf phages as "controllable" reagents and do not spread out in natural environment after treating citrus canker in citrus groves. This method will generate bacteriophages as much more secure anti-bacterial reagents without being harmful to the rest of environment.

In taxonomy, Cf phage belongs to Inoviridae family, in which a group of filamentous phages (e.g., Xf, fd, If1, Ike, Pf1, Pf3, phiLF, etc.) has been characterized for their biochemical and biophysical properties (reviewed in Day et al., 1988). For examples, Xf phage was isolated from rice bacterial blight disease pathogen *Xanthomonas oryzae* or phiLF from *Xanthomonas campestris* (Kuo et al., 1969;

Tseng, et al., 1990; Weng and Tseng, 1994). Compared to Cf, both Xf and phiLF phage particles are relatively stable. The Xf phage particles are resistant to treatment with nucleases or proteases and also maintain its full infectivity in phosphate buffer (pH 7.0) when stored in −15° C. for one year (Kuo et al., 1969). phiLF phage particles are stable for 6 months at 4° C. and keep 100% infectivity even at 80° C. for more than 10 minutes (Tseng et al., 1990). These stable properties of the coat proteins also has made Xf phage an excellent model virus in many biophysical studies previously (Lin et al, 1971; Martin et al., 1974; Wiseman and Day, 1977; Chen, et al., 1980; Thomas and Day, 1981; Casadevall and Day, 1982; Thomas et al., 1983; Marzec and Day, 1983; Marzec and Day, 1988; Thomas et al., 1988; Marzec and Day, 1994). We take advantage of the fact that Cf and Xf phages can be packed with the coat protein from each other (Yang and Yang, 1997). This invention also includes a method engineering a recombinant Cf phage with the coat proteins from other members of Inoviridae family (Xf, phiLF, fd, If1, Ike, Pf1, Pf3, Cf2 etc.) to enhance the stability of Cf phage particles for further application.

*Xanthomonas oryzae* pv. *oryzae* causes rice bacterial blight (BB) disease which is one of the most important diseases of rice in most of the rice growing countries (Nino-Liu, et al., 2006). Rice blight has high epidemic potential and is destructive to high-yielding cultivars in both temperate and tropical regions especially in Asia. Its occurrence in the 70 s in Africa and the Americas has led to concerns about its transmission and dissemination. *X. oryzae* pv. *oryzae* can destroy up to 80 percent of a crop if the disease develops early. Even if it develops late, it can nonetheless severely diminish the quality and yield of the grain. Bacterial leaf blight is a prevalent and destructive disease that affects millions of hectares throughout Asia. In Japan alone, annual losses are estimated to be between 22,000 and 110,000 tons. In the Philippines, susceptible varieties lose up to 22.5% of the total harvest during wet seasons and up to 7.2% in the dry season. In resistant crops, these numbers are, respectively, 9.5% and 1.8% (Exconde, 1973).

Research on bacterial blight of rice was commenced in Japan as early as in 1901, and the efforts were focused mainly on ecological studies and chemical control. Since then, significant gains have been made in understanding BB through analysis of the interactions between *X. oryzae* pv. *oryzae* and rice at many levels, including studies focused on the epidemiology, population biology, physiology, cell biology, biochemistry, and molecular genetics of the host pathogen interaction. Bacterium oozes from leaf lesions and is spread by wind or rain, especially when strong storms occur and cause wounds to plants. *X. oryzae* has a wide host range that includes a rice cutgrass called *Leersia sayanuka* which acts as alternative host for the bacterium. The presence of *L. sayanuka*, is also key to the spread of disease because it is a naturally growing weed usually found around patties and has the ability to be infected by the bacterium and spread the bacterium through a rice patty.

One virulent bacteriophages Xp12, was isolated from *Xanthomonas oryzae* pv. *oryzae* in the irrigation water in a rice field in Taiwan in 1968 (Kuo et al., 1968). Xp12 phage is distinguished from other known phages isolated so far because it processes DNA in which all the cytosine residues are completely replaced by 5-methylcytosine (Kuo et al. 1968; Ehrlich et al. 1975). This 5-methylcytosine substitution has made Xp12 an important tool for studying the mechanism of naturally occurring DNA methylation in molecular biology field for decades (Kuo and Tu 1976; Ehrlich et al. 1977; Wang and Ehrlich, 1982; Kuo et al., 1982). Xp12 has been also a model system for analyzing the digestion ability of restriction endonucleases (McClelland and Nelson 1991).

The other bacteriophage, Xf, is a filamentous phage also able to infect rice blight but not inhibit bacterial growth (Kuo, et al., 1969). Xf phage invades the host cells with its coat protein (Kuo and Lin, 1976). However, the sequence information of Xf phage genome has not been reported. We also identify the complete nucleotide sequence of Xf phage genome. In an aspect, the disclosure applies the unique features of Xp12 and Xf phage to engineer these phages and to the control the rice blight disease in the field.

*Xanthomonas campestris* pv. *citri* was reclassified as *X. axonopodis* in 1995. In 2006, the species designations for pv. *citri* and *malvacearum* were revised to *X. citri* and these pathovars are now referred to as subspecies *Xanthomonas campestris*.

BRIEF DESCRIPTION OF THE FIGURES

FIG. 3. (A) Map of Cf RF DNA showing the location of genes and cleavage sites of the restriction endonucleases. Except for ORF165, transcription of all the investigated genes proceeds clockwise. (B) Mutation sites on the Cf-tv2 mutant. (a) DNA sequencing gel showing the mutation in Cf-tv2. (b) Location of the Cf-tv2 mutation on the cf genome (SEQ ID NO: 67). The 49 base pair deletion of Cf-tv2 is shown in boldface type. The amino acid sequence of ORF 165 (SEQ ID NO: 68) is shown in the one-letter code. attP indicates the attachment site for integration in the phage. The T in the start codon of ORF165 represents the mutation of the single base substitution in the virulent mutant, Cfltv (labeled as Cf-tv1 in the figure) (Cheng et al., 1999).

FIG. 5. Primer extension to detect the transcription start sites. (A) Detection of the 5' end of cMa (Left). The four lanes of dideoxy sequencing reactions (C, T, A, G) using the same primer (5'-CAGGATCGAATATGGATGCACGGT-GTA-3') (SEQ ID NO: 69) as in the primer extension reaction are shown. The arrow indicates the 5' end of the cM1 transcript at G5629. (Right) Detection of the 5' end of cM2. The four lanes of dideoxy sequencing reactions (C, T, A, G) using the same primer (5'-TGACAGAGAGGACA-GTGAAAACTATAC-3') (SEQ ID NO: 70) as the primer extension reaction are shown. The arrow indicates the 5' end of the cM2 transcript at C5693. (B) Nucleotide sequence upstream of cM1 and cM2 RNAs (SEQ ID NO: 71 and SEQ ID NO: 72). The translational start site and the amino acid sequence of ORF 165 in the one letter code are shown. The −35 and −10 consensus sequences of a predicted promoter region are underlined. The big arrows indicate the transcriptional start sites of cM1 and cM2. The 49 base pair deleted in cf-tv2 are shown in boldface type. In (A): lane 1, uninfected *Xanthomonas*; lane 2, *Xanthomonas* infected with cf; and lane 3, *Xanthomonas* infected with cf-tv2 (Cheng et al, 1999).

FIG. 6. Application and generation of Cf-type phages to inhibit citrus canker disease. (A) Cf-M phages are generated by treating Cf-type phages with chemical mutagens that cause variety of gene mutations (orange dots). (B) Cf-Super phages contain mutations nearby or within ORF165 region in RF DNA of Cf-type phages. Arrows indicate the transcriptional start sites of cM1 and cM2 in FIG. 5B. Cf-Super phages are able to infect both uninfected *X. citri* or bacteria that are previously infected by other Cf-type phages and immuned. Cf-Super phages kill *X. citri* by lysis of bacteria, and new phages are released to infect more bacteria in a lesion of citrus canker. (C) Summary of the process flowchart of generation and application of Cf-type phages in this patent. Mutated Cf-type phages (A) are used to infect *X. citri*, or (B) recombinant RF DNAs of Cf-Super are electroporated in *X. citri* cells. After propagating in *X. citri* cells, Cf-type phages are harvested and purified from the growth medium. Infectivity and quality control of Cf-type phages are assayed, and phage particles are aliquoted and stored in a lab. In an orange grove, Cf-type phages are sprayed or misted on the citrus trees for field tests. Different Cf-type and variants phages are screened for the control of *X. citri* with better pathogen inhibition effect than others. Cf-type phages with the greatest inhibitory effects on citrus canker disease are selected for the large-scale production and commercial use.

FIG. 7. Generation of a controllable "single-shot infectious" Cf-type (SS-iCf) phage in this patent. Component A is a plasmid DNA that contains coat protein A gene of Cf-type phage and an essential nutrition gene X. Component B is a recombinant Cf-type RF DNA which the coat protein A gene is replaced by a nutrition gene Y. Component A and B are electroporated together into *X. citri* mutants lack of both nutrition genes X and Y, then bacteria are grown in a selected nutrition medium to produce SS-iCf phages. SS-iCf phages can infect and kill *X. citri* cells by the lysis of bacterial cells. Because the genome of SS-iCf phages do not contain the coat protein A gene essential for infectivity, SS-iCf phages cannot propagate into new progeny phages and spread in the filed anymore after being used.

FIG. 8. Generation of recombinant Cf-type phages to improve the storage shelf life. (A) The XC DNA fragments encoding coat proteins from other inoviruses are cloned into RF DNAs of Cf-type phages to replace the major coat protein B gene. The Cf-type RF DNAs containing XC fragments are electroporated into *X. citri* bacteria and amplified. Cf-XC phage particles are harvested from the medium. (B) Generation of the controllable SS-iCf-XC phages. Component C is a plasmid containing XC DNA fragments and an essential nutrition gene X. Component D is recombinant Cf-type RF DNA which the major coat protein B gene is replaced by a DNA fragment of a nutrition gene Y. Component E is recombinant Cf-type RF DNA with an TA insertion (orange dot) that abolishes the expression of major coat protein B. The mixture of "Component C+D", or "component C+E", respectively, is electroporated into *X. citri* bacteria mutant lack of nutrition genes X and Y. *X. citri* cells are grown in a selected nutrition medium. SS-iCf-XC phage particles are harvested from the medium. Because the genome of SS-iCf-XC phages do not contain a functional coat protein B gene, SS-iCf-XC phages cannot produce new progeny phages in the filed after infecting and killing *X. citri* bacteria.

FIG. 9. Generation of Cf-type phages able to kill *X. citri* bacteria. (A) A DNA fragment encoding a toxic gene able to kill *X. citri* bacteria is cloned into RF DNAs of Cf-type phages. The recombinant Cf-type RF DNAs containing a toxic gene (brown dots) are electroporated into *X. citri* bacteria and amplified. Cf-killer phage particles are harvested from the medium. (B) Generation of the controllable SS-iCf-killer phages. Component A is a plasmid DNA that contains coat protein A gene of Cf-type phage and an essential nutrition gene X. Component J is recombinant Cf RF DNAs which contain a toxic gene, and the coat protein A gene is replaced by nutrition gene Y. Component A and J are electroporated together into *X. citri* mutants lack of both nutrition genes X and Y, then bacteria are grown in a selected nutrition medium to produce SS-iCf-killer phages. SS-iCf-killer phages can infect and kill *X. citri* cells. Because the genome of SS-iCf-killer phages do not contain the coat protein A gene essential for infectivity, SS-iCf phages cannot propagate into new progeny phages and spread in the filed anymore after being used.

FIG. 10. Generation and application of a Cf-Shuttle vector that can carry a foreign gene that integrates into *X. citri* host DNA genome. Component A is a plasmid DNA that contains coat protein A gene of Cf-type phage and an essential nutrition gene X. Component K (Cf-Shuttle vector) contain a DNA fragment encoding a foreign gene to replace coat A gene in RF DNA of Cflt phage. The mixture of Component K and component A are electroporated together into *X. citri* mutants lack of nutrition gene X. Cells are grown in a selected nutrition medium. Cf-shuttle vector will integrate into *X. citri* host genome and replicates with bacteria. With Component A, Cf-Shuttle phages can be also generated and released into medium.

FIG. 11. Application and generation of XP12 variant phages to inhibit rice blight disease. (A) Summary of the process flowchart of generation and application of XP12 variant phages in this patent. XP12 variant phages are generated either by treating XP12 phages with chemical mutagens, or XP12 DNA is mutated by PCR. After propagating in *X. oryzae* cells, XP12 phages are harvested and purified from the growth medium. Infectivity and quality control of XP12 phages are assayed, and phage particles are aliquoted and stored in a lab. In a rice field, XP12 variant phages are sprayed or misted in field tests to screen for the control of *X. oryzae* with better pathogen inhibition effect than others. XP12 phages with the greatest inhibitory effects on rice blight are selected for the large-scale production and commercial use. XP12 variant phages are able to infect and kill *X. oryzae* by lysis of bacteria, and new progeny XP12 phages are released to infect more bacteria in a lesion of rice blight. (B) Generation of a controllable SS-iXP12 phage in this patent. Component L is a plasmid DNA that contains coat protein and RNA polymerase genes of XP12 phage and an essential nutrition gene X. Component M is a recombinant XP12 DNA, which the coat protein and RNA polymerase gene are replaced by nutrition gene Y and Z, respectively. Component L and M are electroporated together into *X. oryzae* mutant lack of both nutrition genes X, Y, and Z. Bacteria are grown in a selected nutrition medium to produce SS-iXP12 phages. SS-iXP12 phages can infect and kill *X. oryzae* cells by the lysis of bacterial cells. Because the genome of SS-iXP12 phages do not contain the coat protein and RNA polymerase gene, SS-iXP12 phages cannot propagate into new progeny phages and spread in the filed anymore after being used.

FIG. 12. Application and generation of Xf variant phages to inhibit rice blight disease. (A) Summary of the process flowchart of generation and application of Xf variant phages in this patent. Xf variant phages are generated either by treating Xf phages with chemical mutagens, or Xf RF DNA is mutated by PCR and electroporated into *X. oryzae*. After propagating in *X. oryzae* cells, Xf phages are harvested and purified from the growth medium. Infectivity and quality control of Xf phages are assayed, and phage particles are aliquoted and stored in a lab. In a rice field, Xf variant phages are sprayed or misted in field tests to screen for the control of *X. oryzae* with better pathogen inhibition effect than others. Xf variant phages with the greatest inhibitory effects on rice blight are selected for the large-scale production and commercial use. Xf variant phages are able to infect and kill *X. oryzae* by lysis of bacteria, and new progeny Xf phages are released to infect more bacteria in a lesion of rice blight. (B) Generation of a controllable SS-iXf phage in this patent. Component N is a plasmid DNA that contains coat protein B gene of Xf phage and an essential nutrition gene X. Component O is a recombinant Xf DNA, which the coat protein B gene is replaced by nutrition gene Y. Component N and O are electroporated together into *X. oryzae* mutant lack of both nutrition genes X and Y. Bacteria are grown in a selected nutrition medium to produce SS-iXf phages. SS-iXf phages can infect and kill *X. oryzae* cells by the lysis of bacterial cells. Because the genome of SS-iXf phages do not contain the coat protein B gene, SS-iXf phages cannot propagate into new progeny phages and spread in the filed anymore after being used.

FIG. 13. Characterization of Cf2 phage genome isolated from *X. citri*. (A) Comparison of genome organization of Cf2 and phiLf phage. Direction of Cf1cp7-like protein and Cf 18.2 kDa/ORF165-like protein transcripts is opposite to other ORFs. (B)(Upper) Comparison of amino acid sequences of major coat protein B of Cf2 (SEQ ID NO: 45) and phiLf (SEQ ID NO: 15). (Middle and bottom) Comparison of amino acid sequences of minor coat protein A between Cf2 (SEQ ID NO: 73) and Cf (middle) (SEQ ID NO: 74), or between Cf2 (SEQ ID NO: 75) and phiLf (SEQ ID NO: 76) (bottom).

FIG. 14. Nucleotide sequence in the vicinity of the phage attachment site (attP) identified in lysogenic phages (Cf1c (SEQ ID NO: 77), XacF1 (SEQ ID NO: 78), Cf2 (SEQ ID NO: 79), phiLF (SEQ ID NO: 80), and Xf (SEQ ID NO: 81). The core attP sequence is underlined. Asterisk shows core attP sequences different from 5'-TATACATTATGCGAA-3' (SEQ ID NO: 63) in Cf2 phages. All attP sites are located at the C-terminus of an ORF encoding a protein similar to Cf1cp8 (18.2 kDa protein, or ORF165 in FIG. 3). Amino acid sequence and number of ORF165 homologue of each phage is shown (Cf1c (SEQ ID NO: 82, XacF1 (SEQ ID NO: 83, Cf2 (SEQ ID NO: 84), phiLF (SEQ ID NO: 85), and Xf (SEQ ID NO: 86).

FIG. 17. Lesions on detached lemon leaves inoculated with cells of *Xanthomonas citri* Xac MAFF301080. (A) Canker symptoms that had developed on leaves 1, 2, 3, and 4 week spost-infection by the needle-pricking method. Leaves were inoculated with uninfected cells (upper panels) or Cf strain XacF1-infected cells (lower panels). Leaf are as shown by a square were examined by photomicroscopy and the microscopic images are shown under each corresponding leaf. Characteristic canker lesions occurred with uninfected cells, while no obvious cankers developed on XacF1-infected cells. (B) Comparison of the size of lesions formed on lemon leaves. (C) Lesions formed on lemon leaves by infiltration of bacterial cells. Uninfected MAFF301080 cells were applied to two areas of the leaf (left half of the abaxial side), and XacF1-infected cells were similarly applied to the right side (upper panels). Lesions on the axial side are also shown in lower panels. Lesions on both lower and upper surfaces of leaves inoculated with the uninfected cells showed severe symptoms, expanding with time. No lesions formed on either surface of the leaves infected with XacF1-infected cells (Ahmad et al., 2014).

DETAILED DESCRIPTION

Figure 1A:
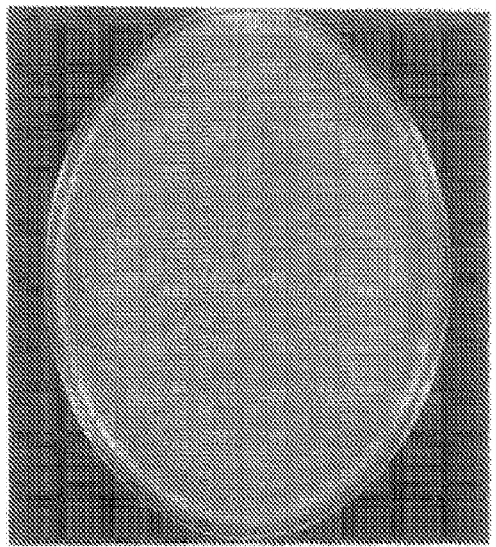
FIG. 1: (A) The plague morphology of bacteriophage Cf (left) and Cflt (right). (B) Electron micrograph of bacteriophage Cflt, stained with 2% phosphotungstic acid is described (Kuo et al., 1987).

In an aspect, the disclosure provides for a composition, seed, plant, vector, or construct comprising a sequence described herein.

Proteins and the nucleic acid sequences that encode them described herein are useful in controlling and treating plant pathogens associated with plant bacterial pathogens, such as citrus canker and rice blight.

In another aspect, the disclosure provides for methods of utilizing a sequence described herein to treat or reduce pest activity. In yet another aspect, the disclosure provides for methods of utilizing a sequence described herein to treat or reduce pest activity, for example, pest activity in *Xanthomonas*, for example, *X. albilineans*, *X. arboricola* sp., *X.*

*axonopodis* sp., *X. bromi*, *X. campestris* spp., *X. cassavae*, *X. citri*, *X. codiaei*, *X. cucurbitae*, *X. cynarae*, *X. fragariae*, *X. fuscans*, *X. gardneri*, *X. hortorum*, *X. hyacinthi*, *X. melonis*, *X. oryzae* sp., *X. pisi*, *X. populi*, *X. sacchari*, *X. theicola*, *X. translucens* sp., *X. vasicola*, *X. vesicatoria*, *X.* spp., but also including other bacteria such as *Xylella fastidiosa*, *Pseudomonas* and Enterobacteriaceae infection.

In an aspect, the disclosure provides for a method of inhibiting, reducing, or treating infection or infestation of citrus canker, rice blight, black rot, and/or bacterial leaf spot, leaf spot disease, sugarcane leaf scald, and other *Xanothomonas* or *Xylella* infection.

In an aspect, nucleotide sequences encoding the proteins of the present invention include the sequence set forth in SEQ ID NO:1-2, 24, 25, 26 and variants, fragments, and complements thereof. In another aspect, proteins of the present invention are encoded by a nucleotide sequence sufficiently identical to the nucleotide sequence of SEQ ID NO:1-2, 24, 25, 26 or the pesticidal proteins are sufficiently identical to the amino acid sequence set forth in SEQ ID NO:3-23, 27-62. By "sufficiently identical" is intended an amino acid or nucleotide sequence that has at least about 50%, 60%, or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

In another aspect, the disclosure provides for a protein or polypeptide having an amino acid sequence that is at least about 50%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of any of SEQ ID NO:3-23, 27-62. Variants also include polypeptides encoded by a nucleic acid molecule that hybridizes to the nucleic acid molecule of SEQ ID NO:3-23, 27-62 or a complement thereof, under the condition that permit a formation of a nucleic acid duplex at the temperature from 20° C.-29° C. below the melting temperature of the nucleic acid duplex in the hybridization and washing solution with 0.165-0.33 molar concentration of sodium chloride. Variants include polypeptides that differ in amino acid sequence due to mutagenesis. Variant proteins encompassed by the present invention are biologically active, that is they continue to possess the desired biological activity of the native protein, that is, retaining pesticidal activity. In some embodiments, the variants have improved activity relative to the native protein.

As described in the sequence listing, SEQ ID NO: 3 comprises a Cf1cp1, ssDNA-binding protein "=pV of Ff phage" and is encoded by SEQ ID NO: 1: nucleotide number 7087-7308; 1-75.

As described in the sequence listing, SEQ ID NO: 4 comprises Cf1cp2, B coat protein and is encoded by SEQ ID NO: 1: nucleotide number 313-585.

As described in the sequence listing, SEQ ID NO: 5 comprises Cf1cp3, minor coat protein A=pill of M13/Fd phage and encoded by SEQ ID NO: 1: nucleotide number 662-1918.

As described in the sequence listing, SEQ ID NO: 6 comprises Cf1cp4, ATPase, zonular occludens toxin, able to reversibly alter intestinal epithelial tight junctions, allowing the passage of macromolecules through mucosal barriers=pI in F1 phage, which is encoded by SEQ ID NO: 1: nucleotide number 2481-3647.

As described in the sequence listing, SEQ ID NO: 7 comprises Cf1cp5, conjugal transfer protein TrbP/Trax and is encoded by SEQ ID NO: 1: nucleotide number 3647-4294.

As described in the sequence listing, SEQ ID NO: 8 comprises Cf1cp6, DUF 4124, which is a potential secreted protein and encoded by SEQ ID NO: 1: nucleotide number 4310-4702.

As described in the sequence listing, SEQ ID NO: 9 comprises Cf1cp7, similar to ORF110 of *Xanthomonas campestris* and is encoded by SEQ ID NO: 1: nucleotide number 4710-5123.

As described in the sequence listing, SEQ ID NO: 10 comprises Cf1cp8, ORF165, 18.2 kDa protein, for virus immunity of *Xanthomonas* citrus and is encoded by SEQ ID NO: 1: nucleotide number 5120-5620.

As described in the sequence listing, SEQ ID NO: 11 comprises Cf1cp9, a probable site-specific integrase; similar to Replication-associated protein G2P=pI in M13/f1 phage and is encoded by SEQ ID NO: 1: nucleotide number 6057-7090.

As described in the sequence listing, SEQ ID NO: 12 comprises ORF165, and is encoded by SEQ ID NO: 1: nucleotide number 5120-5620.

As described in the sequence listing, SEQ ID NO: 27 comprises XacF1 ORF1, and is encoded by SEQ ID NO: 24: nucleotide number 1-1080.

As described in the sequence listing, SEQ ID NO: 28 comprises XacF1 ORF2, and is encoded by SEQ ID NO: 24: nucleotide number 1077-1373.

As described in the sequence listing, SEQ ID NO: 29 comprises XacF1 ORF3, and is encoded by SEQ ID NO: 24: nucleotide number 1405-1605.

As described in the sequence listing, SEQ ID NO: 30 comprises XacF1 ORF4, and is encoded by SEQ ID NO: 24: nucleotide number 1611-1868.

As described in the sequence listing, SEQ ID NO: 31 comprises XacF1 ORF5, and is encoded by SEQ ID NO: 24: nucleotide number 1928-1996.

As described in the sequence listing, SEQ ID NO: 32 comprises XacF1 ORF6, and is encoded by SEQ ID NO: 24: nucleotide number 996-3474.

As described in the sequence listing, SEQ ID NO: 33 comprises XacF1 ORF7, and is encoded by SEQ ID NO: 24: nucleotide number 3474-3791.

As described in the sequence listing, SEQ ID NO: 34 comprises XacF1 ORF8, and is encoded by SEQ ID NO: 24: nucleotide number 3788-4954.

As described in the sequence listing, SEQ ID NO: 35 comprises XacF1 ORF9, and is encoded by SEQ ID NO: 24: nucleotide number 4954-5601.

As described in the sequence listing, SEQ ID NO: 36 comprises XacF1 ORF10, and is encoded by SEQ ID NO: 24: nucleotide number 5617-6009.

As described in the sequence listing, SEQ ID NO: 37 comprises XacF1 ORF11, and is encoded by SEQ ID NO: 24: nucleotide number 6047-6430.

As described in the sequence listing, SEQ ID NO: 38 comprises XacF1 ORF12, and is encoded by SEQ ID NO: 24: nucleotide number 6427-6885.

As described in the sequence listing, SEQ ID NO: 39 comprises XacF1 ORF13, and is encoded by SEQ ID NO: 24: nucleotide number 7015-7203.

As described in the sequence listing, SEQ ID NO: 40 comprises Cf2 similar to CF1cp7 protein, and is encoded by SEQ ID NO: 25: nucleotide number 98-424.

As described in the sequence listing, SEQ ID NO: 41 comprises Cf2 chloride channel EriC protein, and is encoded by SEQ ID NO: 25: nucleotide number 491-802.

As described in the sequence listing, SEQ ID NO: 42 comprises Cf2 Zot protein, and is encoded by SEQ ID NO: 25: nucleotide number 812-2156.

As described in the sequence listing, SEQ ID NO: 43 comprises Cf2 minor coat protein, and is encoded by SEQ ID NO: 25: nucleotide number 2158-2478.

As described in the sequence listing, SEQ ID NO: 44 comprises Cf2 minor coat protein A, and is encoded by SEQ ID NO: 25: nucleotide number 2489-3682.

As described in the sequence listing, SEQ ID NO: 45 comprises Cf2 major coat protein B, and is encoded by SEQ ID NO: 25: nucleotide number 3817-3945.

As described in the sequence listing, SEQ ID NO: 46 comprises Cf2 minor coat protein, and is encoded by SEQ ID NO: 25: nucleotide number 3972-4223.

As described in the sequence listing, SEQ ID NO: 47 comprises Cf2 ssDNA binding protein, and is encoded by SEQ ID NO: 25: nucleotide number 4227-4505.

As described in the sequence listing, SEQ ID NO: 48 comprises Cf2 phage replication protein RstA, and is encoded by SEQ ID NO: 25: nucleotide number 4484-5371.

As described in the sequence listing, SEQ ID NO: 49 comprises Cf2 conserved protein, and is encoded by SEQ ID NO: 25: nucleotide number 5371-5558.

As described in the sequence listing, SEQ ID NO: 50 comprises Cf2 hypothetical protein, and is encoded by SEQ ID NO: 25: nucleotide number 5728-5952.

As described in the sequence listing, SEQ ID NO: 51 comprises Cf2 18.2 kDa protein, and is encoded by SEQ ID NO: 25: nucleotide number 6080-6468.

As described in the sequence listing, SEQ ID NO: 52 comprises Xf similar to Cf1cp7 protein, and is encoded by SEQ ID NO: 26: nucleotide number 90-473.

As described in the sequence listing, SEQ ID NO: 53 comprises Xf TrbP protein, and is encoded by SEQ ID NO: 26: nucleotide number 645-1292.

As described in the sequence listing, SEQ ID NO: 54 comprises Xf Zot protein, and is encoded by SEQ ID NO: 26: nucleotide number 1294-2484.

As described in the sequence listing, SEQ ID NO: 55 comprises Xf hypothetical protein, and is encoded by SEQ ID NO: 26: nucleotide number 2481-2810.

As described in the sequence listing, SEQ ID NO: 56 comprises Xf minor coat protein A, and is encoded by SEQ ID NO: 26: nucleotide number 2810-4258.

As described in the sequence listing, SEQ ID NO: 57 comprises Xf major coat protein B, and is encoded by SEQ ID NO: 26: nucleotide number 4353-4583.

As described in the sequence listing, SEQ ID NO: 58 comprises Xf ssDNA binding protein, and is encoded by SEQ ID NO: 26: nucleotide number 4802-5098.

As described in the sequence listing, SEQ ID NO: 59 comprises Xf replication initiation protein, and is encoded by SEQ ID NO: 26: nucleotide number 5095-6135.

As described in the sequence listing, SEQ ID NO: 60 comprises Xf hypothetical protein, and is encoded by SEQ ID NO: 26: nucleotide number 6288-6500.

As described in the sequence listing, SEQ ID NO: 61 comprises Xf hypothetical protein, and is encoded by SEQ ID NO: 26: nucleotide number 6500-6685.

As described in the sequence listing, SEQ ID NO: 62 comprises Xf Cf1c 18.2 kDa-like protein, and is encoded by SEQ ID NO: 26: nucleotide number 6771-7205.

It is recognized that DNA sequences of a pesticidal protein may be altered by various methods, and that these alterations may result in DNA sequences encoding proteins with amino acid sequences different than that encoded by a pesticidal protein of the present invention. This protein may be altered in various ways including amino acid substitutions, deletions, truncations, and insertions of one or more amino acids of SEQ ID NO:3-23, 27-62 including up to about 1, about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100 or more amino acid substitutions, deletions or insertions.

The skilled artisan will further appreciate that changes can be introduced by mutation of the nucleotide sequences of the invention thereby leading to changes in the amino acid sequence of the encoded pesticidal proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more, predicted, nonessential amino acid residues. A "nonessential" amino acid residue is a residue that can be altered from the wild-type sequence of a pesticidal protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In an aspect, amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the invention (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the invention (e.g., residues that have only conservative substitutions between all proteins contained in the alignment homologous proteins). However, one of skill in the art would understand that functional variants may have minor conserved or nonconserved alterations in the conserved residues.

Unless otherwise specified, "a" or "an" means "one or more". As used herein, the terms "and" and "or" may be used to mean either the conjunctive or disjunctive. That is, both terms should be understood as equivalent to "and/or" unless otherwise stated. As used herein, unless otherwise stated for a particular parameter, the term "about" refers to a range that encompasses an industry-acceptable range for inherent variability in analyses or process controls, including sampling error. Consistent with the Model Guidance of AAFCO, inherent variability is not meant to encompass variation associated with sloppy work or deficient procedures, but, rather, to address the inherent variation associated even with good practices and techniques.

As used herein, the term "coating" means a partial or complete covering that covers at least a portion of a surface, for example a surface of a food, plant, seed or fruit. In one example, a food, plant, seed or fruit may be partially covered with a coating such that only part of the plant is covered, and part of the plant is not covered and is thus exposed. In another example, the plant may be completely covered with a coating such that the entire plant is covered and thus not exposed. Thus a coating may cover from a negligible amount up to the entire surface. A coating can also be coated onto other coatings such that a layering of coatings can be present. For example, a plant can be coated with coating A, and coating A can be coated with coating B, such that coating A and coating B each form a layer.

As used herein, the terms "bacteriophage" and "phage" are used interchangeable and refer to a virus which is lytic or otherwise harmful to bacteria of one or more undesirable strains. Undesirable bacteria may be or may produce compounds which are potentially pathogenic for plants, or may be associated with spoilage, malodor, aesthetic decline, or other deterioration of a food product colonized by the undesirable bacteria. As used herein, "bacterium", "bacteria" or "target bacterium" refers to an undesirable microorganism susceptible to infection and lysis, apoptosis, or alternate modes of cell death caused by a bacteriophage. Different strains of bacteriophage may infect different strains of bacteria with different results, or may infect some strains of bacteria but not others.

As used herein, "isolated" will mean material removed from its original environment (e.g., the natural environment in which the material occurs) or liquid culture, and thus is "altered by the hand of man" from its natural environment. Isolated material may be, for example, foreign nucleic acid included in a vector system, foreign nucleic acid contained within a host cell, or any material which has been removed from its original environment and thus altered by the hand of man. Isolated material further encompasses isolated phage or particular bacterial isolates of *Xanthomonas citri* subsp. *citri* or *Xanthomonas oryzae* pv. *oryzae*, isolated and cultured separately from the environment in which it was located, where these isolates are present in purified compositions that do not contain any significant amount of other bacteriophage or bacterial strains, respectively. As used herein, "significant" will mean an amount of a substance present in the total measured composition, wherein the substance is present in greater than 1% of the total volume or concentration of the composition.

As used herein, "recombinant", "variants", and "recombinant variants" will mean genomic materials (nucleotides, DNA, RNA, proteins) are artificially engineered and have the same nucleotide and/or amino acid sequences where one or more residues are added, deleted, or substituted.

As used herein, "colonization" or "colonized" will refer to the presence of *X. citri* subsp. *citri*, *X. oryzae* pv. *oryzae X. albilineans*, *X. arboricola* sp., *X. axonopodis* sp., *X. bromi*, *X. campestris* spp., *X. cassavae*, *X. citri*, *X. codiaei*, *X. cucurbitae*, *X. cynarae*, *X. fragariae*, *X. fuscans*, *X. gardneri*, *X. hortorum*, *X. hyacinthi*, *X. melonis*, *X. oryzae* sp., *X. pisi*, *X. populi*, *X. sacchari*, *X. theicola*, *X. translucens* sp., *X. vasicola*, *X. vesicatoria*, *X.* spp., *Xylella fastidiosa*, *Pseudomonas* and Enterobacteriaceae on a plant, foodstuff or environmental surface without perceptible significant alteration to that plant, foodstuff or surface other than the presence of bacteria. The terms "colonization" and "colonized" stand in contrast to the terms "infection" or "infected" which are commonly understood to require perceptible deleterious alteration as part of their definition. "Colonization" and "colonized" may also refer to the presence of bacteria in or on a plant without perceptible damage, alteration, or disease.

As used herein, "ATCC" will mean the "American Type Culture Collection", which is located at 10801 University Boulevard, Manassas, Va., 20110-2209, USA.

"Centrifugation", the name given to separation applications which involve spinning around an axis to produce a centrifugal force, is a way to increase the magnitude of the gravitational field. The particles or materials (such as viruses, phages, DNA etc.) in suspension experience a radial centrifugal force moving them away from the axis of rotation. The radial force generated by the spinning rotor is expressed relative to the earth's gravitational force and herein expressed as "g-force" (with g from "gravitational").

As used herein, "ORF" will mean an "Open Reading Frame" which is an in-frame sequence of codons that (in view of the genetic code) correspond to or encode a protein or peptide sequence. Two ORFs correspond to each other if the sequences or their complementary sequences encode the same amino acid sequences. An ORF sequence, operably associated with appropriate regulatory sequences, may be transcribed and translated into a polypeptide in vivo. As used herein, "homology" will mean the degree of similarity between two nucleic acids (based on comparison of the chemical structure of the nucleic acids, as expressed by the sequence of nucleotides making up the nucleic acid or biologic function, as determined by whether two nucleic acids of minimum length 500 nucleotides and maximum length 10,000 nucleotides will hybridize to form a double-stranded complex).

As used herein, "purify" will mean a method to generate a macromolecule essentially free of any similar macromolecules that would normally be found with it in nature. In other words, a purified protein is in a composition that contains no more than 1% other protein from the same taxonomic species. A purified composition excludes media components, recipients or other non-contaminating compounds resulting from culturing, processing or formulating the composition.

As used herein, "amplification" will mean the in vitro production of multiple copies of a particular nucleic acid sequence. The amplified sequence is usually in the form of DNA. A variety of techniques for carrying out such amplification are described in a review article (Van Brunt, 1990). Polymerase chain reaction (PCR) is a prototype of nucleic acid amplification, and use of PCR herein should be considered exemplary of other suitable amplification techniques.

A regular method of quantification by culturing and counting includes a technique which is typically referred to as a "plaque assay". In plaque assays, the phages that are to be quantified are mixed with a known concentration of host bacterial cells and transferred to a liquid (e.g., buffer, mineral salts diluent, or broth). The mixture is then transferred to a semisolid growth medium. The concentration of host cells must be sufficiently great to form a confluent layer, which is typically referred to as a "lawn," in the semisolid growth medium as the cells grow. During incubation of the phage-bacteria mixture, many of the viable viruses infect host cells. Subsequently, new viruses are produced within infected host cells, which are eventually destroyed, or "lysed," so that new viruses may be released. The new viruses then attack and eventually lyse cells that are adjacent to host cells from which the new viruses were released. This spread of infection, which continues as long as host cells are metabolizing, results in formation of clear areas, which are typically referred to as "plaques," in the host cell lawn. The number of viruses that were present in the original mixture is determined by counting the number of plaques that are formed in the host cell lawn. Accordingly, viruses that are quantified by this method are referred to as "plaque-forming units" ("PFU"). The term "colony-forming unit" ("CFU") is an estimate of viable bacterial numbers. The appearance of a visible colony requires significant growth of the initial cells plated—at the time of counting the colonies it is not possible to determine if the colony arose from one cell or 1,000 cells. Therefore, the results are given as CFU/mL (colony-forming units per milliliter) for liquids, and CFU/g (colony-forming units per gram) for solids to reflect this uncertainty (rather than cells/mL or cells/g).

As used herein, the "lytic" cycle means bacteriophage replication results in the destruction of the infected cell and its membrane. In the lytic cycle, the viral DNA exists as a separate molecule within the bacterial cell, and replicates separately from the host bacterial DNA. In contrast, the "lysogenic" cycle used herein is characterized by integration of the bacteriophage nucleic acid into the host bacterium's genome or formation of a circular replicon in the bacterium's cytoplasm. In this condition the bacterium continues to live and reproduce normally. The genetic material of the bacteriophage, herein called a "prophage", can be transmitted to daughter cells at each subsequent cell division, and a later event (such as nutrition depletion, UV radiation or the presence of certain chemicals) can release it, causing proliferation of new phages via the lytic cycle. As used herein, the "multiplicity of infection" ("MOI") is the ratio of infectious agents (e.g. phage or virus) to infection targets (e.g. cell or bacteria). For example, when referring to a group of bacterial cells inoculated with infectious phage particles, the multiplicity of infection or MOI is the ratio of the number of infectious virus particles to the number of target cells present in a defined space.

Cf bacteriophage has binding specificity for citrus canker bacterium *Xanthomonas citri* subsp. *citri*, and is capable of lysing infected host *Xanthomonas* cells. Cf phage can also grow through lysogenic cycle by integrating phage DNA into host genome. Particularly preferred Cf bacteriophages have biological activity (e.g., the ability to lyse host cells and/or the ability to produce phage progeny in a host cell). The invention further contemplates "variants" or "strains" of Cf phages, which are phages having variation(s) less than 10% differences in the genomic sequences and polypeptides encoded thereby while retaining the same or different general genotypic and phenotypic characteristics as the parental Cf phage. Variants of Cf phages encompass polymorphic variants, such as XacF1 phage, which difference of nucleotide sequence from Cf (Cf1c or Cf1t) is less than 1% (Kuo, et al., 1991; Ahmad, et al., 2014). The invention also contemplates "recombinant" Cf phages, which are Cf phages having modified genotypic or phenotypic characteristics relative to the deposited Cf bacteriophage, particularly encompass specifically designed Cf bacteriophage harboring genes encoding novel phenotypic traits. Such recombinant Cf phages are engineered to contain or lose genes having traits not found in wild-type Cf phage. If not specified, "Cf variants" in this invention include (1) "Cf1t, Cf1c, Cf1tv, Cf16, Cf16-v1, Cf-tv2", (2) "Cf mutants induced by chemical mutagens", and (3) the recombinant Cf bacteriophages". "Recombinant bacteriophages" or "recombinant phages" will mean genomic materials (nucleotides, DNA, RNA, proteins) of phages are artificially engineered and have the same nucleotide and amino acid sequences where one or more residues are added, deleted, or substituted. Cf2 and its "variants" in this invention will include "Cf2 mutants" induced by chemical mutagens and "the recombinant Cf2 phages". If not specified, "Cf-type phages" in this invention include "Cf, XacF1, and Cf2 phages" because they are all able to infect *Xanthomonas citri*. Xf or Xp12 "variants" in this invention will include "Xf or Xp12 mutants" induced by chemical mutagens and "the recombinant Xf or Xp12 phages".

As used herein, "immune" or "immuned" will mean that bacteria that have been infected by a phage and they are not susceptible for infection by the other phage. "Superinfect" or "Superinfection" will mean a phage is still capable of infecting an immuned bacteria.

EXAMPLES

Example 1: Growth and Purification of *Xanthomonas citri* Bacterium and Cf-Type Phages Propagation of bacteria and phages is performed as described as the following, which are each hereby incorporated by reference in their entireties (Yang and Kuo, 1984; Kuo, 1987). Citrus canker pathogen, *Xanthomonas citri* subsp. *citri* (ATCC 49118), isolated from the lime *Citrus aurantifolia* in Florida was purchased from ATCC (Manassas, Va.). Unless specified, it is used as a bacterial host for cultivation of Cf-type phages and variants such as Cf1t, Cf1c, Cf1tv, Cf16, Cf16-v1, Cf-tv2, XacF1, Cf2, and the recombinant Cf and Cf2 phages. *Xanthomonas citri* subsp. *citri* was grown in potato-sucrose medium (PS medium), which contained, per liter: fresh potato, 200 g; $Ca(NO_3)_2$, 0.5 g; $Na_2HPO_4.12H_2O$, 0.2 g; peptone, 5 g; sucrose, 15 g. Alternatively, the Luria Broth (LB) medium is used (10 g tryptone, 5 g yeast extract, and 10 g NaCl per liter). The bacterial cells are plated or streaked on LB agar plates and grown at 30° C. for 48 hr. These plates are then stored at 4° C. Phages are harvested from semi-confluent lysis on double-layer LB plates. Distilled water or buffer is added to the plates, which are kept overnight in a cold room. The phage solution is collected and the cell debris is removed by centrifugation at 10000 g-force for 30 min at 4° C. The phage titer is assayed by the double-layer agar method. The phage is stored at 4° C. for use.

Cf-type phages are purified as described in (Kuo et al., 1987), which is hereby incorporated by reference in its entirety. An overnight infected *Xanthomonas citri* subsp. *citri* bacterial culture is harvested, and host cells and debris is removed by centrifugation at 6000 g-force for 10 min. Solid NaCl is added to the supernatant to a final concentration of 0.05 M, and polyethyene glycol 6000 is then added to a final concentration of 3%. After thorough stirring, the mixture is allowed to settle overnight in a cold room. The precipitate is collected by centrifugation at 6000 g-force for 10 minutes and then resuspended in distilled $H_2O$. Further purification was carried out by centrifugation through a CsCl step density gradient, (1.18, 1.25, 1.29, 1.34, and 1.39 g/ml) in a Beckman SW41 swinging bucket rotor at 23,000 rpm for 22 hr at 5° C.

Figure 1B:
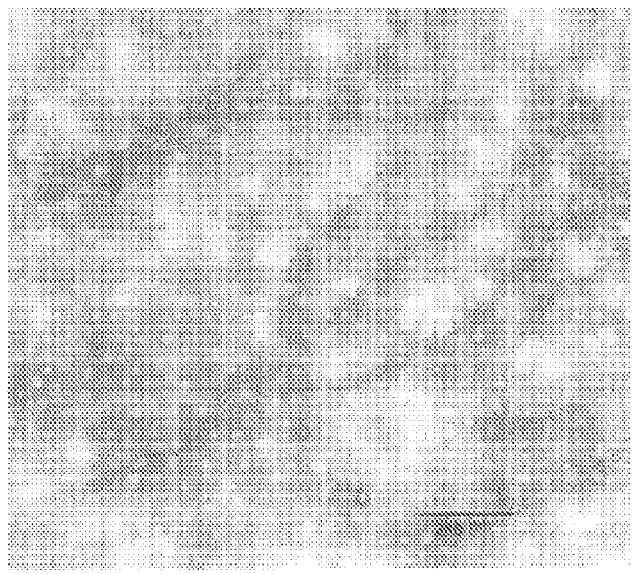

The comparison of the lytic effect during Cf (left) and Cflt (right) infection on the plague morphology of *Xanthomonas citri* on the agarose PS culture plate is shown in FIG. 1A. Cflt phage DNA can integrate into *Xanthomonas citri* genome and becomes lysogenic, therefore it does not generate plagues as Cf. FIG. 1B shows long filament-like morphology of purified Cflt phage stained with 2% phosphotungstic acid under electronic microscopy (Kuo et al., 1987).

Example 2: Purification of Replication Form (RF) and Phage DNA of Cf-Type Phages and *Xanthomonas citri* Genome DNA Preparation of the RF DNAs of Cf-type phages and their variants such as Cflt, Cflc, Cfltv, Cf16, Cf16-v1, Cf-tv2, XacF1, Cf2, Cf2 mutants and the recombinant Cf-type phages from host bacteria are performed as described (Yang and Kuo, 1984), which are each hereby incorporated by reference in their entireties. *Xanthomonas citri* subsp. *citri* is grown in 500 ml PS or LB medium at 28° C. The cells, at a density of $2 \times 10^9$ per ml, are infected with Cf-type phages at a multiplicity of 20 and treated with 170~mg/ml chloramphenicol at 10 min post-infection. Chloramphenicol is added to increase the synthesis of RF DNA and to prevent chromosomal DNA synthesis. After 4 hours of incubation at 28° C., the infected bacterial cells are harvested, chilled, washed once with 250 ml buffer (10 mM-Tris-HCl pH 8.0, 0.1 mM-EDTA) and lysed with SDS and NaOH. After lysis, the lysate is centrifuged at 44000 g-force for 90 min, and 1/30 volume of 3 M-sodium acetate and 0.6 volume isopropanol are added to the supernatant. After centrifugation at 27200 g-force for 20 min, the pellet is resuspended in 5 ml Tris-glucose (25 mM-Tris-HCl, pH 8.0, 10 mM-EDTA, 50 mM glucose) and 15 ml 5 M-potassium acetate. The bacterial DNA and debris are spun down at 27200 g-force for 20 min. The supernatant, containing the RF DNA, is precipitated with 2 volume ethanol at −20° C. for 2 to 4 hours and recovered by centrifugation at 12000 g-force for 30 min. The pellet is dissolved in 8 ml TE buffer (10 mM Tris-HCl pH 8.0, 1 mM EDTA). The DNA is then purified by centrifugation to equilibrium in a CsCl-ethidium bromide density gradient. Each Quick-Seal polyallomer centrifuge tube contained 5 ml of sample, 1.5 mg ethidium bromide and 5.05 g CsCl. Centrifugation is performed at 479000 g-force at 15 to 20° C. for 3.5 to 4 hours using a NVT-100 Beckman rotor. At the end of the run, the band containing supercoiled DNA is collected by inserting a hypodermic needle into the side of the tube. Ethidium bromide is removed by five extractions with water-saturated n-butanol. The samples are mixed with 2 volumes of distilled water and precipitated with 2.5 volumes of 100% ethanol. The DNA thus prepared is used directly for restriction endonuclease digestion or PCR. Digestion of RF DNA with restriction endonucleases, and gel electrophoresis and purification of restriction DNA fragments are performed as described in (Yang and Kuo, 1984), which is hereby incorporated by reference in its entirety.

DNAs from Cf-type phages and infected *Xanthomonas citri* subsp. *citri* are purified as described in (Kuo et al., 1987), which is herein incorporated by reference in its entirety. A purified phage suspension is dialyzed against TEN (25 mM Tris-HCl; 10 mM EDTA and 0.15 M NaCl, pH 8.5). The phage protein coat is then dissociated by adding sodium dodecyl sulfate (SDS) to a final concentration of 2%. The proteins are further digested with Pronase (1 mg/ml) at 60° C. for 18 hr or overnight. Contaminating RNA is digested by the addition of RNase A (50 μg/ml) and incubated at 37° C. for 1 hr. $NaClO_4$, is added to a final concentration of 1 M and an equal volume of PIC (TEN-saturated mixture of phenol:isoamyl alcohol:chloroform (25:1:24) was then added. This mixture is shaken thoroughly for 15 min. After 5 min centrifugation at 9000 g-force, the aqueous phase is collected and the phage DNA is precipitated with ethanol. The pelleted phage DNA is dissolved in TEN and dialyzed against two changes of TEN with 2 M NaCl, and then finally against TEN. To isolate DNA from *X. citri* cells, logarithmically growing bacterial cells at 2 to $4 \times 10^9$ cells/ml are harvested by centrifugation, washed with 5 ml of 100 mM Tris-HCl, 10 mM NaCl at pH 7.6, and suspended in 1.8 ml of 50 mM Tris-HCl (pH 7.6) 100 mM NaCl, and 5 mM disodium EDTA. The washed cell suspension is lysed by the addition of lysozyme solution (10 mg/ml in $H_2O$ 10 min at room temperature) and 0.2 ml of 20% SDS to the buffered cell suspension. The lysed cell suspension is extracted with phenol: chloroform: isoamyl alcohol (24:24: 1) until no interface could be detected between the aqueous and organic phases. The aqueous phase is precipitated with 2 volume of −80° C. ethanol. The ethanol precipitate is collected by centrifugation at 13,000 g-force for 10 min, air dried, and suspended in 2 ml of 50 mM Tris-HCl (pH 7.6) 100 mM NaCl, and 5 mM EDTA. This solution is incubated with 200 units of RNase A (New England BioLabs, Ipswich, Mass.) at room temperature for 4 hours. The RNase-treated solution is extracted three times with phenol:chloroform: isoamyl alcohol. The aqueous phase is precipitated twice with ethanol, and the dried precipitate is suspended in 10 mM Tris-HCl (pH 7.6) and 0.1 mM disodium EDTA. Digestion of Cf-type phage or host bacterial DNA with restriction endonucleases, agarose gel electrophoresis, transferring DNA to a nylon membrane and hybridization, DNA sequencing are performed in (Kuo et al., 1987; Dai, et al., 1988), which are hereby incorporated by reference in their entireties.

Figure 2A:
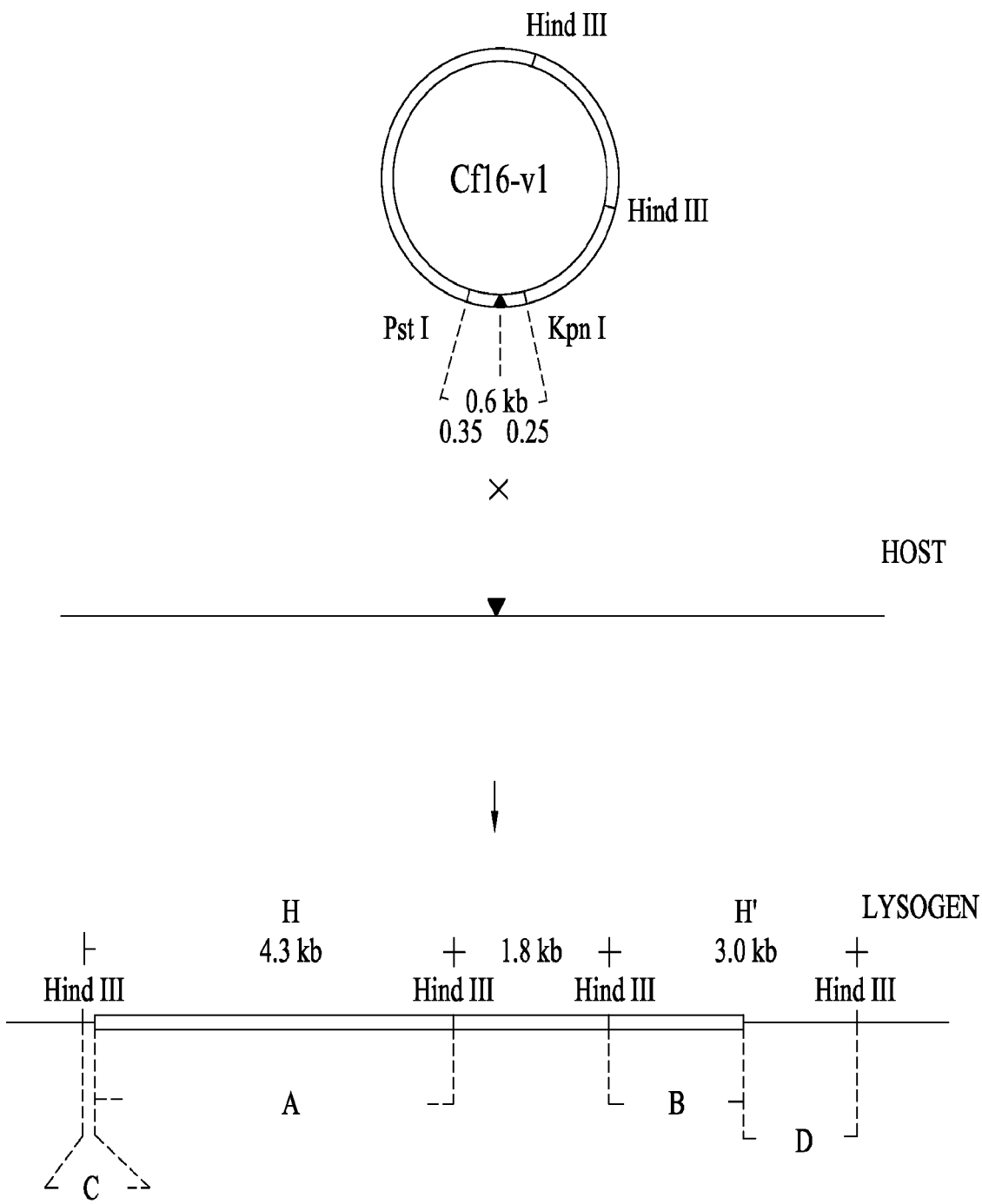
FIG. 2. (A) The Cf16-v1 attachment site was localized to the unique PstI-KpnI fragment by restriction mapping. HindIII cleaves the circular Cf16-v1 RF into two fragments of approximately 5.8 and 1.8 kb, respectively. Three lysogen HindIII fragments with a size of 1.8, 3.0 (H'), and 4.3 (H) kb, respectively, hybridize to the Cf16 probe. In the diagram, the sum of A and B should equal 5.8 kb, while the sum of C and D should equal the host HindIII fragment that contains the Cf16-v1 attachment site. The size of this fragment is calculated as H+H'−A−B=1.5 kb. Solid triangle: center of the attachment site (drawn in opposite orientation in the phage and the host chromosome). (B) Nucleotide sequence of Cf16-v1 in the vicinity of the phage attachment site (SEQ ID NO: 65). The common core sequence is underlined. Inverted repeats, potential recognition sequences for a site-specific recombination enzyme, are designated by arrows. Repeated sequences, potential binding site of another protein factor, are designated by dashed lines. Two orientations of these sequences are indicated. Sequences are numbered with bp zero assigned to the center of the 15-bp common core sequence. (C) Nucleotide sequence (SEQ ID NO: 66) of *Xanthomonas citri* subsp. *citri* in the vicinity of the Cf16-v1 attachment site. Designations used are the same as in (B) (Dai et al., 1988).
Figure 4A:
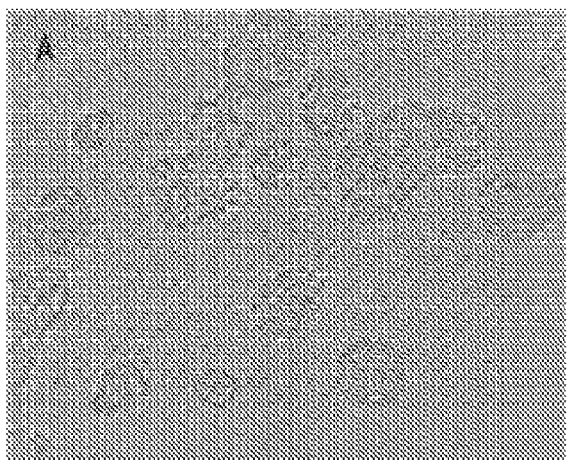
FIG. 4. Cell division of Cfltv-infected *Xanthomonas citri* cells. Using a microculture technique, cells were observed by light microscope after 16 hour incubation at 28° C., except for a few bacteria which divided slightly slower than the normal-dividing cells and would finally recover to become normal-dividing cell type. (A) Unchanged cells division, (B) infected cells (arrow) are still undivided. The respective culture contains some dividing cells, too. The respective time course of change in cell type over 12 hour incubation period is given in (C) and (D). (C) Uninfected culture, (D) cultures infected with Cfltv. ● Normal-dividing cell type, ▲ slow-dividing cell type, ○ non-dividing cell type. (Kuo, et al, 1994).
Figure 4C:
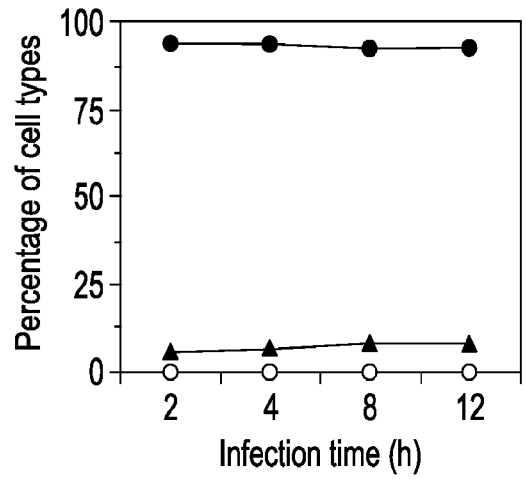
Figure 4B:
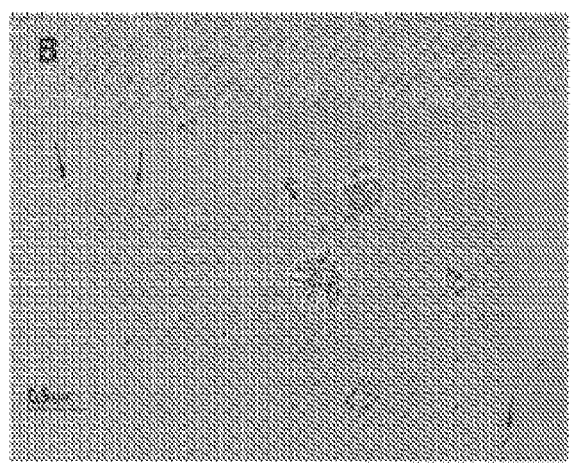
Figure 4D:
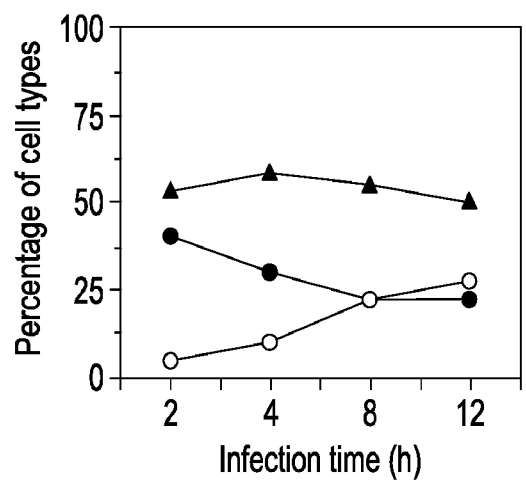

The example of Cf phage DNA integration into *Xanthomonas citri* genome is shown in FIG. 2. The Cf16-v1 attachment site is localized to the unique PstI-KpnI fragment by restriction mapping (FIG. 2A). HindIII cleaves the circular Cf16-v1 RF into two fragments of approximately 5.8 and 1.8 kb, respectively. Three lysogen HindIII fragments with a size of 1.8, 3.0 (H'), and 4.3 (H) kb, respectively, hybridize to the Cf16 probe (Dai et al., 1987). FIG. 2B shows the nucleotide sequence of Cf16-v1 in the vicinity of the phage attachment site. The common core sequence, inverted repeats, potential recognition sequences for a site-specific recombination enzyme, repeated sequences, potential binding site of another protein factor, are identified. Based on the nucleotide sequence alignment, Cf16-v1 genome is integrated within the *X. citri* host gene called (3R)-3-hydroxyacyl-[acyl-carrier-protein]:NADP+ oxidoreductase (FIG. 2C)(Dai et al., 1988). The physical map of Cf RF DNA, including the location of phage genes and cleavage sites of the restriction endonucleases, is shown in FIG. 3A. Except for ORF 165, transcription of all the investigated genes proceeds clockwise. (Cheng et al., 1999)

Example 3: Quality Control Assays for Cf-Type Phage Infection

Quality control assays for immunity, phage infectivity, phage yield, and viable colonies after Cf-type phage infection are performed as described in (Kuo et al., 1987), which are hereby incorporated by reference in their entireties. Samples taken from the culture are spread onto LB agar plates. After colony formation, a single colony is chosen and transferred to LB broth for 24 hours at 30° C. For assay of immunity a sample from this culture is mixed with broth soft agar and poured onto an LB plate. Cf phage suspension (0.01 ml) is spotted onto the layer containing bacteria to be tested. Sensitive cells formed a clear zone and immune cells did not. For determination of phage infectivity and phage yield the sample from the above culture is centrifuged at 10,000 g-force for 20 min to remove cell debris. The 0.01 ml samples from dilutions of the supernatant are plated with sensitive bacteria. The viable colony count is made by spreading the cells on LB plates and incubation at 28° C. for 3 days.

The growth curve for bacteria after Cf-type phage infection is determined as the following (Kuo et al., 1987) which is herein incorporated by reference in its entirety. Infected bacteria are suspended in LB at a concentration of $1\times10^8$ cells/ml and incubated at 30° C., with shaking. At different intervals, samples are diluted and spread on LB agar plates. After colony formation the number of colonies is counted.

The methods of preparation of Cf-type phage infection culture and microculture technique are performed as the following (Kuo et al., 1994), which is herein incorporated by reference in its entirety. TSG liquid medium contains 5 g NaCl, 5 g bacto-soytone, 10 g bacto-tryptone and 2 g glucose per liter. To produce solid media for colony formation assay or for microculture, 1.5% or 0.75% agar respectively are added. Kanamycin is used at 100 mg/ml. A single colony of host bacteria is transferred into 5 ml TSG liquid medium and grown at 28° C. with shaking. After reaching its log phase, the concentration of bacteria is about $5\times10^8$ cfu/ml, and the phage at MOI of 10 are added. The infected cultures are grown for the time required for each experiment. Bacteria at a concentration of $5\times10^8$ cfu/ml are infected with Cf-type phages or their variants at MOI of 10. At different time intervals, samples are taken and spread on TSG agar plates previously poured on concave slides. The slides are placed in petri dishes and incubated at 28° C. for 16 hours. Extent of cell division is examined with a light microscope. At this stage the uninfected cells have already divided into about 32 cells. The respective cell types are determined and calculated as percent of total population.

Assays for surviving host *Xanthomonas citri* cells, Cf-type phage-resistant, Cf-type phage-releasing and Cf-type phage-containing cells, are performed as described with modification (Kuo et al., 1994), which is herein incorporated by reference in its entirety. Host bacteria are infected with phage, and samples are spread on TSG agar plates. The number and size of colonies formed is determined directly and used to calculate the respective percentage. In order to determine the cell types of these colonies they are transferred onto two different agar plates by replica plating. One plate is seeded with Cf-type phage or their variants ($10^9$ pfu per plate) for detection of phage-resistant cells. The other plate is seeded with sensitive bacteria to detect lysis by phage-releasing cells. The lysogen should grow to unchanged colonies on the first plate, and release phage and form plaques on the second plate.

Figure 15:
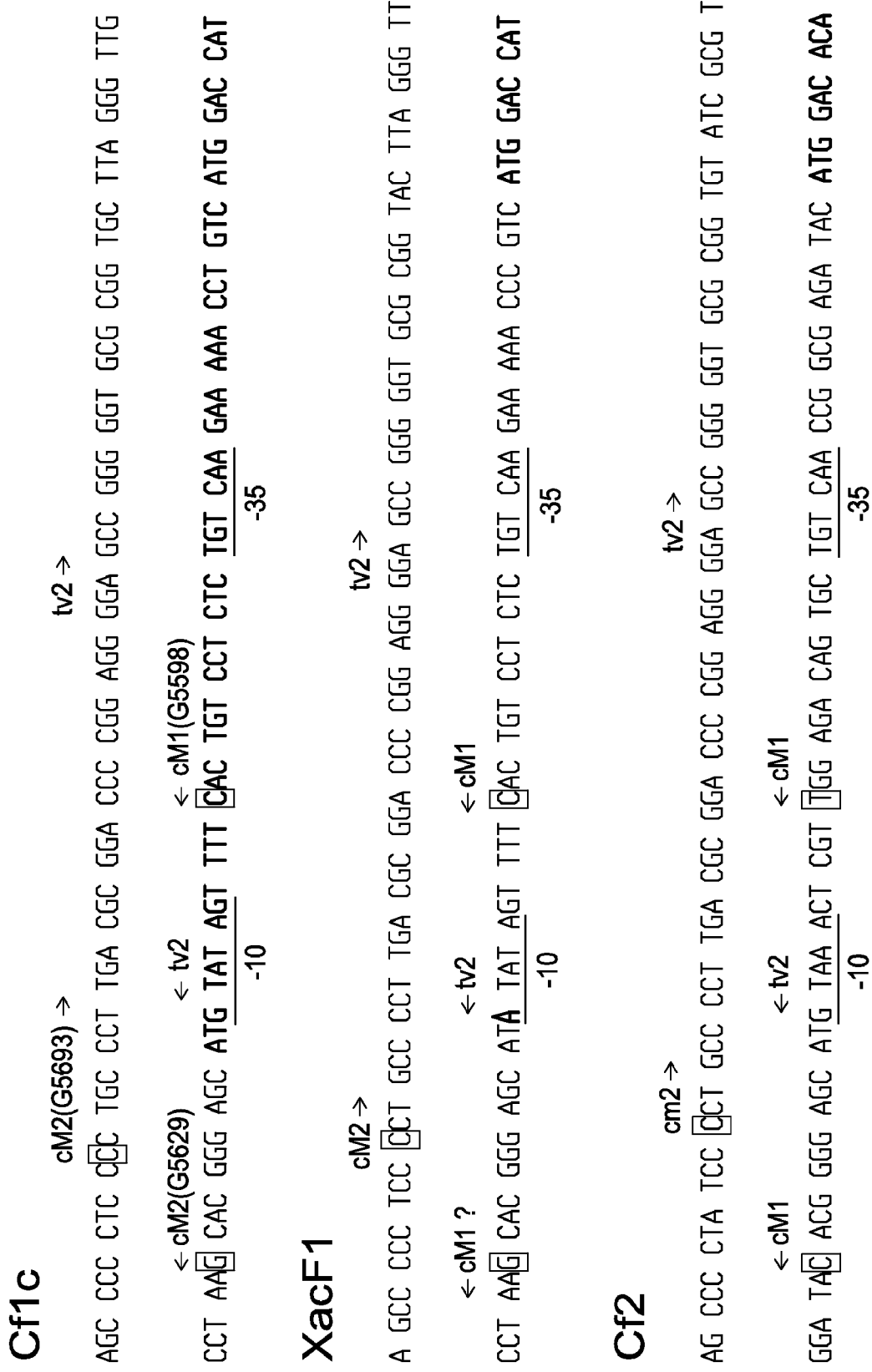
FIG. 15. The determinant sequences of phage immunity in Cf1c (SEQ ID NO: 87), XacF1 (SEQ ID NO: 88), and Cf2 phage (SEQ ID NO: 89). The ORF165 is shown in boldface type. The −35 and −10 consensus sequences of a predicted promoter region are underlined. The boxes indicate the transcriptional start sites of cM1 and cM2. The boundary of the 49 base pair deletion of Cf-tv2 is shown by the arrows. The A in the −10 TATA box represents the mutation of the single base G to A substitution in the virulent Cf variant XacF1. The 58-nucleotide sequence in Cf2 genome with 95% homology with Cf is located upstream of G labeled in italic.
Figure 16:
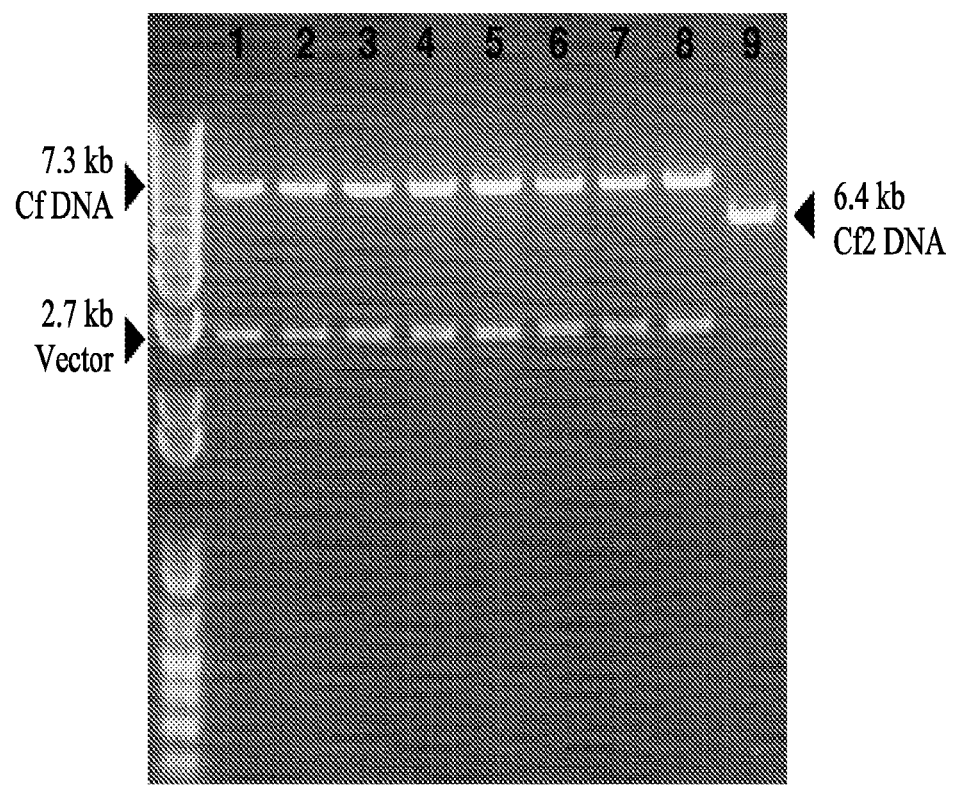
FIG. 16. Agarose gel electrophoresis of Cf and Cf2 phage DNA. Synthetic DNA fragments of full-length 7.3 kb genomic DNA of Cf phage (lane 1-8) were ligated and subcloned into a kanamycin-resistant plasmid vector. Plasmids were digested with EcoRI and analysed in 1% TAE agarose gel. Synthetic DNA fragments of full-length 6.4 kb genomic DNA of Cf2 phage (lane 9).

An example is shown that cell division of Cfltv-infected *Xanthomonas citri* cells was monitored using a microculture technique (FIG. 4). Bacterial cells were observed by light microscope after 16 hour incubation at 28° C. The normal cells divided and grew into separate colonies. Cfltv-infected cells were still undivided. (Kuo et al., 1994)

Example 4. Electroporation of Cf Phage DNA into *Xanthomonas citri* Bacteria, RNA Extraction, and Primer Extension Cf-type phages and their variant DNAs are either purified by isolating phage particles as described in Example 2, or are directly synthesized by a company (GenScript, Coralville, Iowa). The synthesized DNA fragments are ligated and subcloned into a kanamycin-resistant pUC57 vector and amplified in *E. coli*. An example is shown that the synthesized 7.3 kb Cf1-tv2 DNA fragments are subcloned into pUC57 vector, digested with restriction enzymes and analyzed in 1% agarose gel. (FIG. 16).

The electroporation method to transform phage or RF DNAs of Cf-type phages and their variants into *Xanthomonas citri* subsp. *citri* cells is performed as the following (Yang et al., 1991), which is herein incorporated by reference in its entirety. Bacterial cells are grown for 16 hour and chilled, sedimented and resuspended in 0.5 volume of the buffer (200 mM Tris-HCl; 1 mM EDTA and 1 M NaCl, pH 7.5). After even mixing and centrifugation, bacterial pellets are washed and resuspended at TMN buffer (50 mM Tris-HCl; 50 mM $MgSO_4$ and 80 mM NaCl, pH 7.5) on ice for 2 hours. Pellets from centrifugation separation are then washed and resuspended in deionized water to remove ion. 1 to 2 micro g RF DNA of Cf-type phages in 5 ml deionized water was added to 40 □1 bacterial suspension. After even mixing, the mixture was poured into a precooled cuvette (VWR, Radnor, Pa.) and subjected to appropriate pulse at 12.5 kV/cm, 25□ micro F, 400 QZ for 7 to 9.3 mini-seconds.

RNA isolation and Northern hybridization is performed as described previously (Cheng et al., 1999), which is herein incorporated by reference in its entirety. Primer extension experiments are carried out using the method described by (Cheng et al., 1999). Synthetic oligonucleotides for cM1 (5'-CAGGATCGAATATGGATGCACGGTGTA-3') (SEQ ID NO: 69) and cM2 (5'-TGACAGAGAGGACAGTGAAAACTATAC-3') (SEQ ID NO: 70) complementary to the sequence position 5701-5728 and 5475-5502 (FIG. 5), respectively, are used for both primer extension reaction and DNA sequencing.

Electroporation of *X. citri* cells yields frequency as high as $5.2\times10^9$ pfu per microgram of DNA. Both RF DNA and the single-stranded phage DNA were efficiently accepted by *X. citri* cells in the same condition (Yang et al., 1991).

Mutation sites on the cf-tv2 and Cfltv (also called cf-tv1) mutation on the Cf genome are shown in FIG. 3B. The 49 base pair deletion of cf-tv2 is upstream of ORF 165, which contains the attachment site (attP) for integration in the phage. The T in the start codon of ORF165 is mutated of the single base substitution in Cfltv. Using primer extension to detect the transcription start sites, there are two transcripts, cM1 and cM2, generated from ORF165 region at opposite directions. The 5' end of the cM1 transcript is located at G5629, while the 5' end of the cM2 transcript is at C5693 (FIG. 5A). There are −35 and −10 consensus sequences of a predicted promoter region identified in the upstream sequence of ORF165 (Cheng et al., 1999).

Example 5. Generation and Application of Cf-Type Phages that can Inhibit *X. citri* Growth and Suppress Citrus Canker Disease Analysis of DNA sequence and organization reveals the superinfection activity of Cf1tv and Cf-tv2 is mapped at the upstream sequence of ORF165 that contains a predicted promoter region encoding cM1 and cM2 transcripts (FIG. 3, FIG. 5B, FIG. 15) (Cheng et al., 1999). Cf-tv2 has 49 base-pair deletion at upstream of ORF 165, whereas Cfltv has T to A substitution in the start codon of ORF165. This T is also located next to −10 consensus TATA box of a predicted promoter for cM1 transcript (FIG. 5B). In addition, the virulent Cf variant XacF1 also contains G to A substitution at this −10 TATA box (FIG. 15). These results demonstrate that this predicted promoter is the determinant for phage immunity.

Cf2 and Cf phage shares almost no sequence homology in their entire genome except the starting 58 nucleotides of cM2 transcript of Cf is 95% identical to Cf2. The −35 and −10 consensus sequences are also found in the upstream of ORF162 in Cf2 (FIG. 15), indicating that the critical domain for phage immunity is also conserved in Cf2. These findings suggest that Cf2 can be also engineered into a virulent variant as a bio-control reagent against citrus canker pathogen.

This invention claims the applications of Cf-type phages, such as Cf, Cf1c, Cf-tv1, Cf-tv2, XacF1, Cf2 and their mutants "Cf-M" to inhibit *X. citri* growth in an orange grove.

(1) "Cf-M" phage is generated by serial passages or artificially induced mutations within the sequence of Cf-type phage genomes (SEQ ID NO:1, 24, 25), where one or more nucleotides are added, deleted, or substituted. Artificially induced mutations are conducted by treating Cf, Cf1c, Cf-tv1, Cf-tv2, XacF1, Cf2 phages with mutagens such as, but not limited to, ethyl methanesulfonate and sodium nitrite, as described (Sega, 1984; U.S. Pat. No. 3,052,606 A; 9/1962), (FIG. 6A), which are herein incorporated by reference in their entireties.

(2) Cf, Cf1c, Cf-tv1, Cf-tv2, XacF1, Cf2 and Cf-M phages are propagated and purified as Example 1 and 2. Phage infectivity assay is performed as the following. One milliliter of *X. citri* culture is centrifuged, and the supernatant is filtered through a 0.45-micro meter-pore-size filter to remove any residual bacteria. The filtrate is serially diluted in LB medium, and 10 ml of each dilution is mixed with 100 ml of mid-log-phase culture of *X. citri* and 3 ml of soft agar (0.75%) in LB broth. The mixture is poured and spread evenly onto an agar plate. The plate is scored for plaque formation after incubation at 28° C. for 18 hours. Quality controls of these different Cf-type or Cf-M phages are assayed as Example 3, and the individual clones that yield the highest inhibitory efficiency on the bacterial growth will be selected for further application in the field. Phage particles are aliquoted (herein called "phage stock") and stored in distill water or a proper buffer at 4° C.

(3) Field tests of susceptible citrus varieties with these Cf-type or Cf-M phages are performed to compare the disease severity caused by the citrus bacterial canker in one-quartre acre (0.1 ha) for each treatment. A phage stock is diluted into water or a solution in a proper ratio, and sprayed or misted to coat on the citrus trees and/or fruits once a week for 5 times. After the phage treatment, the leaf and fruit bacterial canker infested rates of different citrus varieties are investigated. Different Cf and variants phages are screened for the control of *X. citri* subsp. *citri* with better pathogen inhibition effect than others. Cf-type or Cf-M phages with the greatest inhibitory effects on citrus canker in field tests are selected for the large-scale production and commercial use. The detailed process flowchart is further described in FIG. 6C.

Figure 6:
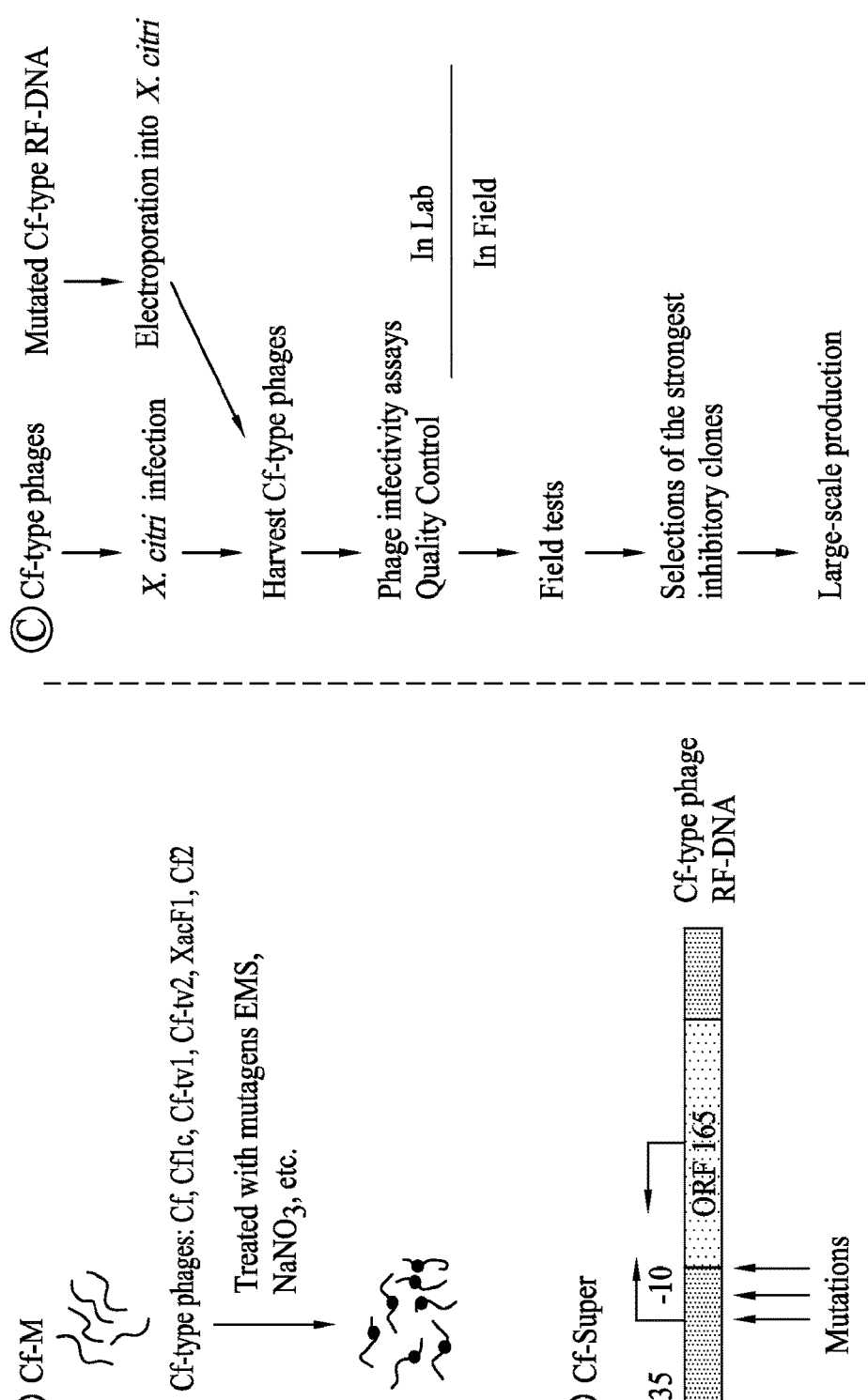

(4) This application also claims an application of using a recombinant Cf-type phages (herein called "Cf-Super" phages), which can superinfect and kill "immunued" *X. citri* bacteria, to treat citrus canker disease. To generate Cf-Super phages, a series of mutations are generated to mutate nearby or within the sequence of ORF165 to change the determinant domain of phage immunity (SEQ ID NO:1, 2, 24, 25), where one or more nucleotides are added, deleted, or substituted, in RF DNAs of Cf-type phages and their variants (FIG. 6B, 15). These recombinant RF DNAs will be electroporated into *X. citri* cells as Example 4. Cf-Super phages are propagated in cells and released into the LB medium. Cf-Super phage particles are harvested and purified from LB medium as Example 1. Phage infectivity assay, quality control, and application in the field are performed as described as (2) and (3). Cf-Super phages with the greatest inhibitory effects on citrus canker symptoms in field tests will be selected for the commercial use. Cf-Super phages cause the lysis of *X. citri*, and new phages are released to infect more bacteria in a lesion of citrus canker. The detailed process is described in FIG. 6C.

Figure 7:
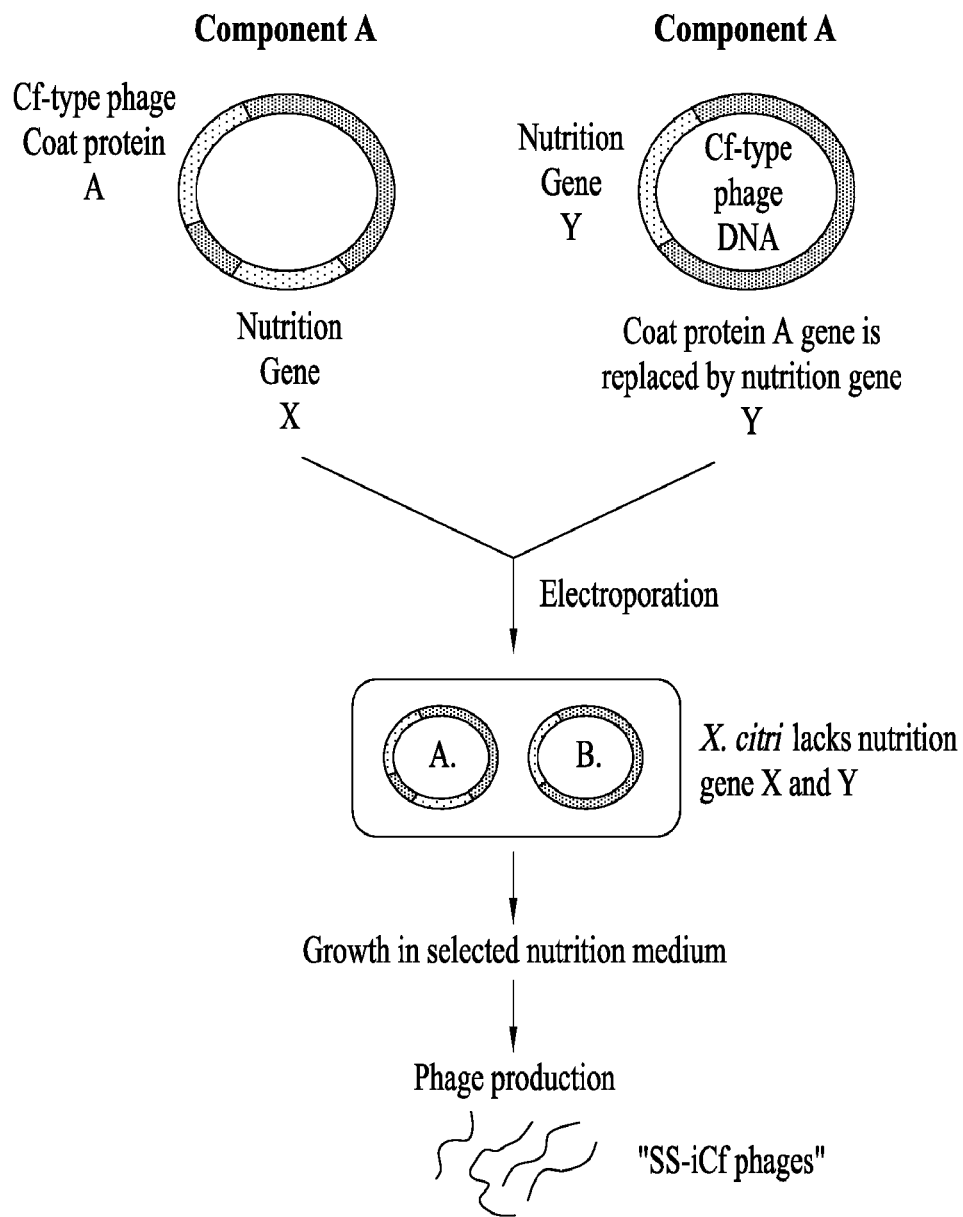

Example 6. Generation and Application of a Controllable "SS-iCf" Phage that Only Infect and Kill *X. citri* Bacteria Once but Will not Spread and Replicate after Used This invention claims the applications of a method that generates recombinant "SS-iCf" phages which infectivity is controllable by performing the following steps (FIG. 7):

(1) *Escherichia coli* or *X. citri* bacteria mutants (herein called "bacteria mutants") that are insufficient to grow in a selected nutrition medium (e.g., a medium lack of specific amino acids or essential components) is prepared by removing essential nutrition genes via the site-directed gene replacement mutagenesis (Oshiro et al, 2006).

(2) "Component A": A plasmid containing DNA fragments encoding Cf-type phage coat protein A, a protein having the amino acid sequence of SEQ ID NO: 5, 32, 44, or proteins having the same amino acid sequences where one or more amino acids are added, deleted, or substituted amino acids, is cloned in a broad-host-range expression DNA vector (e.g., pUC8, pRK415, pRKD418 etc.) (Mather et al., 1995). This DNA vector also contains an essential nutrition gene X that can compensate nutrition deficiency of bacteria mutants as described in (1). These DNAs (herein called "component A") are electroporated into *Escherichia coli* or *X. citri* bacteria mutants as Example 4, grown in a selected nutrition medium, and purified as Example 2.

(3) "Component B": A DNA fragment of an essential nutrition gene Y (different gene from component A) is amplified by polymerase chain reaction (PCR), and subcloned into RF DNA of Cf-type phages to replace the coat protein A gene of Cf-type phages, variants, or Cf-Super phages. These recombinant RF DNAs containing a nutrition gene Y (called "component B") are electroporated into *X. citri* cells bacteria mutants and grown in a selected nutrition medium. Component B is then purified as Cf RF DNA in Example 2. Due to the loss of the essential coat protein A gene, component B alone cannot produce infectious phage particles.

(4) To generate a controllable, "single-shot infectious" Cf-type (herein called "SS-iCf") phage, Component A and B will be electroporated together into *X. citri* mutants lack of nutrition genes X and Y, then bacteria are grown in a selected nutrition medium at 28° C. SS-iCf phage particles are harvested and purified from growth medium as Example 1. The detailed strategy is further illustrated in FIG. 7. Phage infectivity assay is performed as Example 5. The individual clones that yield the highest inhibitory efficiency on the bacterial growth but do not infect bacteria for the second time will be selected for further application in the field. Phage stocks are aliquoted and stored in distilled water or a proper buffer at 4° C. Field tests are performed as Example 5, and the greatest inhibitory phage clones will be selected for further application of commercial use. SS-iCf phages can infect and kill *X. citri* cells by the lysis of bacterial cells. Because the genome of SS-iCf phages do not contain the coat protein A gene, it cannot propagate in the filed anymore and can only be used for one time.

Example 7: Methods to Improve the Storage Shelf Life of Cf-Type Phages

Figure 8:
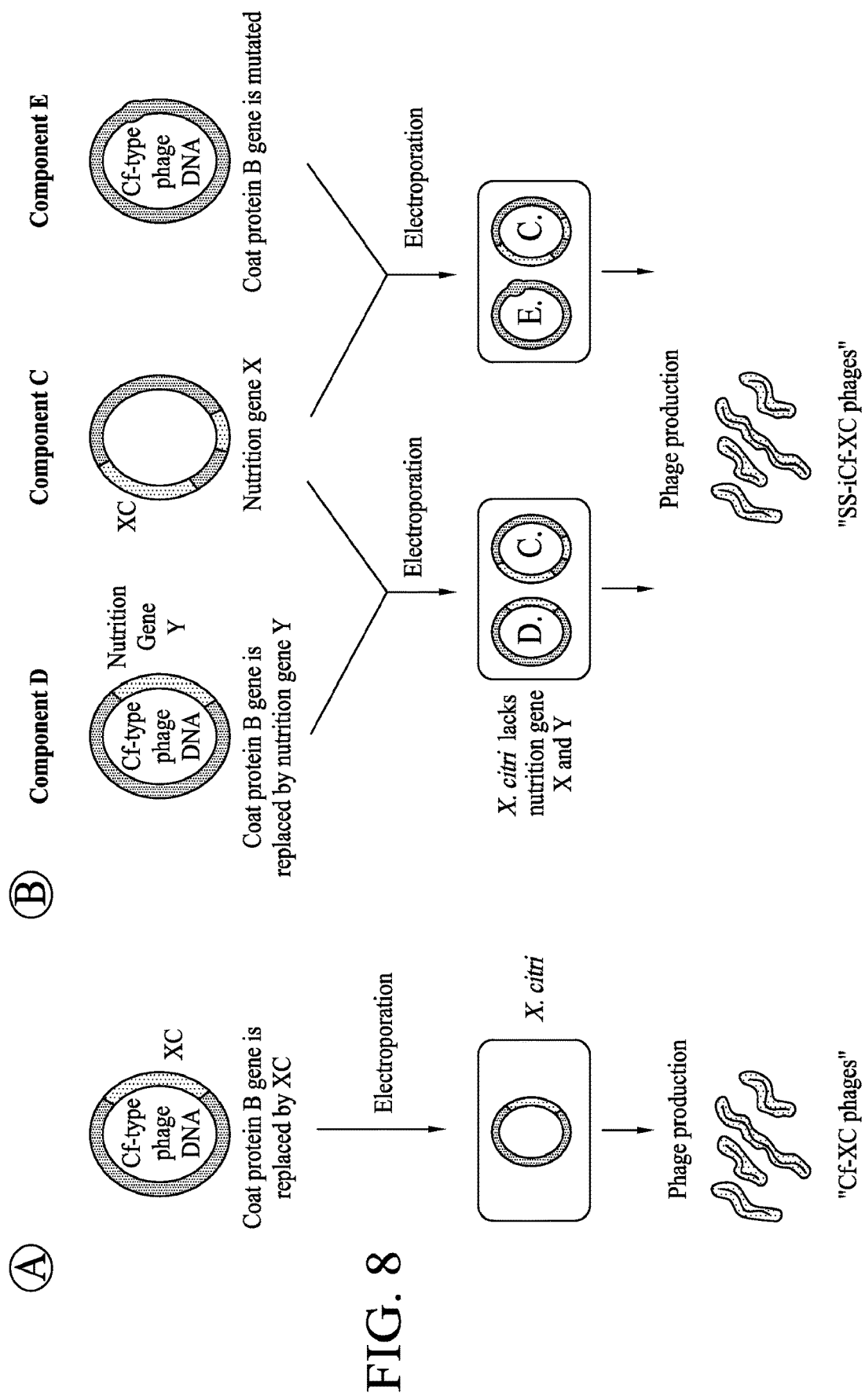

This invention claims a method to apply and engineer a recombinant Cf-type phage to increase its shelf life for storage purpose. These recombinant Cf-type phages are packed with the major coat protein B from other filamentous Inoviridae phages which has more stable biochemical properties (herein called "Cf-XC phages") as the following steps (FIG. 8):

(1) The DNA fragments (herein called "XC DNA fragments") are nucleotides encoding a protein (coat protein B) having the amino acid sequence of SEQ ID NO: 13 to 22 (such as, but not limited to, an example of SEQ ID NO: 23 from phiLf phage), or proteins having the same amino acid sequences where one or more amino acids are added, deleted, or substituted amino acids.

(2) These XC DNA fragments are amplified with PCR and cloned into RF DNAs of Cf-type phages, their variants, Cf-M, Cf-Super, and SS-iCf phages to replace the major coat protein B gene of Cf-type phages. These RF DNAs containing XC fragments are electroporated into *X. citri* bacteria, amplified and purified as Cf RF DNA as Example 2. The Cf-XC phage particles from the growth medium are also harvested and purified as Example 1. The detailed strategy is further illustrated in FIG. 8A. Phage infectivity assay and the application of Cf-XC phage particles in the field tests are the same as Example 5, and the greatest inhibitory phage clones will be selected for further application. Cf-XC phages cause the lysis of *X. citri*, and new Cf-XC phages are released to infect more bacteria in a lesion of citrus canker.

To generate a controllable, "single-shot" infectious Cf-XC phages (herein called "SS-iCf-XC phages"), the procedure is performed as following (FIG. 8B):

(3) Component C: XC DNA fragments are cloned in a broad-host-range expression DNA vector that also contains an essential nutrition gene X. These plasmid DNAs (herein called "component C") are transformed into *Escherichia coli* or *X. citri* bacteria mutants, grown in a selected nutrition medium, and purified.

(4a) Component D: A DNA fragment of a nutrition gene Y is amplified by PCR and subcloned into RF DNA to replace the major coat protein B gene of Cf-type phages and their variants, Cf-Super, and SS-iCf phages. These recombinant RF DNAs (herein called "component D") will be electroporated into *X. citri* bacteria mutants as described in Example 4. Cells are able to grown on a selected nutrition medium, and component D is purified as Cf RF DNA as described in Example 2.

(4b) Component E: A site-specific insertion with two nucleotides is introduced into the nucleotide position corresponded to the first codon in the ORF of major coat protein B in RF DNAs of Cf-type phage and their variants (e.g., between nucleotide 313 and 314 of SEQ ID NO: 1; nucleotide 3817 and 3818 of SEQ ID NO: 25) using PCR. This insertion causes Cf-type RF DNAs unable to encode major coat protein B. These recombinant RF DNAs (herein called "component E") are electroporated into *X. citri* cells as described in Example 4, and component E is purified as Cf RF DNA as described in Example 2. Due to the loss of the major coat protein B gene, component D or E alone cannot produce any phage particles.

(5) The mixture of "Component C and D", or "component C and E", is electroporated into *X. citri* bacteria mutants lack of nutrition genes X and Y, respectively, then cells are grown in a selected nutrition medium at 28° C. SS-iCf-XC phage particles are harvested from the medium as described in Example 1. The detailed strategy is further illustrated in FIG. 8B. Phage infectivity assay and the application of SS-iCf-XC phage particles in the field tests are the same as Example 6. Because the genome of SS-iCf-XC phages do not contain the coat protein B gene, these recombinant phages cannot produce new phage particles in the filed anymore and can only be used for one time.

An alternative way to generate SS-iCf-XC phages is also claimed in this patent. Component B in Example 6 is used instead of Cf-type RF DNAs for cloning in step (2), (4a) and (4b) to generate "component F", "component G", and "component H", respectively. Component F, G, or H cannot generate phage particles because they do not have coat protein gene A and B. The DNA mixtures of "Component A+F"; "component A+C+G" and "component A+C+H" will be electroporated into *X. citri* bacteria lack of nutrition genes X and Y. Cells are grown in a selected nutrition medium at 28° C. SS-iCf-XC phage particles will be harvested from growth medium. Phage infectivity assay and the selection and application of SS-iCf-XC phage particles in the field tests for commercial use are the same as Example 6.

Figure 9:
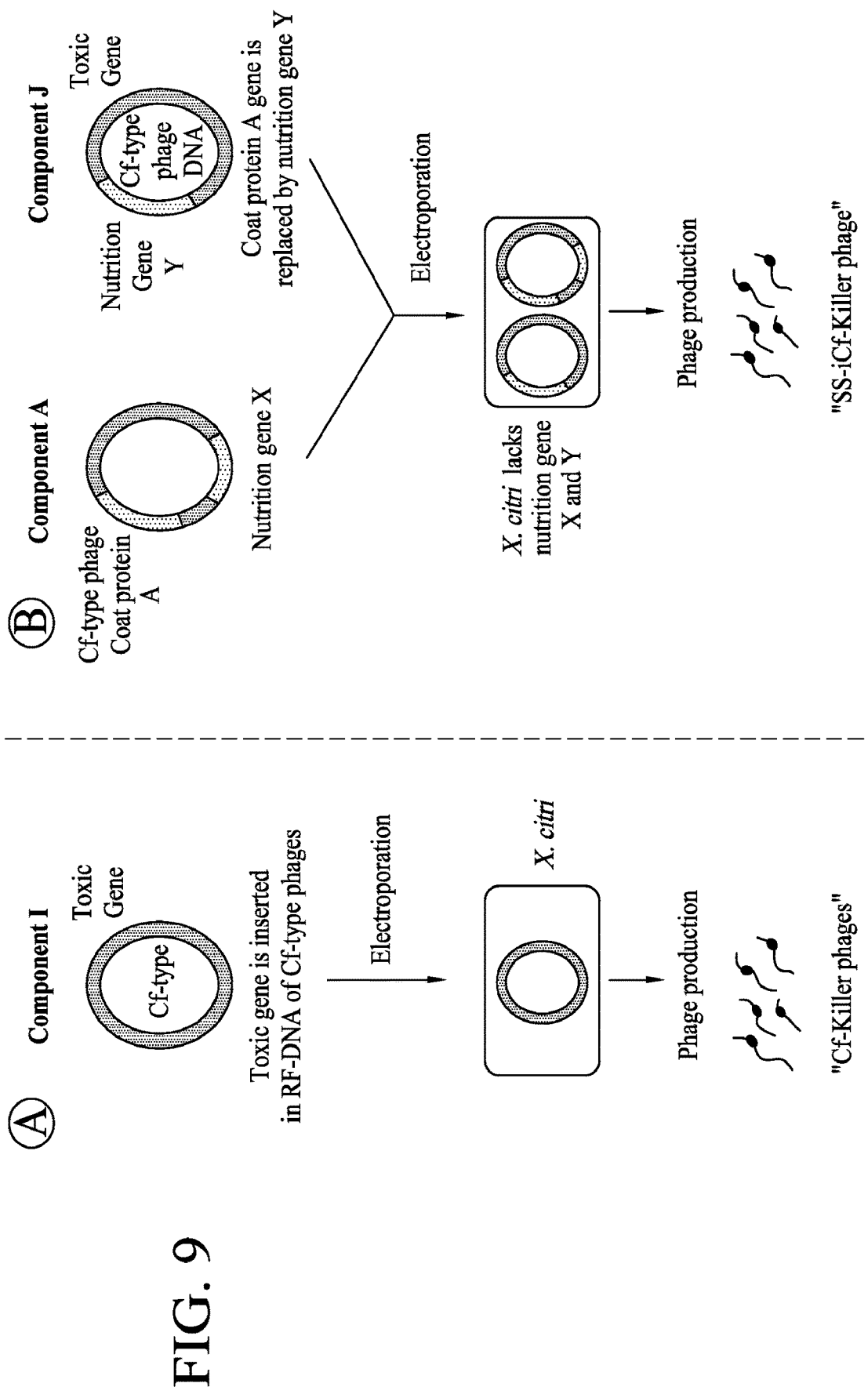

Example 8: Generation and Application of "Cf-Killer" Phages to Carry Genes Causing the Lysis of Bacterial Cells This invention claims a method to generate a recombinant Cf-type phage (here called "Cf-killer phage") that contains toxic genes to kill or inhibit *X. citri* bacteria growth. Gene materials (such as DNA fragments) that encode nucleic acids or amino acid products (such as, but not limited to, lysozyme from chicken egg white) able to interfere with bacterial growth or lead to bacterial cell lysis are cloned into RF DNAs of Cf-type phages, their variants, and recombinant Cf-type phages described in Example 5, 6 and 7. These recombinant RF DNAs (herein called "component I") will be electroporated into *X. citri* cells as described in Example 4, Cf-killer phage particles are harvested from growth medium as described in Example 1. The detailed strategy is further illustrated in FIG. 9A. Phage infectivity assay and the application of Cf-killer phage particles in the field are the same as Example 5. Cf-killer phages cause the lysis of *X. citri*, and new Cf-XC phages are released to infect more bacteria in a lesion of citrus canker.

To generate a controllable or "single shot" infectious Cf-killer phage (herein called "SS-iCf-killer phage"), the DNA fragments, which encode nucleic or amino acid products to interfere with bacterial growth or lead to bacterial cell lysis, are cloned into component B (herein called "component J"). Due to the loss of the essential coat protein A gene, component J alone cannot produce infectious phage particles. The DNA mixture of component A and I will be electroporated together into *X. citri* bacteria mutants, then cells are grown in a selected nutrition medium at 28° C. SS-iCf-killer phage particles are harvested from growth medium as described in Example 1. Phage infectivity assay and the application of SS-iCf-killer phage particles in the field are the same as Example 6. Because the genome of SS-iCf-killer phages do not contain the coat protein A gene, these phages cannot produce new infectious phages in the filed anymore and can only be used for one time. The detailed strategy is further illustrated in FIG. 9B.

Figure 10:
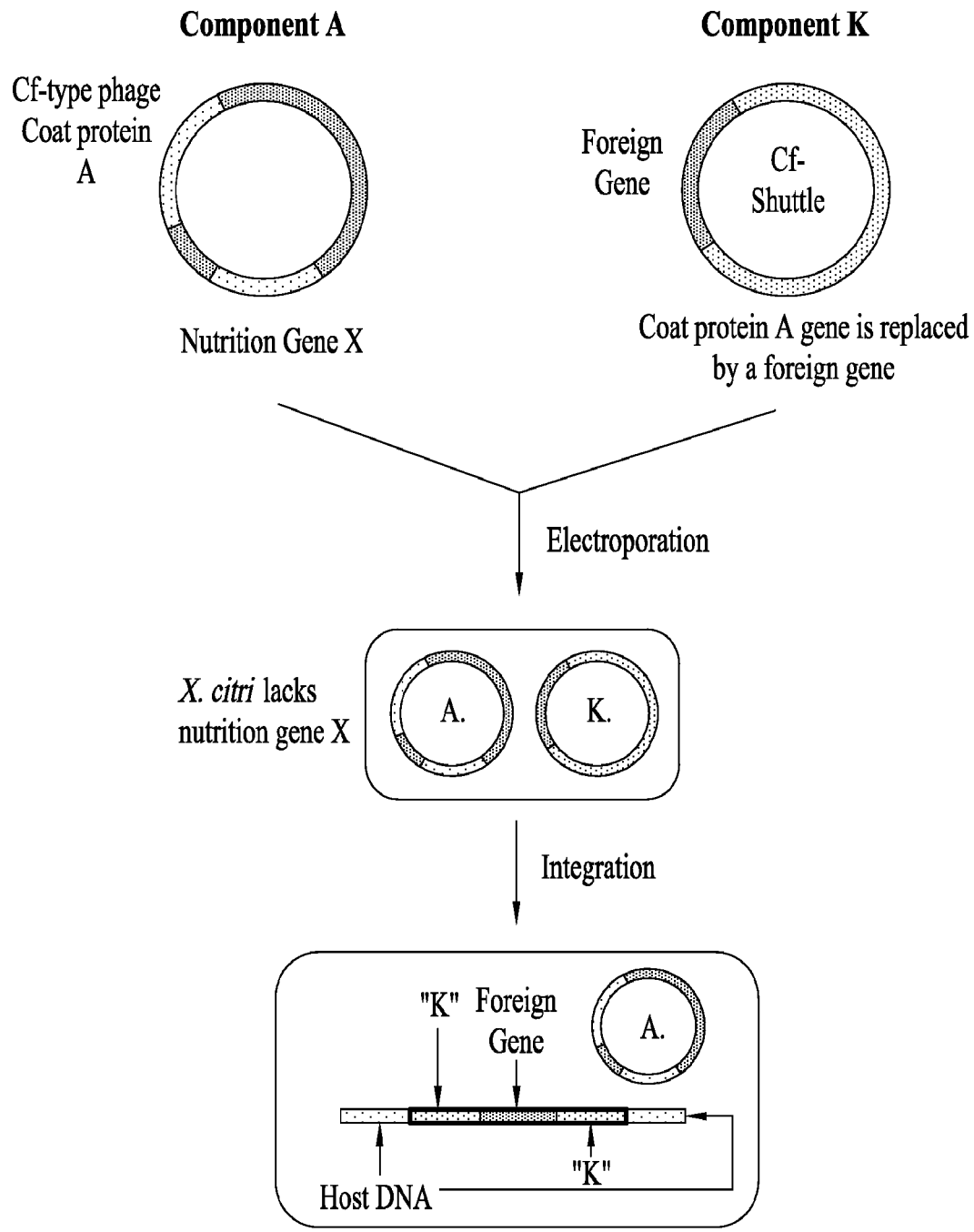

Example 9. Generation and Application of "Cf-Shuttle" Phage as a Vector to Carry Foreign Genes that Integrate into *X. citri* Genome This invention claims that a method to generate a vector (herein called "Cf-Shuttle") to deliver foreign genes that can integrate into *X. citri* genome (FIG. 10). The DNA fragments, which encode nucleic acid or amino acid products are cloned to replace coat A gene in RF DNA of Cf-type phages (herein called "Component K"). The mixture of Component K and component A are electroporated together into *X. citri* mutants as described in Example 4. Cells are grown in a selected nutrition medium at 28° C. Cf-shuttle vector phage particles are harvested from growth medium as described in Example 1. The rate of integration of Cf shuttle vector into *X. citri* genome is assayed as Example 2 and 4. The detailed strategy is illustrated in FIG. 10.

Example 10. Purification, Engineering and Application of Xp12 Phage to Inhibit Rice Blight Disease in the Field This application claims methods to generate Xp12 phage as a bio-control tool that inhibit rice blight disease in the field. Xp12 phage (ATCC 27931-B1) and its host *Xanthomonas oryzae* are purchased from ATCC. Bacteria are routinely grown at 28° C. in TSG medium as described in Example 1. Phage infection is normally performed by adding CsCl-purified phages to the bacterial culture in early exponential phase (an OD600 value of 0.3-0.4) at a MOI of about 10.

(1) Phage genome DNA is isolated and purified from CsCl-purified Xp12 phage by phenol-chloroform extraction and precipitation with 100% ethanol. Purified DNA is digested with restriction enzymes KpnI, DpnI, EcoRV, and NdeI, and cloned into pBlueScript II vector (Agilent Technologies) for DNA sequencing. Mutations of phage DNA where one or more nucleotides or genes are added, deleted, or substituted are cloned using PCR or generated by treatment with ethyl methanesulfonate or sodium nitrite. These chemical-mutated or recombinant Xp12 phage DNAs (called "Xp12 variants") are electroporated into *X. oryzae* bacteria, and Xp12 variant phage particles are harvested and purified from growth medium as Example 1. Phage infectivity assay are performed as Example 5. The individual clones that yield the highest inhibitory efficiency on the bacterial growth will be selected for the field test as described below.

(2) Phage stocks are aliquoted and stored in 10 mM Tris, 50 mM $CaCl_2$, pH 8.0 (Tris-$CaCl_2$ buffer) at room temperature or 4° C. In a rice field, a phage stock is diluted in Tris-$CaCl_2$ buffer, and field tests are performed as the following:

(a) Detached leaf assay: To determine the virulence and relative aggressiveness, the suspensions of different isolates of *Xanthomans oryzae* from ATCC obtained from the different rice zones were applied on leaves of eight rice varieties. The detached leaves were placed on 3-folded blotting paper towel in petri plates and inoculated with bacterial suspension containing $10^8$ cfu/ml through pin prick method. The inoculated leaves were incubated at 22° C., the lesion length measured in cm and data analyzed statistically by ANOVA and significance at 5% level was tested by Duncan's multiple range test (DMRT).

(b) Glass house assay: In glass house experiment seeds of various rice varieties were grown on moist sterilized filter paper in Petri plates, maintained in a growth chamber at 30-35° C. Two weeks old seedlings were transplanted to small plastic pots (diameter 13 cm) and placed in glass house at pre-tillering stage. The plants were again transplanted to bigger plastic pots (diameter 27 cm) and three leaves per isolate were inoculated using clipping method. The control was treated simply with sterilized Tris-$CaCl_2$ buffer. The lesion size was measured after 12-14 days.

(c) Field assay: Field trials for testing pathogenicity/virulence of different isolates of *X. oryzae* were conducted at fields. For nursery raising the seeds of rice variety were soaked (100 g/$m^2$) overnight and sown during the first week of June. The seeds were spread on seed bed covered with dried plant material (wheat or rice straw) and kept moist by adding water. After one month (in the first week of July) the seedlings were removed from the nursery and transplanted in the field.

(d) Inoculation/treatment: Sixty to seventy days old rice plants were inoculated with Xp12 phages or recombinant variants, together with various isolates of *X. oryzae*, using clipping method of inoculation. The lesion size was measured after 12-14 days.

Figure 11:
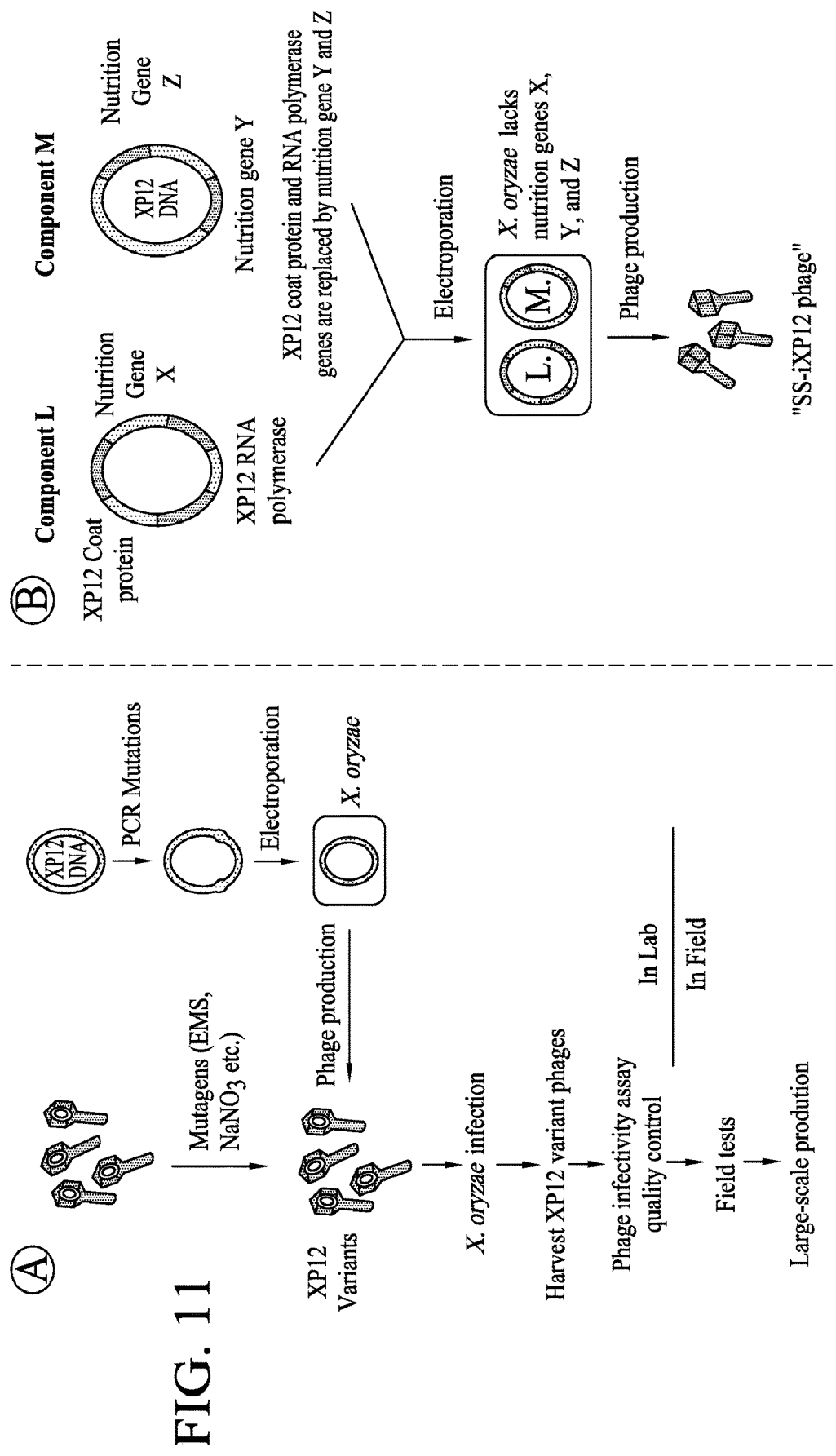

Xp12 phages and variants with the greatest inhibitory effects on *X. oryzae* growth are selected based on the field test results for the further application and commercial use. Xp12 variant phages cause the lysis of *X. oryzae*, and new Xp12 variant phages are released to infect more bacteria in the rice field. The detailed strategy and process flowchart is further illustrated in FIG. 11A.

Example 11. Generation and Application of a Controllable "SS-iXp12" Phage that Only Infect and Kill *X. oryzae* Bacteria Once but Will not Spread and Replicate after Use To generate the controllable, "single-shot infectious" Xp12 phage (herein called "SS-iXp12" phage), the procedures are described as the following (FIG. 11B):

(1) *Escherichia coli* or *X. oryzae* bacteria mutants that are insufficient to grow in a selected nutrition medium (e.g., a medium lack of specific amino acids or essential components) is prepared by removing essential nutrition genes via the site-directed gene replacement mutagenesis.

(2) "Component L": A plasmid containing DNA fragments encoding coat protein and/or RNA polymerase genes of Xp12 phage, or proteins having the same amino acid sequences where one or more amino acids are added, deleted, or substituted amino acids, was cloned in a broad-host-range expression DNA vector. This DNA vector contains an essential nutrition gene X that can compensate nutrition deficiency of bacteria mutants as described in (1). These DNAs (herein called "component L") are electroporated into *Escherichia coli* or *X. oryzae* bacteria mutants as Example 4, grown in a selected nutrition medium, and DNAs are purified as Example 2.

(3) "Component M": A DNA fragment of two essential nutrition genes Y and Z (different gene from component L) is amplified by polymerase chain reaction (PCR), and subcloned into Xp12 DNA to replace the coat protein and RNA polymerase gene of Xp12 phages or Xp12 variants in Example 10. These recombinant Xp12 DNAs containing nutrition genes (called "component M") are electroporated into *X. oryzae* bacteria mutants and grown in a selected nutrition medium. Component M is then purified as described in Example 2.

Due to the loss of the essential coat protein and/or RNA polymerase genes, component M alone cannot produce phage particles and mediate infection. Component L and M are electroporated together into *X. oryzae* mutants lack of nutrition X, Y, and Z, then bacteria are grown in a selected nutrition medium at 28° C. SS-iXp12 phage particles are harvested and purified from growth medium as Example 1. Phage infectivity assay and quality controls are performed as Example 5. The individual clones that yield the highest inhibitory efficiency on the bacterial growth but do not infect bacteria for the second time will be selected for further application in the field as described as Xp12 variants. The field tests are performed as described in Example 10. SS-iXp12 phages with the greatest inhibitory effects on *X. oryzae* growth are selected based on the field test results for the further application and commercial use. Because the genome of SS-iXp12 phages do not contain the coat protein and RNA polymerase gene, it cannot propagate in the filed anymore and can only be used for one time. The detailed strategy and process flowchart is further illustrated in FIG. 11B.

Figure 12:
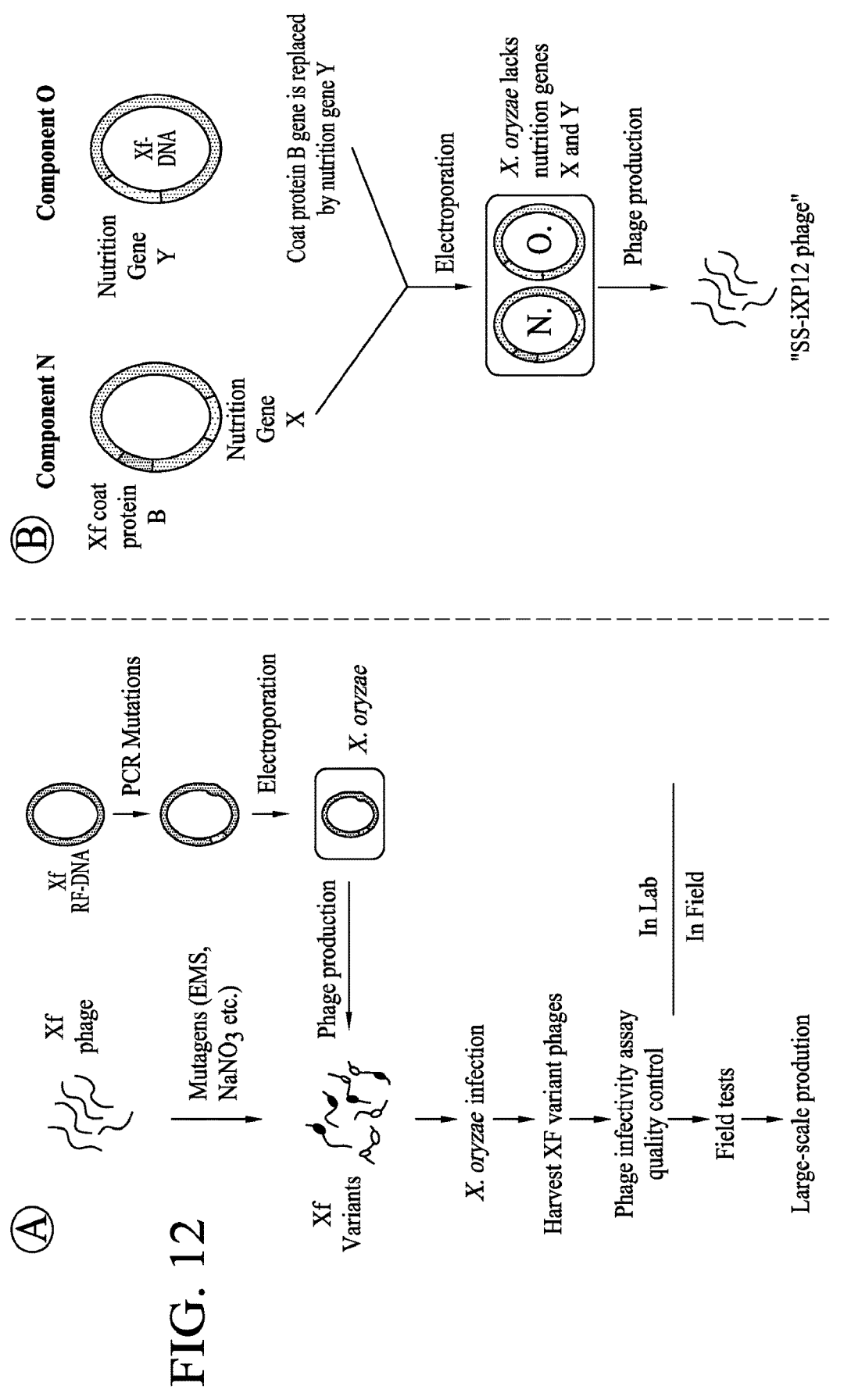

Example 12. Purification, Engineering and Application of Xf Phage to Inhibit Rice Blight This application claims methods to generate and apply recombinant or chemical-mutated Xf phages as a bio-control tool that inhibit rice blight disease in the field (FIG. 12).

Xf phage is propagated in *Xanthomonas oryzae* grown exponentially in PS or LB medium as described in Example 1. When the bacterial concentration reached $10^9$ cells/ml, Xf phages are added to provide a final concentration of $10^{10}$ PFU per milliliter and continue to culture for 24 hours. At the end of cultivation the phage titer reaches $2.5 \times 10^{12}$ PFU/ml. Ten liters of crude lysate was used for phage purification. Host cells and debris are removed by centrifugation at 10,000 g-force for 20 min. Ammonium sulfate is slowly added to the supernatant, with stirring, to 30% saturation. The mixture is allowed to settle for 24 hours in a cold room. The precipitate is then collected by centrifugation and resuspended in one liter of 0.05 M phosphate buffer. For further clarification, the above procedures are repeated once. Finally the resulted precipitate is suspended in 20 ml of 0.05 M phosphate buffer, pH 7.0, and dialyzed against the same buffer to remove ammonium sulfate. Xf phage is then precipitated by centrifugation at 100,000 g-force for 3 hours. For further purification, the phage precipitates are suspended in CsCl at density of 1.260 and centrifuged to equilibrium in a SW-50 rotor at 146,821 g-force for 24 hours. The resulting dense band of Xf phage was collected and freed from CsCl by dilution with SSC (0.15 M NaCl, 0.015 M sodium citrate) and several cycles of washing by high speed centrifugation.

(1) RF DNA of Xf phage is purified as described in Example 2. Xf RF DNA is synthesized directly synthesized by a company (GenScript, Coralville, Iowa) based on the SEQ ID 26. The synthesized DNA fragments are ligated and subcloned into a kanamycin-resistant pUC57 vector and amplified in *E. coli*. Mutations of Xf phage DNA where one or more nucleotides or genes are added, deleted, or substituted are cloned using PCR or generated by treatment with ethyl methanesulfonate or sodium nitrite. These mutated or recombinant Xf DNAs (herein called "Xf variants") are electroporated into *Xanthomonas oryzae*, and Xf variant particles are harvested and purified from growth medium as described above. Phage infectivity assay are performed as Example 5. The individual clones that yield the highest inhibitory efficiency on the bacterial growth will be selected for further application in the field. Phage stocks are aliquoted and stored in 0.1 M phosphate buffer, pH 7.0 at 4° C. The field tests of Xf variant phages are performed as described in Example 10. Xf variant phages cause the lysis of *X. oryzae*, and new Xf variant phages are released to infect more bacteria in the rice field. The detailed strategy and process flowchart is further illustrated in FIG. 12A.

(2) To generate a controllable, "single-shot infectious" Xf (herein called "SS-iXf") phage, the following procedures are performed (FIG. 12B):

(a) "Component N": A plasmid containing DNA fragments encoding a protein having the amino acid sequence of SEQ ID NO: 13 and 57, or proteins having the same amino acid sequences where one or more amino acids are added, deleted, or substituted amino acids, was cloned in a broad-host-range expression DNA vector. This DNA vector contains an essential nutrition gene X that can compensate nutrition deficiency of bacteria mutants. These DNAs (herein called "component N") are electroporated into *Escherichia coli* or *X. oryzae* bacteria mutants, grown in a selected nutrition medium, and DNAs are purified as Example 2.

(b) "Component O": A DNA fragment of an essential nutrition gene Y (different gene from component N) is amplified using PCR, and subcloned into RF DNAs of Xf variants to replace their coat protein B genes (e.g. nucleotide 4353-4583 in SEQ ID 26). These recombinant Xf RF DNAs containing a nutrition gene Y (called "component O") are electroporated into *X. oryzae* cells bacteria mutants and grown in a selected nutrition medium. Component O is then purified as described in Example 2. Due to the loss of the essential major coat protein B gene, component O alone cannot produce Xf phage particles.

(c) Component N and O are electroporated together into *X. oryzae* mutants lack of nutrition gene X and Y, then bacteria are grown in a selected nutrition medium at 28° C. SS-iXf phage particles are harvested and purified from growth medium as described above. Phage infectivity assay and quality controls performed as Example 5. The individual clones that yield the highest inhibitory efficiency on the bacterial growth but do not infect bacteria for the second time will be selected for field tests as described in Example 10. Because the genome of SS-iXf phages do not contain the major coat protein B gene, it can be only used for one time and will not propagate in the filed anymore. The detailed strategy and process flowchart is further illustrated in FIG. 12B.

Ahmad A A, Askora A, Kawasaki T, Fujie M, Yamada T. The filamentous phage XacF1 causes loss of virulence in *Xanthomonas axonopodis* pv. *citri*, the causative agent of citrus canker disease. Front Microbiol. 2014 Jul. 1; 5:321.

Casadevall A, Day L A. DNA packing in the filamentous viruses fd, Xf, Pf1 and Pf3. Nucleic Acids Res. 1982 Apr. 10; 10(7):2467-81.

Chen F C, Koopmans G, Wiseman R L, Day L A, Swinney H L. Dimensions of Xf virus from its rotational and translational diffusion coefficients. Biochemistry. 1980 Apr. 1; 19(7):1373-6.

Cheng C M, Wang H J, Bau H J, Kuo T T. The primary immunity determinant in modulating the lysogenic immunity of the filamentous bacteriophage cf. J Mol Biol. 1999 Apr. 16; 287(5):867-76.

Chow T Y, Lin Y T, Kuo T T, Stability of Xp12. Bot Bull. Academia Sinica 7: 57-65. Dai H, Chiang K S. Kuo, T T, Characterization of a New Filamentous Phage Cf from *Xanthomonas citri*. J. Gen. Virol. 1980, 46, 277-89.

Dai H, Chow T Y, Liao H J, Chen Z Y, Chiang K S. Nucleotide sequences involved in the neolysogenic insertion of filamentous phage Cf16-v1 into the *Xanthomonas campestris* pv. *citri* chromosome. Virology. 1988 December; 167(2):613-20.

Dai H, Tsay S H, Kuo T T, Lin Y H, Wu W C. Neolysogenization of *Xanthomonas campestris* pv. *citri* infected with filamentous phage Cf16. Virology. 1987 February; 156(2):313-20.

Ehrlich M, Lin F H, Ehrlich K, Brown S L, Mayo J A. Changes in macromolecular synthesis in *Xanthomonas oryzae* infected with bacteriophage XP-12. J Virol. 1977 September; 23(3):517-23.

Exconde, O. R. Yield losses due to bacterial leaf blight of rice. Philippines Agriculture 1973; 57, 128-140.

Feng T Y, Tu J, Kuo T T. Characterization of deoxycytidylate methyltransferase in *Xanthomonas oryzae* infected with bacteriophage Xp12. Eur J Biochem. 1978 Jun. 1; 87(1): 29-36.

Frangione B, Nakashima Y, Konigsberg W, Wiseman R L. The amino acid sequence of the major coat protein subunit of the filamentous virus Xf. FEBS Lett. 1978 Dec. 15; 96(2):381-4.

Gottwald, T. R. 2000. Citrus canker. The Plant Health Instructor. DOI: 10.1094/PHI-I-2000-1002-01. Updated 2005.

Kuo T T, Chao Y S, Lin Y H, Lin B Y, Liu L F, Feng T Y. Integration of the DNA of filamentous bacteriophage Cflt into the chromosomal DNA of its host. J Virol. 1987 January; 61(1):60-5.

Kuo T T, Chiang C C, Chen S Y, Lin J H, Kuo J L. A long lytic cycle in filamentous phage Cf1tv infecting *Xanthomonas campestris* pv. *citri*. Arch Virol. 1994; 135(3-4):253-64.

Kuo T T, Chow T Y, Lin Y T. A new thymidylate biosynthesis in *Xanthomonas oryzae* infected by phage Xp12. Virology. 1982 Apr. 30; 118(2):293-300.

Kuo T T, Huang T C, Chow T Y. A filamentous bacteriophage from *Xanthomonas oryzae*. Virology. 1969 November; 39(3):548-55.

Kuo T T, Huang T C, Teng M H. 5-Methylcytosine replacing cytosine in the deoxyribonucleic acid of a bacteriophage for *Xanthomonas oryzae*. J Mol Biol. 1968 Jul. 14; 34(2):373-5.

Kuo T T, Lin Y H, Huang C M, Chang S F, Dai H, Feng T Y. The lysogenic cycle of the filamentous phage Cflt from *Xanthomonas campestris* pv. *citri*. Virology. 1987 February; 156(2):305-12.

Kuo T T, Lin Y T. Xf phage invading the host cells with their protein coats. J Gen Virol. 1976 August; 32(2):241-7.

Kuo T T, Tan M S, Su M T, Yang M K. Complete nucleotide sequence of filamentous phage Cf1c from *Xanthomonas campestris* pv. *citri*. Nucleic Acids Res. 1991 May 11; 19(9):2498.

Kuo T T, Tu J. Enzymatic synthesis of deoxy-5-methylcytidylic acid replacing deoxycytidylic acid in *Xanthomonas oryzae* phage Xp12DNA. Nature. 1976 Oct. 14; 263(5578):615.

Lin J Y, Wu C C, Kue T T. Amino acid analysis of the coat protein of the filamentous bacterial virus xf from *Xanthomonas oryzae*. Virology. 1971 July; 45(1):38-41.

Mao, R, Zheng J, Zhang R., Side effects of copper fungicides on *Amblyseius cucumeris* by laboratory bioassays. Bulletin of Insectology. 2011, 64 (1): 69-72.

Marzec C J, Day L A. DNA and protein lattice-lattice interactions in the filamentous bacteriophages. Biophys J. 1983 May; 42(2):171-80.

Marzec C J, Day L A. A theory of the symmetries of filamentous bacteriophages. Biophys J. 1988 March; 53(3):425-40.

Marzec C J, Day L A. An electrostatic spatial resonance model for coaxial helical structures with applications to the filamentous bacteriophages. Biophys J. 1994 December; 67(6):2205-22.

Mather M W, McReynolds L M, Yu C A. An enhanced broad-host-range vector for gram-negative bacteria: avoiding tetracycline phototoxicity during the growth of photosynthetic bacteria. Gene. 1995 Apr. 14; 156(1):85-8.

Nelson M. and McClelland M. Effect of site-specific methylation on DNA modification methyltransferases and restriction endonucleases. Nucleic Acids Res. 1991; 19: 2045-71.

NINO-Liu, D O, Roland P C, Bogdanove, A J. *Xanthomonas oryzae* pathovars: model pathogens of a model crop. Mol Plant Pathol 2006, 7(5): 303-324.

Oshiro E E, Nepomuceno R S, Faria J B, Ferreira L C, Ferreira R C. Site-directed gene replacement of the phytopathogen *Xanthomonas axonopodis* pv. *citri*. J Microbiol Methods. 2006 April; 65(1):171-9.

Sega, G A. A review of the genetic effects of ethyl methanesulfonate. Mutat Res. 1984 September-November; 134(2-3):113-42.

Shieh G J, Lin C H, Kuo J L, Kuo T T. Characterization of an open reading frame involved in site-specific integration of filamentous phage Cf1t from *Xanthomonas campestris* pv. *citri*. Gene. 1995 May 26; 158(1):73-6.

Thomas G J Jr, Day L A. Conformational transitions in Pf3 and their implications for the structure and assembly of filamentous bacterial viruses. Proc Natl Acad Sci USA. 1981 May; 78(5):2962-6.

Thomas G J Jr, Prescott B, Day L A. Structure similarity, difference and variability in the filamentous viruses fd, If1, IKe, Pf1 and Xf. Investigation by laser Raman spectroscopy. J Mol Biol. 1983 Apr. 5; 165(2):321-56.

Thomas G J Jr, Prescott B, Opella S J, Day L A. Sugar pucker and phosphodiester conformations in viral genomes of filamentous bacteriophages: fd, If1, IKe, Pf1, Xf, and Pf3. Biochemistry. 1988 Jun. 14; 27(12):4350-7.

Tseng Y H, Lo M C, Lin K C, Pan C C, Chang R Y. Characterization of filamentous bacteriophage ⌀ Lf from *Xanthomonas campestris* pv. *campestris*. J Gen Virol. 1990 August; 71 (8):1881-4.

Van Brunt J. Amplifying genes: PCR and its alternatives. Biotechnology (N Y). 1990 April; 8(4):291-4.

Wang H J, Cheng C M, Wang C N, Kuo T T. Transcription of the genome of the filamentous bacteriophage cf from both plus and minus DNA strands. Virology. 1999 Apr. 10; 256(2):228-32.

Wang R Y, Ehrlich M. 5-methyl-dCTP deaminase induced by bacteriophage XP-12. J Virol. 1982 April; 42(1):42-8.

Wen F S, Tseng Y H. Nucleotide sequence determination, characterization and purification of the single-stranded DNA-binding protein and major coat protein of filamentous phage phiLf of *Xanthomonas campestris* pv. *campestris*. J Gen Virol. 1994 January; 75 (1):15-22.

Wiseman R L, Day L A. Different packaging of DNA in the filamentous viruses Pf1 and Xf. J Mol Biol. 1977 Nov. 5; 116(3):607-11.

Yang M K, Kuo T T. A physical map of the filamentous bacteriophage Cf genome. J Gen Virol. 1984 July; 65 (7):1173-81.

Yang, M K, Su, W C, Kuo T T, High efficient transfection of *Xanthomonas campestris* by electroporation. 1991; Bot Bull. Academia *Sinica* 32: 197-203.

Yang M K, Yang Y C. The A protein of the filamentous bacteriophage Cf of *Xanthomonas campestris* pv. *citri*. J Bacteriol. 1997 May; 179(9):2840-4.

The invention claimed is:

1. An isolated or recombinant nucleic acid molecule comprising a nucleotide sequence encoding an amino acid sequence, wherein said nucleotide sequence consists of: a sequence of SEQ ID NO: 25 or its full length complement.

2. A vector comprising the isolated or recombinant nucleic acid molecule of claim 1.

3. The vector of claim 2, wherein said vector replicates in a Cf-type phage-infected *Xanthomonas citri* host.

4. A host cell comprising the vector of claim 2, wherein said host cell is a bacterial cell or plant cell.

5. The host cell of claim 4, wherein said host cell is a bacterial cell and said bacterial cell is a *Xanthomonas citri* subsp. *citri* cell.

* * * * *

SEQUENCE LISTING

<160> NUMBER OF SEQ ID NOS: 89

<210> SEQ ID NO 1
<211> LENGTH: 7308
<212> TYPE: DNA
<213> ORGANISM: Artificial Sequence
<220> FEATURE:
<223> OTHER INFORMATION: nucleotide sequence derived from Cf type bacteriophage genome

<400> SEQUENCE: 1

```
gaattcggcc gtcgcatccg gctgatccct gatgcaaccg ccaaagctgc gcagcctgct     60
gcacgtgtct cctaacccag atgcatgaga gcagggattc tgagcaatgg caaaggtcct    120
gacctgcacg caatacaacg attcaacgca gcaatgcgag gtccaagcct ggattgatca    180
atcggattgg acgacaccac ttcccaccat cgaacaggcc gcgatggtgg gcggcgctta    240
cttcatcggc ctgatgaccc ttgcagtcat taaaggactg ctcaacccaa aatcaataga    300
ggaatagcat caatggaaaa gaacatttcg accgttgtca ccaaggctaa gtcggctgtc    360
agcaacgcca agaccgccgc aattctgggt agcactgcct tgatggccat gcccggtttc    420
gccttcgcgt ccggtggcgg cggcgacttc gacggcaccg caatcatcgg caaggtgact    480
acctataccg ccatcggcgt gaccattctg gccccttcgc gctcggtcgt tggacgcttc    540
gccactcggt ctgatcggcg gcaagtgagc caatcagcgg catagcaggg gaggggaaac    600
cctccctttt tcaatggggg atacgcaatg gaaggattga tcgtgttggt gttcctgatc    660
catgcccgca cgtgtgcgca acgggctgga actgatgcgc gggctcggcg gatatttcgc    720
acgcgctgta gttcggcgaa ttgcctacgt tgtagtcgcg gcgtgcttcg gcctactttt    780
gcaattgtgc agtgggagtg cgcacgcggc cgttgatcag ggtgaggcgt actcgctttg    840
catgaaattc gctagcgata tggtggcgaa aaatccggac atgcgacgaa acccctcgtg    900
ccggtcgcgt agggcatttc aatacacctg ccaatatgaa gccattccgt atgtaggcgt    960
tcgcagtggt ccgtagatac ttgcggcgac tacagctatg acgatcagta cacatgcgca   1020
tcgcgtaact cgaacaagct tgctgatgcc gcaccgtggt acacccctcc gcctaactgc   1080
atatccggtt gtcaagtgca aggcacttcg ttcagtggcg acaacggtgg cgtcaagacc   1140
tatggaatga aggaccgtac ctataacggt tctatctgta cccctaccaa gcccaccaac   1200
gatatcggtg aattgcagga ggaaaagaac gacgccacca aggaaaaagc gcctgagtgc   1260
accgcgctcg ggtctgggca gaccgcttgt ttgaagccaa acggcgacta ttgcgcaacg   1320
gcgtcatccg gcaagacgtt ctgctggaag cctgccgaga cgggcaaaaa aactgacgct   1380
actgatgcgc aaagcaagac tccaaagggc gaccctgtaa cgccgcctcc tatcccgccc   1440
ccggatggtg aatggcagcg caaggaaggc caccagcaga ccacgtgcgt gaacaatacg   1500
```

-continued

```
tgcactacct acaacgttac caactacacg accgtgcctt ccggcacgtc caagaacggc      1560
acgggtgaca cagcgccga tggctcgggc aacacatctg gcaatggcag caatagcggc      1620
acggggaaga aggacgacga cagcaaggat agtgctacgg atagcggcaa ttgcgatgcc      1680
ccacctatct gtgtgggcga cgttgaagtg tttgcaattg aaattcacat ggaaaatcga      1740
ttgcaacaca cgcggcaatg agatcactca aggcgattca tgtgctgatg gtgatgtgcc      1800
tgtctgtgct ggcaagtcgt gtaaagccga ggcctacgcg caggtggtac agcagtggaa      1860
acaactgcgc tgtagaggcg atggggcagg ggatggcctc gcgtgccgct gctattagca      1920
atggtgacga tgctggtgtg gttgagggaa tctggggcgg tgaatctgcc ggcgccggcc      1980
ttaagttgcg ccaggatttg gtcaacgttg cggcaatgg tactggcggc ttgttgcccg      2040
acgttgatat cgaaggtcaa cactggaccg taccctctgg atttttcgac gcaattgctg      2100
cggtcaagat ggttatcatc gcgatgtgca cagtgatcgc catgttcgtc gttgggagga      2160
acatctaatg ttcgattggg cacgtgactt tgcgaacaat ttctttgaga acgcgcagat      2220
gcggtccata agttggtcaa gctcaaggcc gctatatggc tcggccgatt gctgtccgct      2280
ctcggtctgg gtttcgccgc gcagcatttc atctacaacc cgatcatcga atacgcacag      2340
aacgcatggt cgtccgttcc tgcgggcatc gctgcatggg tacacgcatt gggtatcgat      2400
gcaggcgtgt cgatcatcct gagtgcctat ggcattcgcg gtgcggagcg catctttatt      2460
caacgtagga accaagcaac atgatcggcg acaccgcgtc tatttcactg ctcaccggct      2520
tgccaggatc tggcaagagc ttgcgcatta ccaggcgat tcgctatctc atggacaagg      2580
gtgcgcacgt ctacgtgtgc aacatcgacg gcatctccgt gcccggcacg acgccgtggg      2640
ctgatccgca taagtggcaa gatctaccgg ctgggtcaat tcttttcgtt gatgaggcgc      2700
agcatttttt ccccgcacgt cgtggcgggg atccggtcga aacgatcaag gcgatgtcca      2760
cgattcgaca cgacggcgtg cgtttggtgc ttgccacgca gcagccgaac tacctcgaca      2820
cctatctgcg tggattggtc ggctatcacg aacacctgct cgtcagagc ggcaaacaga      2880
agaccttat tttccgcaat agtcagatca tcgaagaggt gcggtcgccg ttgccgcgca      2940
tcaaaaagct ctacgactac gaagtgtgga acagccaac agagtgcttc aagttctaca      3000
agtcggctga ggtccacacg atgaagtatc agatgccggc actggtgaaa aaggcattga      3060
tgatccttcc tgtcgtcgca cttctggctg gcggcgcgtg gtacgccgtc taccgcgaca      3120
ccatgttcgc caagaaagca gacgctgcgc ccgccaataa gacggccccc tcggggccgt      3180
cgctggcggg cactgcgtct gcgggtgcag cagctcgtcc caaggtcaac agcgcagagg      3240
actacgtcgg tcagcttgtg ccattggtcg ccgatgtgcc ttggtcggca cctgcctacg      3300
tggatcgccc tgtggtgtcc gatccccatg tgtattgcat ggcaactgag aacacctgtc      3360
gatgtgtcac tgagcaaaat tcgcgcgttg tgatgcgcga tgacgtgtgc cgcgacattg      3420
cgcggtgggg cgagccatat aacccgtata agccgccgca tagtccggcg cagaagcagc      3480
aggattcccc ggttgcagaa gccacgcagc ctaagcccca ggtgccccag cagagcgggg      3540
cagtgtcgtc gtccgtgcaa agggccacac gctcccttgg cacgttcccc gaatcgccgc      3600
cttaccagac gacaacgtac accccaccca ccaccaggga tctgtgatga gcagtagtgc      3660
acgcgagtta ctgaagtgga ttgcgcttgt ctgcatgaca ttcgaccacg ttgccaaggt      3720
gttctatgac ggctacgtgc ccgtgttgtc cgagctaggc cggattgcgt ttccgctctt      3780
cgcactggtc atggcctaca acctggcaca gcctggagct gatgtaggca agtcggtccg      3840
ccggctggtg tgctgggggc tgttggcgca accgttccac gcctgggcgt ttggctactg      3900
```

-continued

```
ggtgcccgtg aacgtccttc tggcgttcgc cctggctgct gccgctgtct gggctatcca   3960
gcgcggccgc tgggtgctgc tgatgctctg tgccgctcca gccccgttgt tcgtcgacta   4020
ccaatggact ggcattgcgc tggtggtggc aggctgggcc tattacgcca aagtgatgcg   4080
tacgcctata ccggtcgtca tggcactggg cgctctatgt tggttcaacg gcagcttgtg   4140
ggcccttctt gccatcccaa tcattgccct ctcagaagcg gtcaccaatc gaggtatggc   4200
tattcctcgc acgcgccttg gcttctacgg ctattatgtg gggcatctag ctatcttggg   4260
tctgctggcc ctcaagcccg cccttatttc gtgacgcgag gggaagtgca tggaagcgag   4320
atttgcaatg ttgcttgcgc tggctatcgt tgttccttgt cacgcgcagc aggttcacaa   4380
gtgccgtgag cgagggcagg tcgtttatca gtcagcgccg tgcgcttccg gccaagccca   4440
gaaggtctgg gacgccgcac cagctcctga gcaaagcaat gccgagcagt ggcgccttta   4500
ccgtattcgc aagcagctcg atagcaggta cgcagctgac agatctgcat ccgctgccgc   4560
ctatgtgtct ggcccacaat ccagcaacgc atgcgagtct gccaaggctc agcgcaagca   4620
agtctatgac gcggccggtc tccatcgttc ttatgagatt ccagctatt gggacaacgt   4680
ggtgcaaaac gcctgtaagt gacctggggt gtaggggcat agcccctacg ataacgcct   4740
cacccgcgcc gtggagctcg aggcccacgc gttctacgca ccacctgtgc tcgatcggcg   4800
gaccccgcgc catccaccac tgacaaccgc ttttcgcgcc tctgcagcag cacgtcccgc   4860
agatagatca cgtctgcgcc tcgagacaaa cgagaccctg gagatcttgt ggcagtaggc   4920
tttcgaggat tcgccgatcg cgcattgcgt tcttctgaca tcaacagtga ccattcccgt   4980
gcgatcgcgc atgtcagcgc ccaataccgc atatcgcacg gttcgatgtc gtaattctcc   5040
ggggtgaaga accggtgccc ctgaaaacca aaccggccc aagggccggt caggtctacg   5100
cgatcgtagg tgtctagcgt cattgtccag tccgcttcct gtggagggac cagcagtgat   5160
aggccgccag ggcgcacagc agcgtcaaca gcacacttcg cataatgtat agagggtggg   5220
taacggctac cggcgagagg gccgctagca gcgcctcatg cgcccctgtg tgtaccgcca   5280
ggaccagcag cgcgaccacc gcggcggccg cgcttagcct gtccaacact gatcgccata   5340
gcgcttttc agccggcgat gccgctgctt cggcgtgaat tttcgccatc cattcgccgc   5400
catccagatg tgcccatagcg tatagctctg caattcgtgc gtcaggaacc gggtaccggc   5460
caacgcgcca gccgcttatc agcgcccgcg tcactccaat ttttttgctc aacatgttgt   5520
ctgacggtat ggcgcacgac ttgcgcacgg tgtcaagcaa attatttaca tggtccatga   5580
caggtttttc ttgacagaga ggacagtgaa aactatacat gctcccgtgc ttaggcaacc   5640
ctaagcaccg cgcaccccg gctcccctcc ggggtccgcg tcaagggcag gggaggggc   5700
tacaccgtga atccatattc gatcctgggc cagcttttgg cgctgcacat tctcgtgtcg   5760
atctgcgtgc tcaccgggta cgcaatcgtc gctgtgatct gttggtgtct tgatcgcaag   5820
cacgacgcga tggttgctca aattgagcaa gccgcattgg tcgctatcgc atatcgcgag   5880
gtgcgtcgtg gctgagtctc gatctgttgc atggatgatt gccgccagctc gagtgcaggg   5940
cggcccccgc atttacgtct tgaccatcgt cgtcaacggc aacgctgttg aacagagcta   6000
ttttgcatcg cgcaccgatg ctgctgatgc acgtgacgct gccatggagt tctatcgtgg   6060
ctgatggcac ctgctcgttc tgtggcgaca ccactgccta cttttttccca ggcggtttgt   6120
gcgttgcatg cacctcgaag aacgcacgca tccgcatgca tgaacagccc acgcaatcgc   6180
gtgagttgtc cgcgttcgat gcatctgtgg gcgtcatgca ggccgcgacg cgccgcaccg   6240
```

-continued

```
aaattgccgc agagaagatc caaaagaaca agcgcgtggt gggtacgagc gtgcgtgagt    6300
tcgacgctgc ccatccgatc gcattgaccg ctgagggcca cgcgctggcc cttgggcttgt   6360 ccattacaaa acaagtgaca cgcgggcctc tactacaggc accgtgacca tcgaaatcga    6420
cccgctgcaa gcgcgggcgc aacgctgcg taagtccgtg attaccggag cacgtctgca    6480
tgaccaggaa gcgaaaaaag gctccttccg gggtgcgtgg tatttcctca cgctcaccta    6540
ccgtgatgga agcgacagca gccctcgtga cgttagcgaa ctatttaaac gcatgcgcgg    6600
ccacttcaat cgccttaaat ctgggcgcgc acggtggaac cgtgaaagct ttcgttacgt    6660
atgggtcgga gaactcaccc agcgattccg tccgcactac cacgtgatgc tgtgggttcc    6720
cactggcatg tatttcggca agtcgatca acgcggttgg tggccacatg gcacaacgca     6780
aattgagaaa gcccgaaact cgtcggcta tctcgcgaaa tacgcgagca agttcactgc     6840
ccttacagct ggagcttttc ccaaaggctt ccgcacacat ggcattggtg gactcgatac    6900
cgaatccaag cgcgagttgc cgtggtggaa ggccccgaaa gacgcgcgtg aagctctcgg    6960
cggggaagcg gatatccgca aagcaaaggg cggttggttc gacaggctta ccggagagtt    7020
ctggccgtct ccgtggaaag tcacattcat cttcggccgg acattcgcct ggaaggtagt    7080
cccactatga aagttcagat catgagttcc gctgtcgcca tccgttcgtt tccggctcgc    7140
gatggtaagc cagcaacgca tttccgcgag cagaccgccg ccgtgttgcg cgagggcgat    7200
ttcccgctgc cgttcaccat cagccttgat gaggatcaag cgccgtatgg cgaaggtttc    7260
tacgtcatcg atcccaagtc gatgcagaac aacaaatacg gcggcctg              7308
```

```
<210> SEQ ID NO 2
<211> LENGTH: 1865
<212> TYPE: DNA
<213> ORGANISM: Artificial Sequence
<220> FEATURE:
<223> OTHER INFORMATION: nucleotide sequence derived from ORF165 of Cf
      bacteriophage

<400> SEQUENCE: 2
```

```
ggtaccggcc aacgcgccag ccgcttatca gcgcccgcgt cactccaatt tttttgctca     60
acatgtggtc tgacggtatg gcgcacgact tgcgcacggt gtcaagcaaa ttatttacat    120
ggtccatgac aggtttttct tgacagagag gacagtgaaa actatacatg ctcccgtgct    180
taggcaaccc taagcaccgc gcacccccgg ctcctccggg gtccgcgtca aggggcaggg    240
gagggggcta caccgtgcat ccatattcga tcctgggcca gcttttggcg ctgcacattc    300
tcgtgtcgat ctgcgtgctc accgggtacg caatcgtcgc tgtgatctgt tggtgtcttg    360
atcgcaagca cgacgcgatg gttgctcaaa ttgagcaagc cgcattggtc gctatcgcat    420
atcgcgaggt gcgtcgtggc tgagtctcga tctgttgcat ggatgattgc gccagctcga    480
gtgcagggcg gccccgcat ttacgtcttg accatcgtcg tcaacggcaa cgctgttgaa     540
cagagctatt ttgcatcgcg caccgatgct gctgatgcac gtgacgctgc catggagttc    600
tatcgtggct gatggcacct gctcgttctg tggcgacacc actgcctact tttccccagg    660
cggtttgtgc gttgcatgca cctcgaagaa cgcacgcatc cgcatgcatg aacagcccac    720
gcaatcgcgt gagttgtccg cgttcgatgc atctgtgggc gtcatgcagg ccgcgacgcg    780
ccgcaccgaa attgccgcag agaagatcca aagaacaag cgcgtggtgg gtacgagcgt     840
gcgtgagttc gacgctgccc atccgatcgc attgaccgct gaacgcgcag cgctggccct    900
tgggcttgtc cattacaaaa caagtgacac gcgggcctct actacaggca ccgtgaccat    960
```

```
cgaaatcgac cgctgcaag cgcgggcgca acggctgcgt aagtcgctga ttaccggagc    1020
acgtctgcat gaccaggaag cgaaaaaagg ctccttccgg ggtgcgtggt atttcctcac    1080
gctcacctac cgtgatggaa gcgacagcag ccctcgtgac cttagcgaac tatttaaacg    1140
catgcgcggc cacttcaatc gccttaaatc tgggcgcgca cggtggaacc gtgaaagctt    1200
tcgttacgta tgggtcggag aactcaccca gcgattccgt ccgcactacc acgtgatgct    1260
gtgggttccc actggcatgt atttcggcaa agtcgatcaa cgcggttggt ggccacatgg    1320
cacaacgcaa attgagaaag cccgaaactg cgtcggcata ctcgcgaaat acgcgagcaa    1380
gttcactgcc cttacagctg gagcttttcc caaaggcttc cgcacacatg cattggtgg     1440 actcgatacc gaatccaagc gcgagttgcc gtggtggaag gccccgaaag acgcgcgtga    1500
agctctcggc ggggaagcgg atatccgcaa agcaaagggc ggttggttcg acaggcttac    1560
cggagacttc tggccgtctc cgtggaaagt cacattcatc ttcggccgga cattcgcctg    1620
gaaggtagtc ccagtatgaa agttcagatc atgagttccg ctgtcgccat ccgttcgttt    1680
ccggctcgcg atggtaagcc agcaacgcat ttccgcgagc agaccgccgc cgtgttgcgc    1740
gagggcgatt cccgctgccg gttcaccatc agccttgatg aggatcaagc gccgtatggc    1800
gaaggtttct acgtcatcga tcccaagtcg atgcagaaca caaatacgg cggcctggaa     1860 ttcgg                                                                1865

<210> SEQ ID NO 3
<211> LENGTH: 98
<212> TYPE: PRT
<213> ORGANISM: Artificial Sequence
<220> FEATURE:
<223> OTHER INFORMATION: amino acid sequence derived from an
      ssDNA-binding protein of bacteriophage Cfc1

<400> SEQUENCE: 3

Met Lys Val Gln Ile Met Ser Ser Ala Val Ala Ile Arg Ser Phe Pro
1               5                   10                  15

Ala Arg Asp Gly Lys Pro Ala Thr His Phe Arg Glu Gln Thr Ala Ala
            20                  25                  30

Val Leu Arg Glu Gly Asp Phe Pro Leu Pro Phe Thr Ile Ser Leu Asp
        35                  40                  45

Glu Asp Gln Ala Pro Tyr Gly Glu Gly Phe Tyr Val Ile Asp Pro Lys
    50                  55                  60

Ser Met Gln Asn Asn Lys Tyr Gly Gly Leu Glu Phe Gly Arg Arg Ile
65                  70                  75                  80

Arg Leu Ile Pro Asp Ala Thr Ala Lys Ala Ala Gln Pro Ala Ala Arg
                85                  90                  95

Val Ser

<210> SEQ ID NO 4
<211> LENGTH: 90
<212> TYPE: PRT
<213> ORGANISM: Artificial Sequence
<220> FEATURE:
<223> OTHER INFORMATION: amino acid sequence derived from a coat protein
      of Cf1c bacteriophage

<400> SEQUENCE: 4

Met Glu Lys Asn Ile Ser Thr Val Val Thr Lys Ala Lys Ser Ala Val
1               5                   10                  15

Ser Asn Ala Lys Thr Ala Ala Ile Leu Gly Ser Thr Ala Leu Met Ala
            20                  25                  30
```

```
Met Pro Gly Phe Ala Phe Ala Ser Gly Gly Gly Asp Phe Asp Gly
                35                  40                  45

Thr Ala Ile Ile Gly Lys Val Thr Thr Tyr Thr Ala Ile Gly Val Thr
 50                  55                  60

Ile Leu Ala Pro Ser Arg Ser Val Val Gly Arg Phe Ala Thr Arg Ser
 65                  70                  75                  80

Asp Arg Arg Gln Val Ser Gln Ser Ala Ala
                85                  90

<210> SEQ ID NO 5
<211> LENGTH: 419
<212> TYPE: PRT
<213> ORGANISM: Artificial Sequence
<220> FEATURE:
<223> OTHER INFORMATION: amino acid sequence derived from a coat protein
      of Cf1c bacteriophage
<220> FEATURE:
<221> NAME/KEY: misc_feature
<222> LOCATION: (100)..(100)
<223> OTHER INFORMATION: Xaa can be any naturally occurring amino acid

<400> SEQUENCE: 5

Met Pro Arg Thr Cys Ala Gln Arg Ala Gly Thr Asp Ala Arg Ala Arg
 1               5                  10                  15

Arg Ile Phe Ala Arg Ala Val Val Arg Arg Ile Ala Tyr Val Val Val
                20                  25                  30

Ala Ala Cys Phe Gly Leu Leu Leu Gln Leu Cys Ser Gly Ser Ala His
                35                  40                  45

Ala Ala Val Asp Gln Gly Glu Ala Tyr Ser Leu Cys Met Lys Phe Ala
 50                  55                  60

Ser Asp Met Val Ala Lys Asn Pro Asp Met Arg Arg Asn Pro Ser Cys
 65                  70                  75                  80

Arg Ser Arg Arg Ala Phe Gln Tyr Thr Cys Gln Tyr Glu Ala Ile Pro
                85                  90                  95

Tyr Val Gly Xaa Ser Gln Trp Ser Val Asp Thr Cys Gly Asp Tyr Ser
                100                 105                 110

Tyr Asp Asp Gln Tyr Thr Cys Ala Ser Arg Asn Ser Asn Lys Leu Ala
                115                 120                 125

Asp Ala Ala Pro Trp Tyr Thr Pro Pro Asn Cys Ile Ser Gly Cys
                130                 135                 140

Gln Val Gln Gly Thr Ser Phe Ser Gly Asp Asn Gly Gly Val Lys Thr
145                 150                 155                 160

Tyr Gly Met Lys Asp Arg Thr Tyr Asn Gly Ser Ile Cys Thr Pro Thr
                165                 170                 175

Lys Pro Thr Asn Asp Ile Gly Glu Leu Gln Glu Glu Lys Asn Asp Ala
                180                 185                 190

Thr Lys Glu Lys Ala Pro Glu Cys Thr Ala Leu Gly Ser Gly Gln Thr
                195                 200                 205

Ala Cys Leu Lys Pro Asn Gly Asp Tyr Cys Ala Thr Ala Ser Ser Gly
                210                 215                 220

Lys Thr Phe Cys Trp Lys Pro Ala Glu Thr Gly Lys Lys Thr Asp Ala
225                 230                 235                 240

Thr Asp Ala Gln Ser Lys Thr Pro Lys Gly Asp Pro Val Thr Pro Pro
                245                 250                 255

Pro Ile Pro Pro Pro Asp Gly Glu Trp Gln Arg Lys Glu Gly His Gln
                260                 265                 270
```

Gln Thr Thr Cys Val Asn Asn Thr Cys Thr Thr Tyr Asn Val Thr Asn
                275                 280                 285

Tyr Thr Thr Val Pro Ser Gly Thr Ser Lys Asn Gly Thr Gly Asp Asn
            290                 295                 300

Ser Ala Asp Gly Ser Gly Asn Thr Ser Gly Asn Gly Ser Asn Ser Gly
305                 310                 315                 320

Thr Gly Lys Lys Asp Asp Ser Lys Asp Ser Ala Thr Asp Ser Gly
                325                 330                 335

Asn Cys Asp Ala Pro Pro Ile Cys Val Gly Asp Thr Leu Lys Cys Leu
                340                 345                 350

Gln Leu Lys Phe Thr Trp Lys Ile Asp Cys Asn Thr Arg Gly Asn Glu
                355                 360                 365

Ile Thr Gln Gly Asp Ser Cys Ala Asp Gly Asp Val Pro Val Cys Ala
            370                 375                 380

Gly Lys Ser Cys Lys Ala Glu Ala Tyr Ala Gln Val Val Gln Gln Trp
385                 390                 395                 400

Lys Gln Leu Arg Cys Arg Gly Asp Gly Ala Gly Asp Gly Leu Ala Cys
                405                 410                 415

Arg Cys Tyr

<210> SEQ ID NO 6
<211> LENGTH: 388
<212> TYPE: PRT
<213> ORGANISM: Bacteriophage Cf1c

<400> SEQUENCE: 6

Met Ile Gly Asp Thr Ala Ser Ile Ser Leu Leu Thr Gly Leu Pro Gly
1               5                   10                  15

Ser Gly Lys Ser Leu Arg Ile Ile Gln Ala Ile Arg Tyr Leu Met Asp
                20                  25                  30

Lys Gly Ala His Val Tyr Val Cys Asn Ile Asp Gly Ile Ser Val Pro
            35                  40                  45

Gly Thr Thr Pro Trp Ala Asp Pro His Lys Trp Gln Asp Leu Pro Ala
        50                  55                  60

Gly Ser Ile Leu Phe Val Asp Glu Ala Gln His Phe Pro Ala Arg
65                  70                  75                  80

Arg Gly Gly Asp Pro Val Glu Thr Ile Lys Ala Met Ser Thr Ile Arg
                85                  90                  95

His Asp Gly Val Arg Leu Val Leu Ala Thr Gln Gln Pro Asn Tyr Leu
            100                 105                 110

Asp Thr Tyr Leu Arg Gly Leu Val Gly Tyr His Glu His Leu Leu Arg
        115                 120                 125

Gln Ser Gly Lys Gln Lys Thr Phe Ile Phe Arg Asn Ser Gln Ile Ile
    130                 135                 140

Glu Glu Val Arg Ser Pro Leu Pro Arg Ile Lys Lys Leu Tyr Asp Tyr
145                 150                 155                 160

Glu Val Trp Lys Gln Pro Thr Glu Cys Phe Lys Phe Tyr Lys Ser Ala
                165                 170                 175

Glu Val His Thr Met Lys Tyr Gln Met Pro Ala Leu Val Lys Lys Ala
            180                 185                 190

Leu Met Ile Leu Pro Val Val Ala Leu Leu Ala Gly Gly Ala Trp Tyr
        195                 200                 205

Ala Val Tyr Arg Asp Thr Met Phe Ala Lys Lys Ala Asp Ala Ala Pro
    210                 215                 220

-continued

```
Ala Asn Lys Thr Ala Pro Ser Gly Pro Ser Leu Ala Gly Thr Ala Ser
225                 230                 235                 240

Ala Gly Ala Ala Ala Arg Pro Lys Val Asn Ser Ala Glu Asp Tyr Val
            245                 250                 255

Gly Gln Leu Val Pro Leu Val Ala Asp Val Pro Trp Ser Ala Pro Ala
        260                 265                 270

Tyr Val Asp Arg Pro Val Val Ser Asp Pro His Val Tyr Cys Met Ala
    275                 280                 285

Thr Glu Asn Thr Cys Arg Cys Val Thr Glu Gln Asn Ser Arg Val Val
290                 295                 300

Met Arg Asp Asp Val Cys Arg Asp Ile Ala Arg Trp Gly Glu Pro Tyr
305                 310                 315                 320

Asn Pro Tyr Lys Pro Pro His Ser Pro Ala Gln Lys Gln Gln Asp Ser
            325                 330                 335

Pro Val Ala Glu Ala Thr Gln Pro Lys Pro Gln Val Pro Gln Gln Ser
        340                 345                 350

Gly Ala Val Ser Ser Val Gln Arg Ala Thr Arg Ser Leu Gly Thr
    355                 360                 365

Phe Pro Glu Ser Pro Pro Tyr Gln Thr Thr Tyr Thr Pro Pro Thr
370                 375                 380

Thr Arg Asp Leu
385

<210> SEQ ID NO 7
<211> LENGTH: 215
<212> TYPE: PRT
<213> ORGANISM: Bacteriophage Cf1c

<400> SEQUENCE: 7

Met Ser Ser Ser Ala Arg Glu Leu Leu Lys Trp Ile Ala Leu Val Cys
1               5                   10                  15

Met Thr Phe Asp His Val Ala Lys Val Phe Tyr Asp Gly Tyr Val Pro
            20                  25                  30

Val Leu Ser Glu Leu Gly Arg Ile Ala Phe Pro Leu Phe Ala Leu Val
        35                  40                  45

Met Ala Tyr Asn Leu Ala Gln Pro Gly Ala Asp Val Gly Lys Ser Val
    50                  55                  60

Arg Arg Leu Val Cys Trp Gly Leu Leu Ala Gln Pro Phe His Ala Trp
65                  70                  75                  80

Ala Phe Gly Tyr Trp Val Pro Val Asn Val Leu Leu Ala Phe Ala Leu
            85                  90                  95

Ala Ala Ala Ala Val Trp Ala Ile Gln Arg Gly Arg Trp Val Leu Leu
        100                 105                 110

Met Leu Cys Ala Ala Pro Ala Pro Leu Phe Val Asp Tyr Gln Trp Thr
    115                 120                 125

Gly Ile Ala Leu Val Val Ala Gly Trp Ala Tyr Tyr Ala Lys Val Met
130                 135                 140

Arg Thr Pro Ile Pro Val Val Met Ala Leu Gly Ala Leu Cys Trp Phe
145                 150                 155                 160

Asn Gly Ser Leu Trp Ala Leu Leu Ala Ile Pro Ile Ile Ala Leu Ser
            165                 170                 175

Glu Ala Val Thr Asn Arg Gly Met Ala Ile Pro Arg Thr Arg Leu Gly
        180                 185                 190

Phe Tyr Gly Tyr Tyr Val Gly His Leu Ala Ile Leu Gly Leu Leu Ala
    195                 200                 205
```

Leu Lys Pro Ala Leu Ile Ser
    210             215

<210> SEQ ID NO 8
<211> LENGTH: 130
<212> TYPE: PRT
<213> ORGANISM: Bacteriophage Cf1c

<400> SEQUENCE: 8

Met Glu Ala Arg Phe Ala Met Leu Leu Ala Leu Ala Ile Val Val Pro
1               5                   10                  15

Cys His Ala Gln Gln Val His Lys Cys Arg Glu Arg Gly Gln Val Val
            20                  25                  30

Tyr Gln Ser Ala Pro Cys Ala Ser Gly Gln Ala Gln Lys Val Trp Asp
        35                  40                  45

Ala Ala Pro Ala Pro Glu Gln Ser Asn Ala Glu Gln Trp Arg Leu Tyr
    50                  55                  60

Arg Ile Arg Lys Gln Leu Asp Ser Arg Tyr Ala Ala Asp Arg Ser Ala
65                  70                  75                  80

Ser Ala Ala Ala Tyr Val Ser Gly Pro Gln Ser Ser Asn Ala Cys Glu
                85                  90                  95

Ser Ala Lys Ala Gln Arg Lys Gln Val Tyr Asp Ala Ala Gly Leu His
            100                 105                 110

Arg Ser Tyr Glu Ile Ser Ser Tyr Trp Asp Asn Val Val Gln Asn Ala
        115                 120                 125

Cys Lys
    130

<210> SEQ ID NO 9
<211> LENGTH: 127
<212> TYPE: PRT
<213> ORGANISM: Bacteriophage Cf1c

<400> SEQUENCE: 9

Met Thr Leu Asp Thr Tyr Asp Arg Val Asp Leu Thr Gly Pro Trp Ala
1               5                   10                  15

Gly Phe Gly Phe Gln Gly His Arg Phe Phe Thr Pro Glu Asn Tyr Asp
            20                  25                  30

Ile Glu Pro Cys Asp Met Arg Tyr Trp Ala Leu Thr Cys Ala Ile Ala
        35                  40                  45

Arg Glu Trp Ser Leu Leu Met Ser Glu Glu Arg Asn Ala Arg Ser Ala
    50                  55                  60

Asn Pro Arg Lys Pro Thr Ala Thr Arg Ser Pro Gly Ser Arg Leu Ser
65                  70                  75                  80

Arg Gly Ala Asp Val Ile Tyr Leu Arg Asp Val Leu Leu Gln Arg Arg
                85                  90                  95

Glu Lys Arg Leu Ser Val Val Asp Gly Ala Gly Ser Ala Asp Arg Ala
            100                 105                 110

Gln Val Val Arg Arg Thr Arg Gly Pro Arg Ala Pro Arg Arg Gly
        115                 120                 125

<210> SEQ ID NO 10
<211> LENGTH: 166
<212> TYPE: PRT
<213> ORGANISM: Bacteriophage Cf1c

<400> SEQUENCE: 10

```
Met Tyr Ser Phe His Cys Pro Leu Cys Gln Glu Lys Pro Val Met Asp
1               5                   10                  15

His Val Asn Asn Leu Leu Asp Thr Val Arg Lys Ser Cys Ala Ile Pro
            20                  25                  30

Ser Asp Asn Met Leu Ser Lys Lys Ile Gly Val Thr Arg Ala Leu Ile
            35                  40                  45

Ser Gly Trp Arg Val Gly Arg Tyr Pro Val Pro Asp Ala Arg Ile Ala
50                  55                  60

Glu Leu Tyr Ala Met Ala His Leu Asp Gly Glu Trp Met Ala Lys
65                  70                  75                  80

Ile His Ala Glu Ala Ala Ser Pro Ala Glu Lys Ala Leu Trp Arg
                85                  90                  95

Ser Val Leu Asp Arg Leu Ser Ala Ala Ala Val Val Ala Leu Leu
            100                 105                 110

Val Leu Ala Val His Thr Gly Ala His Glu Ala Leu Leu Ala Ala Leu
            115                 120                 125

Ser Pro Val Ala Val Thr His Pro Leu Tyr Ile Met Arg Ser Val Leu
            130                 135                 140

Leu Thr Leu Leu Cys Ala Leu Ala Ala Tyr His Cys Trp Ser Leu His
145                 150                 155                 160

Arg Lys Arg Thr Gly Gln
                165
```

<210> SEQ ID NO 11
<211> LENGTH: 344
<212> TYPE: PRT
<213> ORGANISM: Bacteriophage Cf1c
<220> FEATURE:
<221> NAME/KEY: misc_feature
<222> LOCATION: (95)..(95)
<223> OTHER INFORMATION: Xaa can be any naturally occurring amino acid

<400> SEQUENCE: 11

```
Met Ala Asp Gly Thr Cys Ser Phe Cys Gly Asp Thr Thr Ala Tyr Phe
1               5                   10                  15

Phe Pro Gly Gly Leu Cys Val Ala Cys Thr Ser Lys Asn Ala Arg Ile
            20                  25                  30

Arg Met His Glu Gln Pro Thr Gln Ser Arg Glu Leu Ser Ala Phe Asp
            35                  40                  45

Ala Ser Val Gly Val Met Gln Ala Ala Thr Arg Arg Thr Glu Ile Ala
50                  55                  60

Ala Glu Lys Ile Gln Lys Asn Lys Arg Val Val Gly Thr Ser Val Arg
65                  70                  75                  80

Glu Phe Asp Ala Ala His Pro Ile Ala Leu Thr Ala Glu Gly Xaa Ala
                85                  90                  95

Leu Ala Leu Gly Leu Val His Tyr Lys Thr Ser Asp Thr Arg Ala Ser
            100                 105                 110

Thr Thr Gly Thr Val Thr Ile Glu Ile Asp Pro Leu Gln Ala Arg Ala
            115                 120                 125

Gln Arg Leu Arg Lys Ser Val Ile Thr Gly Ala Arg Leu His Asp Gln
            130                 135                 140

Glu Ala Lys Lys Gly Ser Phe Arg Gly Ala Trp Tyr Phe Leu Thr Leu
145                 150                 155                 160

Thr Tyr Arg Asp Gly Ser Asp Ser Ser Pro Arg Asp Val Ser Glu Leu
                165                 170                 175

Phe Lys Arg Met Arg Gly His Phe Asn Arg Leu Lys Ser Gly Arg Ala
```

```
                    180                 185                 190
Arg Trp Asn Arg Glu Ser Phe Arg Tyr Val Trp Val Gly Glu Leu Thr
            195                 200                 205

Gln Arg Phe Arg Pro His Tyr His Val Met Leu Trp Val Pro Thr Gly
        210                 215                 220

Met Tyr Phe Gly Lys Val Asp Gln Arg Gly Trp Pro His Gly Thr
225                 230                 235                 240

Thr Gln Ile Glu Lys Ala Arg Asn Cys Val Gly Tyr Leu Ala Lys Tyr
            245                 250                 255

Ala Ser Lys Phe Thr Ala Leu Thr Ala Gly Ala Phe Pro Lys Gly Phe
        260                 265                 270

Arg Thr His Gly Ile Gly Gly Leu Asp Thr Glu Ser Lys Arg Glu Leu
    275                 280                 285

Pro Trp Trp Lys Ala Pro Lys Asp Ala Arg Glu Ala Leu Gly Gly Glu
        290                 295                 300

Ala Asp Ile Arg Lys Ala Lys Gly Gly Trp Phe Asp Arg Leu Thr Gly
305                 310                 315                 320

Glu Phe Trp Pro Ser Pro Trp Lys Val Thr Phe Ile Phe Gly Arg Thr
                325                 330                 335

Phe Ala Trp Lys Val Val Pro Leu
            340

<210> SEQ ID NO 12
<211> LENGTH: 166
<212> TYPE: PRT
<213> ORGANISM: Filamentous bacteriophage Cf

<400> SEQUENCE: 12

Met Tyr Ser Phe His Cys Pro Leu Cys His Val Asn Asn Leu Leu Asp
1               5                   10                  15

Thr Val Gln Glu Lys Pro Val Met Arg Lys Ser Cys Ala Ile Asp Pro
            20                  25                  30

Ser Asp Asn Met Leu Ser Lys Lys Ile Gly Val Thr Arg Ala Leu Ile
        35                  40                  45

Ser Gly Trp Arg Val Gly Arg Tyr Pro Val Pro Asp Ala Arg Ile Ala
    50                  55                  60

Glu Leu Tyr Ala Met Ala His Leu Asp Gly Gly Glu Trp Met Ala Lys
65                  70                  75                  80

Ile His Ala Glu Ala Ala Ala Ser Pro Ala Glu Lys Ala Leu Trp Arg
                85                  90                  95

Ser Val Leu Asp Arg Leu Ser Ala Ala Ala Val Val Ala Leu Leu
            100                 105                 110

Val Leu Ala Val His Thr Gly Ala His Glu Ala Leu Leu Ala Ala Leu
        115                 120                 125

Ser Pro Val Ala Val Thr His Pro Leu Tyr Ile Met Arg Ser Val Leu
    130                 135                 140

Leu Thr Leu Leu Cys Ala Leu Ala Ala Tyr His Cys Trp Ser Leu His
145                 150                 155                 160

Arg Lys Arg Thr Gly Gln
                165

<210> SEQ ID NO 13
<211> LENGTH: 44
<212> TYPE: PRT
<213> ORGANISM: Bacteriophage Xf
```

```
<400> SEQUENCE: 13

Ser Gly Val Gly Asp Gly Val Asp Val Ser Ala Ile Glu Gly Ala
1               5                   10                  15

Ala Gly Pro Ile Ala Ala Ile Gly Gly Ala Val Leu Thr Val Met Val
                20                  25                  30

Gly Ile Lys Val Tyr Lys Trp Val Arg Arg Ala Met
            35                  40

<210> SEQ ID NO 14
<211> LENGTH: 95
<212> TYPE: PRT
<213> ORGANISM: Bacteriophage phiLF

<400> SEQUENCE: 14

Met Ala Val Ala Cys Gly Gln Asp Gly Val Ala Gly Asp Cys Arg Phe
1               5                   10                  15

Leu Gly Asp Leu Phe Val Met Trp Leu Glu Gln Ser Leu Ser Ala Ile
                20                  25                  30

Leu Tyr Val Leu Thr Leu Leu Pro Met Pro Asp Phe Met Lys Gly Gln
            35                  40                  45

Ser Ile Gly Gly Met Leu Gly Asn Ala Gly Ser Thr Ile Leu Trp Phe
    50                  55                  60

Ala Asp Val Phe Met Ile Gly Pro Ala Leu Val Met Ile Gly Ala Ala
65                  70                  75                  80

Met Ile Phe Phe Leu Leu Arg Arg Val Leu Thr Leu Gly Ile Trp
                85                  90                  95

<210> SEQ ID NO 15
<211> LENGTH: 42
<212> TYPE: PRT
<213> ORGANISM: Bacteriophage phiLF

<400> SEQUENCE: 15

Met Gly Asp Ile Leu Thr Gly Val Ser Gly Ala Glu Ala Ala Thr Ala
1               5                   10                  15

Met Ile Ala Ala Ala Ile Ile Ala Leu Val Gly Phe Thr Lys Trp
                20                  25                  30

Gly Ala Lys Lys Val Ala Ser Phe Phe Gly
            35                  40

<210> SEQ ID NO 16
<211> LENGTH: 73
<212> TYPE: PRT
<213> ORGANISM: Bacteriophage fd

<400> SEQUENCE: 16

Met Lys Lys Ser Leu Val Leu Lys Ala Ser Val Ala Val Ala Thr Leu
1               5                   10                  15

Val Pro Met Leu Ser Phe Ala Ala Glu Gly Asp Asp Pro Ala Lys Ala
                20                  25                  30

Ala Phe Asp Ser Leu Gln Ala Ser Ala Thr Glu Tyr Ile Gly Tyr Ala
            35                  40                  45

Trp Ala Met Val Val Val Ile Val Gly Ala Thr Ile Gly Ile Lys Leu
    50                  55                  60

Phe Lys Lys Phe Thr Ser Lys Ala Ser
65                  70

<210> SEQ ID NO 17
```

```
<211> LENGTH: 74
<212> TYPE: PRT
<213> ORGANISM: Bacteriophage If1

<400> SEQUENCE: 17

Met Lys Lys Ser Val Val Ala Lys Ile Ile Ala Gly Ser Thr Leu Val
1               5                   10                  15

Ile Gly Ser Ser Ala Phe Ala Ala Asp Asp Ala Thr Ser Gln Ala Lys
            20                  25                  30

Ala Ala Phe Asp Ser Leu Thr Ala Gln Ala Thr Glu Met Ser Gly Tyr
        35                  40                  45

Ala Trp Ala Leu Val Val Leu Val Val Gly Ala Thr Val Gly Ile Lys
    50                  55                  60

Leu Phe Lys Lys Phe Val Ser Arg Ala Ser
65                  70

<210> SEQ ID NO 18
<211> LENGTH: 82
<212> TYPE: PRT
<213> ORGANISM: Bacteriophage Ike

<400> SEQUENCE: 18

Met Arg Val Leu Ser Thr Val Leu Ala Ala Lys Asn Lys Ile Ala Leu
1               5                   10                  15

Gly Ala Ala Thr Met Leu Val Ser Ala Gly Ser Phe Ala Ala Glu Pro
            20                  25                  30

Asn Ala Ala Thr Asn Tyr Ala Thr Glu Ala Met Asp Ser Leu Lys Thr
        35                  40                  45

Gln Ala Ile Asp Leu Ile Ser Gln Thr Trp Pro Val Val Thr Thr Val
    50                  55                  60

Val Val Ala Gly Leu Val Ile Arg Leu Phe Lys Lys Phe Ser Ser Lys
65                  70                  75                  80

Ala Val

<210> SEQ ID NO 19
<211> LENGTH: 82
<212> TYPE: PRT
<213> ORGANISM: Bacteriophage Pf1

<400> SEQUENCE: 19

Met Lys Ala Met Lys Gln Arg Ile Ala Lys Phe Ser Pro Val Ala Ser
1               5                   10                  15

Phe Arg Asn Leu Cys Ile Ala Gly Ser Val Thr Ala Ala Thr Ser Leu
            20                  25                  30

Pro Ala Phe Ala Gly Val Ile Asp Thr Ser Ala Val Glu Ser Ala Ile
        35                  40                  45

Thr Asp Gly Gln Gly Asp Met Lys Ala Ile Gly Gly Tyr Ile Val Gly
    50                  55                  60

Ala Leu Val Ile Leu Ala Val Ala Gly Leu Ile Tyr Ser Met Leu Arg
65                  70                  75                  80

Lys Ala

<210> SEQ ID NO 20
<211> LENGTH: 44
<212> TYPE: PRT
<213> ORGANISM: Bacteriophage Pf3

<400> SEQUENCE: 20
```

```
Met Gln Ser Val Ile Thr Asp Val Thr Gly Gln Leu Thr Ala Val Gln
1               5                   10                  15

Ala Asp Ile Thr Thr Ile Gly Gly Ala Ile Ile Val Leu Ala Ala Val
            20                  25                  30

Val Leu Gly Ile Arg Trp Ile Lys Ala Gln Phe Phe
        35                  40
```

<210> SEQ ID NO 21
<211> LENGTH: 73
<212> TYPE: PRT
<213> ORGANISM: Bacteriophage f1

<400> SEQUENCE: 21

```
Met Lys Lys Ser Leu Val Leu Lys Ala Ser Val Ala Val Ala Thr Leu
1               5                   10                  15

Val Pro Met Leu Ser Phe Ala Ala Glu Gly Asp Asp Pro Ala Lys Ala
            20                  25                  30

Ala Phe Asp Ser Leu Gln Ala Ser Ala Thr Glu Tyr Ile Gly Tyr Ala
        35                  40                  45

Trp Ala Met Val Val Val Ile Val Gly Ala Thr Ile Gly Ile Lys Leu
    50                  55                  60

Phe Lys Lys Phe Thr Ser Lys Ala Ser
65                  70
```

<210> SEQ ID NO 22
<211> LENGTH: 84
<212> TYPE: PRT
<213> ORGANISM: Bacteriophage I2-2

<400> SEQUENCE: 22

```
Met Ser Val Ile Thr Lys Val Ala Ala Ala Lys Asn Lys Ile Val Val
1               5                   10                  15

Gly Ala Gly Leu Leu Met Ala Ser Ala Gly Phe Ala Ala Asp Asp
            20                  25                  30

Gly Thr Ser Thr Ala Thr Ser Tyr Ala Thr Glu Ala Met Asn Ser Leu
        35                  40                  45

Lys Thr Gln Ala Thr Asp Leu Ile Asp Gln Thr Trp Pro Val Val Thr
    50                  55                  60

Ser Val Ala Val Ala Gly Leu Ala Ile Arg Leu Phe Lys Lys Phe Ser
65                  70                  75                  80

Ser Lys Ala Val
```

<210> SEQ ID NO 23
<211> LENGTH: 1018
<212> TYPE: DNA
<213> ORGANISM: Bacteriophage phiLF

<400> SEQUENCE: 23

```
gatatccgca aagcaaaggg cggatggttc gacaggctta ccggagagtt ctggccgtct      60
ccgtggaaag tcacattcat tttcggccgg acattcgcct ggaaggtagt ccaactatga     120
aagtgcagat catgagttcc gctgtcgctg ttcgttcgtt ccccgcgcgc gagggtaagc     180
ccgcgacgca tttccgtgag cagaccgccg ctgtgctgcg tgagggcgat ttcccactgc     240
cgttcaccat cggtctggac gaggatcaac cgccgtatgg cgagggcttc tacatcatcg     300
atcccaagtc gttgcagaac aataaattcg gcggtctcga gttcggccgt cgcattcgtc     360
tgattccgga cctcactgcg aagctgcaac agcagcccgc aaaggtcggg tgattcatgg     420
```

```
cgatgtgcgt agccctgcaa gtggatggca cgttggtgcc caccggccaa tcggtcggcg    480
agtgcagcgg ctacgtgctc gtcagtggta gcgaatacag cgtgtatgcg ctggtgcaag    540
aagcgttcgc aatgcccagc caggaggacg ccgtagcgtg gtccaccggc tgctgtggcc    600
tggtgatcgt gtggttcgtc ctggggcgcc ttgccggcag cgtcgcgggc atgttcaacg    660
accggtaaat caatcaatca aataggagag acaacatggg tgacattctg actggcgtga    720
gcggtgctga agctgctacc gcgatgatcg cagcggccgc aatcattgcc ttggtgggct    780
tcaccaagtg gggtgccaag aaggttgcaa gcttcttcgg ctaatggtgg tgagggcagg    840
gcggcgcttc ggtgtcgccc tctctctttc tggggtgggg cgatgattat tttgttgttc    900
tgtggattca tgggcgcgct gtgcggttgg gcaggcgtca aggggttgga cgcgtgattc    960
gcgtttcgtt ggcaatgctg attcttttag cgctcacgtt ctctcctatc gtgcatgc    1018

<210> SEQ ID NO 24
<211> LENGTH: 7325
<212> TYPE: DNA
<213> ORGANISM: Bacteriophage XacF1

<400> SEQUENCE: 24
atgctgctga tgcacgtgac gctgccatgg agttctatcg tggctgatgg cacctgctcg     60
ttctgtggcg acaccactgc ctactttttc ccaggcggtt tgtgcgttgc atgcacctcg    120
aagaacgcac gcatccgcat gcatgaacag cccacgcaat cgcgtgagtt gtccgcgttc    180
gatgcatctg tgggcgtcat gcaggccgcg acgcgccgca ccgaaattgc cgcagagaag    240
atccaaaaga caagcgcgt ggtgggtacg agcgtgcgtg agttcgacgc tgcccatccg    300
atcgcattga ccgctgaggg ccagcgcgca cgctggccc ttgggcttgt ccattacaaa    360
acaagtgaca cgcgggcctc tactacaggc accgtgacca tcgaaatcga cccgctgcaa    420
gcgcgggcgc aacggctgcg taagtccgtg attaccggag cacgtctgca tgaccaggaa    480
gcgaaaaaag ctccttccg gggtgcgtgg tatttcctca cgctcaccta ccgtgatgga    540
agcgacagca gccctcgtga cgttagcgaa ctatttaaac gcatgcgcgg ccacttcaat    600
cgccttaaat ctgggcgcgc acggtggaac cgtgaaagct ttcgttacgt atgggtcgga    660
gaactcaccc agcgattccg tccgcactac cacgtgatgc tgtgggttcc cactggcatg    720
tatttcggca agtcgatca cgcggttgg tggccacatg gcacaacgca aattgagaaa    780
gcccgaaact gcgtcggcta tctcgcgaaa tacgcgagca agttcactgc ccttacagct    840
ggagcttttc ccaaaggctt ccgcacacat ggcattggtg gactcgatac cgaatccaag    900
cgcgagttgc gctggtggaa ggccccgaaa gacgcgcgtg aagctctcgg cggggaagcg    960
gatatccgca agcaaaggg cggttggttc gacaggctta ccggagagtt ctggccgtct   1020
ccgtggaaag tcacattcat cttcggccgg acattcgcct ggaaggtagt cccactatga   1080
aagttcagat catgagttcc gctgtcgcca tccgttcgtt ccggctcgc gatggtaagc   1140 cagcaacgca tttccgcgag cagaccgccg ccgtgttgcg cgagggcgat ttcccgctgc   1200
cgttcaccat cagccttgat gaggatcaag cgccgtatgg cgaaggtttc tacgtcatcg   1260
atcccaagtc gatgcagaac aacaaatacg cggcctgga attcggccgt cgcatccggc   1320
tgatccctga tgcaaccgcc aaagctgcgc agcctgctgc acgtgtctcc taacccagat   1380
gcatgagagc agggattctg agcaatggca aaggtcctga cctgcacgca atacaacgat   1440
tcaacgcagc aatgcgaggt ccaagcctgg attgatcaat cggattggac gacaccactt   1500
cccaccatcg aacaggccgc gatggtgggc ggcgcttact tcatcggcct gatgacccctt   1560
```

```
gcagtcatta aaggactgct caacccaaaa tcaatagagg aatagcatca atggaaaaga    1620
acatttcgac cgttgtcacc aaggctaagt cggctgtcag caacgccaag accgccgcaa    1680
ttctgggtag cactgccttg atggccatgc ccggtttcgc cttcgcgtcc ggtggcggcg    1740
gcgacttcga cggcaccgca atcatcggca aggtgactac ctataccgcc atcggcgtga    1800
ccattctggc cgccttcgcg ctcggtcgtt ggacgcttcg cgcactcggt ctgatcggcg    1860
gcaagtgagc caatcagcgg catagcaggg gaggggaaac cctcccttt tcaatggggg    1920 atacgcaatg gaaggattga tcgtgttggt gttcctgatc catgccgcgc acgtgtgcgc    1980
aacgggctgg aactgatgcg cgggctcggc ggatatttcg cacgcgctgt agttcggcga    2040
attgcctacg ttgtagtcgc ggcgtgcttc ggcctacttt tgcaattgtg cagtgggagt    2100
gcgcacgcgg ccgttgatca gggtgaggcg tactcgcttt gcatgaaatt cgctagcgat    2160
atggtggcga aaaatccgga catgcgacga aacccctcgt gcccgtcgcg tagggcattt    2220
caatacacct gccaatatga agccattccg tatgtaggcg cttcgcagtg gtccgtagat    2280
acttgcggcg actacagcta tgacgatcag tacacatgcg catcgcgtaa ctcgaacaag    2340
cttgctgatg ccgcaccgtg gtacacccct ccgcctaact gcatatccgg ttgtcaagtg    2400
caaggcactt cgttcagtgg cgacaacggt ggcgtcaaga cctatggaat gaaggaccgt    2460
acctataacg gttctatctg taccccctacc aagcccacca acgatatcgg tgaattgcag    2520
gaggaaaaga acgacgccac caaggaaaaa gcgcctgagt gcaccgcgct cgggtctggg    2580
cagaccgctt gtttgaagcc aaacggcgac tattgcgcaa cggcgtcatc cggcaagacg    2640
ttctgctgga agcctgccga cacgggcaaa aaaactgacg ctactgatgc gcaaagcaag    2700
actccaaagg gcgacccctgt aacgccgcct cctatcccgc ccccggatgg tgaatggcag    2760
cgcaaggaag gccaccagca gacccacgtgc gtgaacaata cgtgcactac ctacaacgtt    2820
accaactaca cgaccgtgcc ttccggcacg tccaagaacg gcacgggtga caacagcgcc    2880
gatggctcgg gcaacacatc tggcaatggc agcaatagcg gcacggggaa gaaggacgac    2940
gacagcaagg atagtgctac ggatagcggc aattgcgatg ccccacctat ctgtgtgggc    3000
gacacgttga agtgtttgca attgaaattc acatggaaaa tcgattgcaa cacacgcggc    3060
aatgagatca ctcaaggcga ttcatgtgct gatggtgatg tgcctgtctg tgctggcaag    3120
tcgtgtaaag ccgaggccta cgcgcaggtg gtacagcagt ggaaacaacg ctgcgctgta    3180
gaggcgatgg ggcagggat ggcctcgcgt gccgctgcta ttagcaatgg tgacgatgct    3240
ggtgtggttg agggaatctg gggcggtgaa tctgccggcg ccggccttaa gttgcgccag    3300
gatttggtca acgttggcgg caatggtact ggcggcttgt tgcccgacgt tgatatcgaa    3360
ggtcaacact ggaccgtacc ctctggattt ttcgacgcaa ttgctgcggt caagatggtc    3420
atcatcgcga tgtgcacagt gatcgccatg ttcgtcgttg ggaggaacat ctaatgttcg    3480
attgggcacg tgactttgcg aacaatttct ttgagaacgc cgcagatgcg gtccataagt    3540
tggtcaagct caaggccgct atatggctcg gccgattgct gtccgctctc ggtctgggtt    3600
tcgccgcgca gcatttcatc tacaacccga tcatcgaata cgcacagaac gcatggtcgt    3660
ccgttcctgc gggcatcgct gcatgggtac acgcattggg catcgatgca ggcgtgtcga    3720
tcatcctgag tgcctatggc attgcgggtg cggagcgcat ctttattcaa cgtaggaacc    3780
aagcaacatg atcggcgaca ccgcgtctat ttcactgctc accggcttgc caggatctgg    3840
caagagcttg cgcattatcc aggcgattcg ctatctcatg gacaagggtg cgcacgtcta    3900
```

```
cgtgtgcaac atcgacggca tctccgtgcc cggcacgacg ccgtgggctg atccgcataa   3960
gtggcaagat ctaccggctg ggtcaattct tttcgttgat gaggcgcagc attttttccc   4020
cgcacgtcgt ggcggggatc cggtcgaaac gatcaaggcg atgtccacga ttcgacacga   4080
cggcgtgcgt ttggtgcttg ccacgcagca gccgaactac ctcgacacct atctgcgtgg   4140
attggtcggc tatcacgaac acctgctgcg tcagagcggc aaacagaaga cctttatttt   4200
ccgcaatagt cagatcatcg aagaggtgcg gtcgccgttg ccgcgcatca aaaagctcta   4260
cgactacgaa gtgtggaaac agccaacaga gtgcttcaag ttctacaagt cggctgaggt   4320
ccacacgatg aagtatcaga tgccggcact ggtgaaaaag gcattgatga tccttcctgt   4380
cgtcgcactt ctggctggcg gcgcgtggta cgccgtctac cgcgacacca tgttcgccaa   4440
gaaagcagac gctgcgcccg ccaataagac ggccccctcg gggccgtcgc tggcgggcac   4500
tgcgtctgcg ggtgcagcag ctcgtcccaa ggtcaacagc gcagaggact acgtcggtca   4560
gcttgtgcca ttggtcgccg atgtgccttg gtcggcacct gcctacgtgg atcgccctgt   4620
ggtgtccgat ccccatgtgt attgcatggc aactgagaac acctgtcgat gtgtcactga   4680
gcaaaattcg cgcgttgtga tgcgcgatga cgtgtgccgc gacattgcgc ggtggggcga   4740
gccatataac ccgtataagc cgccgcatag tccggcgcaa aagcagcagg attccccggt   4800
tgcagaagcc acgcagccta agccccaggt gccccagcag agcggggcag tgtcgtcgtc   4860
cgtgcaaagg gccacacgct cccttggcac gttccccgaa tcgccgcctt accagacgac   4920
aacgtacacc ccacccacca ccagggatct gtgatgagca gtagtgcacg cgagttactg   4980
aagtggattg cgcttgtctg catgacattc gaccacgttg ccaaggtgtt ctatgacggc   5040
tacgtgcccg tgttgtccga gctaggccgg attgcgtttc cgctcttcgc actggtcatg   5100
gcctacaacc tggcacagcc tggagctgat gtaggcaagt cggtccgccg gctggtgtgc   5160
tgggggctgt tggcgcaacc gttccacgcc tgggcgtttg gctactgggt gcccgtgaac   5220
gtccttctgg cgttcgccct ggctgctgcc gctgtctggg ctatccagcg cggccgctgg   5280
gtgctgctga tgctctgtgc cgctccagcc ccgttgttcg tcgactacca atggactggc   5340
attgcgctgg tggtggcagg ctgggcctat tacgccaaag tgatgcgtag ccctataccg   5400
gtcgtcatgg cactgggcgc tctatgttgg ttcaacggca gcttgtgggc ccttcttgcc   5460
atcccaatca ttgccctctc agaagcggtc accaatcgag gtatggctat tcctcgcacg   5520
cgccttggct tctacggcta ttatgtgggg catctagcta tcttgggtct gctggccctc   5580
aagcccgccc ttatttcgtg acgcgagggg aagtgcatgg aagcgagatt tgcaatgttg   5640
cttgcgctgg ctatcgttgt tccttgtcac gcgcagcagg ttcacaagtg ccgtgagcga   5700
gggcaggtcg tttatcagtc agcgccgtgc gcttccggcc aagcccagaa ggtctgggac   5760
gccgcaccag ctcctgagca aagcaatgcc gagcagtggc gcctttaccg tattcgcaag   5820
cagctcgata gcaggtacgc agctgacaga tctgcatccg ctgccgccta tgtgtctggc   5880
ccacaatcca gcaacgcatg cgagtctgcc aaggctcagc gcaagcaagt ctatgacgcg   5940
gccggtctcc atcgttctta tgagatttcc agctattggg acaacgtggt gcaaaacgcc   6000
tgtaagtgac ctgggtgta ggggcatagc ccctacggat aacgcctcac ccgcgccgtg   6060
gagctcgagg cccacgcgtt ctacgcacca cctgtgctcg atcggcggac cccgcgccat   6120
ccaccactga caaccgcttt tcgcgcctct gcagcagcac gtcccgcaga tagatcacgt   6180
ctgcgcctcg agacaaacga gaccctggag atccttgtgg agtaggcttt cgaggattcg   6240
ccgatcgcgc attgcgttct tctgacatca acagtgacca ttcccgtgcg atcgcgcatg   6300
```

```
tcagcgccca ataccgcata tcgcacggtt cgatgtcgta attctccggg gtgaagaacc   6360
ggtgcccctg aaaaccaaaa ccggcccaag ggccggtcag gtctacgcga tcgtaggtgt   6420
ctagcgtcat tgtccagtcc gcttcctgtg gagggaccag cagtgatagg ccgccagggc   6480
gcacagcagc gtcaacagca cacttcgcat aatgtataga gggtgggtaa cggctaccgg   6540
cgagagggcc gctagcagcg cctcatgcgc ccctgtgtgt accgccagga ccagcagcgc   6600
gaccaccgcg gcggccgcgc ttagcctgtc caacactgat cgccatagcg cttttcagc    6660 cggcgatgcc gctgcttcgg cgtgaatttt cgccatccat tcgccgccat ccagatgtgc   6720
catagcgcat agctctgcaa ttcgtgcgtc aggaaccggg taccggccaa cgcgccagcc   6780
gcttatcagc gcccgcgtca ctccaatttt tttgctcaac atgttgtctg acggtatggc   6840
gcacgacttg cgcacggtgt caagcaaatt atttacatgg tccatgacgg ttttttcttg   6900
acagagagga cagtgaaaac tatatatgct cccgtgctta ggcaacccta agtaccgcgc   6960 accccccggct cccctccggg gtccgcgtca aggggcaggg gaggggggcta caccgtgcat  7020 ccatattcga tcctgggcca gcttttggcg ctgcacattc tcgtgtcgat ctgcgtgctc   7080
accgggtacg caatcgtcgc tgtgatctgt tggtgtcttg atcgcaagca cgacgcgatg   7140
gttgctcaaa ttgagcaagc cgcattggtc gctatcgcat atcgcgaggt cgtcgtggc    7200 tgagtctcga tctgttgcat ggatgattgc gccagctcga gtgcagggcg gcccccgcat   7260
ttacgtcttg accatcgtcg tcaacggcaa cgctgttgaa cagagctatt ttgcatcgcg   7320
caccg                                                               7325
```

<210> SEQ ID NO 25
<211> LENGTH: 6468
<212> TYPE: DNA
<213> ORGANISM: Bacteriophage Cf2

<400> SEQUENCE: 25

```
tatattatgt caaagcgcgt gcggcgcttg ttgcgctcgt ttgttgctgc gctcacaccg     60
tgggggcgac gatggcccgc cggatggaga tcggtgcatg cgtaatcgaa cactgaccgg   120
ccaatgggcc ggttttcgt tccagaacgg atacctcatt acaccagagg gccgagccat    180
ggagccgtgg cagctcagct acctatcact gacctgcgat atcgcacgcg agtggacgaa   240
gatgatggcc gagggacggt cgaaaacccg gccaaaacgt ccagcgaacg tcattttcat   300
tagggatcgg ttcagaaaaa agattgaaac aaagcccggt cctcaggtgg tggctaccgg   360 cttttgcggcg gaatgcgcag gatcatcgtt gccgaaggcg cggaaacgta aaggccgcgt   420
atgaagcgtt acacgtaggg gcgatgcccc tacaccccta caatgccggc tcatcatcat   480
cgggggccgt atgagctaca gaccgcaaaa caaccacgag ggactctggt gggaaatagc   540
cctgggcatc ttcgtcggcc agctgatgac cgcagcactt gccggcgtgg tggcgctgtg   600
cctgggctac ttcaccatgc gcagtgtcag cgcagcgcta cccgcaggcg caccgcaacg   660
gctatacacg ccccgctcgc agcgcgtggt accggaaccg ctgcaactac gcgaactgga   720
atcaaacgag cgatgcattc aacacaagcg attccggcgc ctgtccaatg gctggcaaga   780
attgccaaac gatccgtgct gaatcgtgac gcgtcacgaa actacatatc caacgtggta   840
gccggcgtgc ttgtggtcgt ctgatagggc ttgcttttccg gaacgtgcc gaggctgcgc    900 ggaacatgcc caatcacggc acttctttgg tgatcgcgat cagcgccacc ggcgtcactc    960
cctgcggtcg caacgccagc agcgccgtcg ctcttgccat cagacgcggt gttatagagg   1020
```

```
cgtggatcct gctcgcgcac cggctcgcgc cacggccacg gagtagcgac caagacgtgt    1080
ttgccagcaa ccagacgcat gccataggga accatcgtga cggaatagcc aagcgcccgc    1140
agctggtcaa tatcaagctg ttcaatgaca ttgttagacg tatcaatcca atgcacccag    1200
gcacgctcat ctgatcccac acgcgcacgc gcagccaaac gaatgcgccc tttctcggcc    1260
agctgcgcaa cgtaccgctg ctcatcggtc aaatcggcaa gcggatcagg cggcggagct    1320
tgaacagcac cactaggcgc accattggcg agaccagccc ccacacttgc cttatcggac    1380
tgctgccaaa ccgtcgcccc tgccgccgca ggcttatgcg tctcctgctt gcccttgctg    1440
aaaaagccag cgaagaaata cagaccaaca ccaccgacaa cgaggaagat caccgcacgc    1500
accgccatcg cagcccatac gttttgccg ccctcttcgt agacctcagt attctcagcg    1560
ccaggcgcat acccgtcata gagcggaaaa atcacgggat cgtacttgag cgtctgacca    1620
ccgacctttt cgaatttacc gggcgaggtc gtgtggaaat acgtcacgcg ataccggctt    1680
ttcatgccga cagcagtgag cttctgaaac gtgttttct tctcgatacg tgctttgacc    1740
gctgaatgca agcggttgat ccactgcgtc atgatgaccg catcgccacc gttctgacca    1800
agcagcgccc agaaattctc aacagccggc tcaagcggct gcgctcatt gacgtagaac    1860 tcgtggacct catcgatcac aactaacgcg tctttgaact catcgggaat acaccacttg    1920
ccggacgcat cttgcgtgca cgcaaagagc ttcgccacgt ccttcgtgtc aacaagcacg    1980
aggcagtgct gaacgtcctt ttcctccatg ccaagatgct tggcaatgcg gtcatggcgt    2040
aagccgttca gacgcgcaaa gacgcgacga cctttttga tcgcaggcaa gatgtgattt    2100
ttaaccgcgt cgtagctctt gccggcgcgg ggcacacctt cgttgaaaac gagcatgtca    2160
ccaaatccca agcgtcagga cacgacgcag caagtagaaa atcatggcgg cacccacagc    2220
cacgagcgac ggaccaatca tgaaaacgtc agcgaaccag aggattgtac tgccagcgtt    2280
tcccagcatc gcgccaatgc tctggccttt catgaagtcg ggcatcggca agaggctcaa    2340
gacatacaag atcgccgaca cgactgttc caaccacatc acaaacaaat cgccgatgaa    2400
atcagcaaac gcctgccaaa ccgccttgac cgctctccat atccaggctg tcagatcggt    2460
gaaccaacca gcgtacatgc cctgcccctt atgtcacggc gatgcggatg ccgcatacg    2520 cagcaatcgc caaaatgacc catccacacg cacgcaaaaa cgtgaggaat gtgccgctac    2580
agtgaaaatc aatcatcatg gcatcccacc acttcgacgc acccaggcta aacaccggac    2640
acgaaccacc agacggaacc gtcatgaagc ttgcaatccc gccagcaaga ggtgtggcgc    2700
gaacctgcgt tgcaaacctc gacacaacag actccactgt tttatcgctc ttggtgtaga    2760
ggtcgccgat cggcgaaccc tctcccggat cgtcgctatc cccatcaccg tcaccgtcgc    2820
cgtctccact tccagagcca ccgccagaac cgcctgaacc attgtctttg ccaccctcgc    2880
ccacgttgcc ctgcccccct ttgctgccgc tggaactcca cgtggtcgtg ttgtaagtgg    2940
tgttattgac ggtagtagtg gtgttggaaa cctccttagg gtctttcaga ttaggaggag    3000
gcgtcggcgt agcgggtgcc ttctgccgat caccggcata ggtgccatcg gcggtctgac    3060
gcgggcccgt tagctctggc ttccaacaca gcgtggagcc agcagcgccg gtgacacagt    3120
gggtgccgtc cgacctgatg cactcggcat aagcgccacc agtagacgaa cacgtctgct    3180
tgtcaggctc atggatgcca gacggaacag catcgccctg ttgacactcc tgaccagttg    3240
gcgaccagtt cttggcagcg cagtacaggt cagctccacc gcccatgcag acatcaacgc    3300
cgccagcgga attcattgtg tactggcact gattcgaaca cgcatagatc gaaccacgca    3360
ccgagacatt cgttagcgga ggcgcatttt tgcaattatt ctcgttgtca taggatagt    3420
```

```
caccacaggt gacaacagag actggacctt gatagtaagc agccgcgctg tattggcact    3480
ggtaatactt gccggtggcc tcagtaacct tatctacaca ggtgccagga ctggtgatga    3540
ggttcgtatc tttgacctga tacgcgcttg catcgttcat gcacttggca aatgcctgcg    3600
aacgcgaatc agcagcgtgc gcaggagaga tagcgcatag cgcaatcacg agtgtgcaca    3660
gcgccgaaag aatcactcgc atcatggtgc atccaaaccc ttgaccgctg cccatccaca    3720
cagcgcaccc ataaatgcac agaacagtag aacgatcatc gtgaccccca gaaagagaga    3780
gggcgacacc gaagcgccgc cctgccctca ccaccattag ccgaagaagc cggccacctt    3840
ctttgcaccc cacttggtga agccgaccag cgcgatcagc gcggcagcac ccacaacagc    3900
agtcacggca tcagccgcac tcagacccga cagaatgtca cccatgtttc tctcctcgtt    3960
gattgattga tttaccggtc attgaacatg cccgcgacgc tgccggcgag gcgtcccagg    4020
acgaaccaca cgatcaccac accgcagcag ccggtggacc acgcaacggc gtcctccttg    4080
ctgggcatcg cgaacgcttc ttgcaccagc gcatacacgc tgtattcgct accactgacg    4140
agcacgtagc cgctgcactc gccaaccgat tgaccagtgg gcaccaaggt gccatcggct    4200
tgcagggcga cgcacacggc cataaatcag cccttcgcag gctgatgcgc agccttggga    4260
gtgaggggga ccagatcgac gtaacgcttg agggtcaact caccgtagtt gccgatggag    4320
aaggccttcg ggtcgatgtc gtactcaccc ggctgatagg cggggcgctt gcccaagcca    4380
acacggaacg gaagtgcatg cccgttgcca aggtccaggc caaccgtctg accgcgcatc    4440
acctcgccgg ttttttggtt gacttcctct tcgacagcag cactcaagat gcggcagatt    4500
ggcatagttg ttccctcaca tatcgatgta gtggctcacc ctttgagata ccgcgaaacc    4560
gtccggggtg accttcacgg aggatgcggg cctcgcagac gtcggaccat gagtggccga    4620
acgcaccgcg tagaacattg agaaacgggc cgacctgacg atgcgcccat tcgatgccag    4680
cctccacgga cacatccacc tgcttgcgga tggtgcggag cctggtgcag atgccagtga    4740
tcaattcgcg cagcacgtcg tacgaaccgc gcagataagc gcctggatcg gtcagaacgt    4800
cgagtggaat ctcaacgtgc ttaccgtaga cacggacctc tgcgcgcacc cagcgcgacg    4860
ttttgaggcc catctgcttg cccttctcat agatgcacaa ttccttgtga cccttggcac    4920
cgacgtagag cgtcgagcct gtgccgtggc cctcatcgct caggaaacga tggcgcgggg    4980
ggcatccgcc ctggcagaac tccccatcgg cagcgcgctt gcgcagcaca tgcacgtcga    5040
ggcgctcgcc ttcgtaatcg tcgtgcgcac aatcgacacg gctgatgcgc gcacgcagga    5100
ttgaggcctg gcgctgcacg tgcgcccaat ccttgaccca cttgcagcct gcgcctgaaa    5160
gggaaacgca cacagtcgcc ttgttgccgc ccataccgat gcggcccacc aactcgccct    5220
cgcggtccat caagagggcc gagtggctgt agaacatcca gttcttgttg cgaagcgcag    5280
tggcaacgac ctcaccgcga aaccgaaga tgcggaacaa cagcaaatcg atgttggtgc    5340
agcgaaaatc ttctaaagca gtttcgggca tcacaagggt cagataatcg atgatgccgg    5400
tttcctgacc cttttggccc gtgttacttg tcgggccaat ttcccgacct ccgacctttt    5460
caccggcgcg gaccggggaa aagctgccag caaatgcgac gagcgcggtc acagagccac    5520
caacacggtg tgataggtgt cgatgtggga gacgacctca gtcatgacaa accccgctga    5580
aataggcgat cagaccggca ggcgtgagga acaagaacac gccacaaacc catgtccacg    5640
gctcaggcag gtagtaggca ccgatgatga aagagagat gaaggcagcg agcgcccaca    5700
cgtagccgat gcactttgcg aactccttca tgcgacgacc tccatttcac tttgggcgct    5760
```

| | |
|---|---|
| acaaatcgtg acgcgtcgcg aaatagtcgg cgcgaccaag tcaacgtagc tttcgatgat | 5820 |
| gaagacctgt tcgcggtgtg cgcgcagcgc agcttcggcg cgacggtcaa gaatccaagc | 5880 |
| gacgaatcgg gcgaggccga cgatcacggt cagcgcggag gcgccgatca gtgcaagtgc | 5940 |
| gtttgtgtcc atgaagcccc tatccctgc cccttgacgc ggaccccgga ggggagccgg | 6000 |
| gggtgcgcgg tgtatcgcgt ccggatacac ggggagcatg taaactcgtt ggagacagtg | 6060 |
| ctgtcaaccg gcgagataca tggacacatt aagcaaacta cttgacaagg ctcgcctaat | 6120 |
| gtgcgagcgg gattccgata actgcctagc gcagacgcta ggactgcaac gagcagccgt | 6180 |
| gtccaagtgg aggcatggag gaaagatcag cccggaagaa ctggcaaagc tggtcgtgct | 6240 |
| tgctcaggct gatccgggca tagccgtgct agttctgaat gaacaagcag acgatgcgac | 6300 |
| cgcgaaaaag ctctggggac cactatggga cagactgtcc ccggtcacta cggtgatcgg | 6360 |
| ggcgatggtg ctagcagtga cactaacgcc ggcgacagtg aaggcaaaag cctttgaaat | 6420 |
| caattacttg aacgagtcga gtgcgtatag tctgtatatt atgtcaaa | 6468 |

```
<210> SEQ ID NO 26
<211> LENGTH: 7205
<212> TYPE: DNA
<213> ORGANISM: Bacteriophage Xf

<400> SEQUENCE: 26
```

| | |
|---|---|
| tatacattat gcgaagtcgt actgttgacg ctgctttgca ccgtcgcagc ctattactgc | 60 |
| cggtccctcc acaggaagcg gactggacaa tgacgtttga cacctacgaa cgcgtagacc | 120 |
| tgaccggccc ttgggccggt tttggttttc agggacatcg attcttcaca ccagaaaatt | 180 |
| acgacatcga cccttgcggc atgcggtact gggcgctgac gtgtgccatc gcacgggagt | 240 |
| ggtcgctgat gatgtccgaa gaacgcaatg cgcaatcggc gaacccgcga acgcctactg | 300 |
| ccacaaggtc tccggggtcg cggatttctg aagacgccaa cgtgatctac ctgcgggacg | 360 |
| tcctctggcg caggcgtgaa aagcggttat cagtgggggg gaatccgggg ttagccgaca | 420 |
| gcggcaagcg cagcccgact ggacgggggc ggcggcgtcc acggcgcggg tgaggcgtta | 480 |
| tccgtagggg cgctgcccct acaccccggc tacatgcgaa ctgacagatc caggcgaaaa | 540 |
| gccgcgcccc tgtgactgcg ccccgcaggg gctgtcaacg aaaggtcgta ggcggcgtcg | 600 |
| tggtgttcgt ggtgtaggcc ttgttttccg agaacgtcat ctatctacgc gacgtgctgc | 660 |
| cgaaacgccg gcagcgacac aatgagcacc aacaggccga ggtggccaac gtaataaccg | 720 |
| tagaaagccc agcgcagccg agggagtggc caccacacgt acccaagcgc cagaacaggc | 780 |
| agagccgcca gcgcccacac gttgccgtta taccaacaca gcgcagccat gctggccagg | 840 |
| actccgacga gccattgcag gcggccgctg cggaacaagc cccatgctgc caggaccagc | 900 |
| aaaacgccga accactgata gtcaaccagc accgggacca ccactgcgaa cacgaacgca | 960 |
| tagagccagt gccgtgcgtg gacagtccac accagcagcg cagcacatgc gaacgtcaac | 1020 |
| agcacgttga gcgcagccca gtagccgaat gcccaggcgt ggaatggctg cgccagcagc | 1080 |
| ccccagccgg caaggcgcag caccgatttc gcgtagtcgg cccgtggctg ggcgaggttg | 1140 |
| tacgccataa ccaacgcgaa caccgggaac gcgatccgcc caattcgga taagaccggc | 1200 |
| acatagccgc cgaacaacac cttcgccacg tgatcgccgg tcatcaacac caacgcaatc | 1260 |
| cacttcaacg cctcgcggcc gctgctggtc atgtcacatc tccagcgtgg tggaaggcgt | 1320 |
| ggtggtcttg gtgctgtacg ccttcgactc aggaaagcta ccctgtgtgc gcgtagagcg | 1380 |
| ctgcacagcg atgccattga acccaggcgc agccgcccca ccctgcgccg cctgttgctg | 1440 |

```
ctgggcgggc tgctgctcgt tctggcgctg ctgacgatac gggttgtaga ccgggccgcg   1500
cttggcaatc gtgcggcact gcggctggtc gaggtcgtac gccgtgccct gctctgtcat   1560
acacgtgcag gacgcttctt tgtgcttacc ctgcgcatcg atgccagcga gcgacgacat   1620
gcagatcaac atcggatcgg cagtgatgct gcgatcatca acaccggtg ctgtccacgg    1680 catggtgccg aaccggggaa ggtgttgctt ggcatattcg gtgggagatt cccaacgcgg   1740
accatcacgc cgtgcggtgg tcgcagaccc gccaggggcc gcatcggctg acgccgattg   1800
cgtcccctta gctccgccgg ccatcgcgct gggcttgagc atcgtgtagg cgagccatcc   1860
aagcgcgatg gcaaggatga ccaaacccgg caacgccatc actttccacg gaatgcgcgg   1920
cttgatcgtg tgcacctcag ccgacttgta tgcgccgaag atcgaggaag cagcagacg    1980 cgtggtcgcg tgggcaagat cgcgtttagc agacgatttg atttcttcgt tcaactcgcc   2040
ccagcggaac acgtcgatca tcttggtgcc gaaacgacgc accacgtggg tgtgtgcgcc   2100
gatcaatcca cgcacgaacg ggtacagctg attcggctgc tgcgtcgtcc acacaaagtc   2160
aagtccgcga tgccgatgct cagcaaggtc aagcacgtgt ttgggcgtct gctggcgcgt   2220
ggcgtcgtgc aaatggccat accacttcca tgcttcgtct acgaagatca acgagccatt   2280
cggcacgaca tagttgtcat ctgcatcctt gtcgttccac ttgcggggat cgtccagcac   2340
ggtcgctaga ccgtcctgca atccatcgat tcctgcagcg aaaatcggcc gctcggcgcg   2400
cttggcctct tcgaccaggc gctccatcat gagcgcggtt ttaccattgc cgggttgccc   2460
ggtatatagc tcgattggca ttacggcttg gctccgaatc cacgcttaaa caggaacagc   2520
cgcccttgca tgatggcgtg cttggctgca accgcagaga taaccatggt cagtgccttg   2580
tcgaactgaa gcacgccaaa ccatgccatc gcgtctgcac cgagttggcc gttgccgctg   2640
cccatgcctt gggcgtagtc cttgagcaga tcgatggcag gctcaacgac cattttgatg   2700
gtgccgaaat tgatgccgag ccacaccagc gcggtcatga tccatagacc gatacgcgac   2760
ttgaacagcc atgccagcgc ggtgacgagt tgtgcgatta ccagggcat tatgcgctac    2820 ctccttgact catcagacgt agggaaacca gggatgccat gaccaacaca atttggccgc   2880
caagcaccat ccactggcaa aacttggacg tgtcgaagtg cagggtttgg ccgaacaccg   2940
caacatcggg aatcgttgga cacgtgcggc tgtagccgaa accgtgcgta tcgagttcac   3000
ccgttgggta accgtgttcg ccatatcccg actcatcgga aaacgcgtcc gcaggcttgc   3060
catcggcacc gatatcagcc gtgccattac cagtgatcgc atcgcgaatc gccttaacat   3120
ctgcattgtt cccgtaccg ccgccgctgt tgttcgccgc cttttccagc gcacacgcag    3180
cccgccattg catcaacaat tgcgagtatt caagggcctt gcagttctcg ccgacgcaca   3240
caggcatcga tgcacacgaa ccgcctgtga tgtttacgtc gcggcgtgtg ttgcaatcaa   3300
tgcgccattg aatccgcgcc tgtccgcaca tgatcgcgtc accgctacaa ctcggcggcg   3360
aatcgcagct atcaccgcca gaaaactggc tcttgtcgcc ctccccggc tcgtcaggct    3420 cgccatcgcc atcaccatct tttttacacg tgccatcggg accacgcact tcaccagcag   3480
cgcattgacc atcgcgggg agacatgagc cgctgggcga cctgatctga ccagcagggc   3540
aatcgttctt cttcggtgcg catgtgccgt cagcctgaag caacatgcct tcgggacact   3600
tattcgacga acacccgccc ttgccgtcag gcacctgccc ttccggacac tcttcggtcg   3660
gcggcggctc acatacgccc aggtaaccat tccaaccata accaccactc atggcatcac   3720
aagtcttctc tggatccttc ggacagattg cgcccgtggc gttccaagtc atcgtgtcat   3780
```

```
cgccattgcc gaaccaaaca ccgtcgcatc cattgcggca accgatgctg ccattgcgcg    3840
cagtacccac atacgtaccc catgggccag aaccagtgta atcaggctcc tgatcgcaac    3900
ccttagacca cgggaaataa ccgtagtaag cccgatacca atcacaacta ctacagtccc    3960
ttgtttcaaa ttggccgcga tacgcttgac tgccctgctc gacattgcac tcgggattcc    4020
tgtcgttagc accacggcca agggaggcta gataggcagc ggtttgcgac atacatgcgg    4080
aatacgcagc gccttgcgtt ccgaagtctt gcgcactggc acaaccaatg ccacaccatg    4140
cgagcgttgc cgctacaagc acgtaggcga ggcgacgcgc aatcgcggat gcaaacacgc    4200
gtgcgagcca acccattatt cgaaatccac gaagacaatc gcgcaggcca ccagccatgc    4260
gccgaaccaa atccaccctt ccatcgccgt tcccctgccc tatccccgta aaagaccggc    4320
gggagggagt tggccctgtc cgccggtggt cgttacatgg cgcggcgcac ccacttgtag    4380
accttgatgc ccaccaggac ggtcagcact gcaccgccaa tggaggcaat ggggcctgcg    4440
gcaccctgga tggcagacac aacatcgccc acatccacac caccaccgcc ggacgcgaac    4500
gccggagcgg agacgagagc ggccgaacca actgcggcca gagcagcggt cttgttcttg    4560
aacagggtct tgagcttgcg cattgcatgt cctcctagga ctgttgaatt ttcttgcgga    4620
tgagccggaa cacatacgcc gtgggcccaca ggaacgcgat tgcgctgcca atggcctggg    4680
catccttcac cgccagttcc ggcaagagtg acggttgagg aatccatatc actgccgtgc    4740
acgtccccgc tgccgtgtcc aaatcggctt ccaggcatgc gggaacgagc acggccatgg    4800
gttaggcgac ccgcgccgca ggctgtacag ctttggcagt ggcatcaggg atcaggcgga    4860
tacgacgacc gaattcgaga ccaccgaatt tgttgttctg caacgacttg ggatcgatga    4920
tgtaaaaacc ttcaccgtag ggcgcttgat cctcatcgag accgatgatg aaaggcaacg    4980
ggaaatctcc atcgcgcagc acagctgcgg tctgctcacg gaaatgcgtc gcgggcttac    5040
cctcacgcgc aggaaaggaa cgaacagcga cagcggaact catgacttgg actttcatag    5100
ttggactacc ttccaggcga atgtccggcc gaaaatgaat gtgactttcc acggagacgg    5160
ccagaactcc ccggtaagcc tgtcgaacca tccgcccttt gctttgcgga tatccgcttc    5220
cccgccgaga gcttcacgcg catctttcgg ggctttccac cagcgcaact cgcgcttaga    5280
ttcggtatcg agtccaccaa tcccgtgggt gcggaagcct ttgggaaaag ctccagctgt    5340
aagggcagtg aacttgctcg cgtatttcgc gagatagccg acgcagttgc gggctttctc    5400
aatttgcgtt gtgccatgtg gccaccagcc gcgttgatca accttgccga aatacatacc    5460
agtgggaacc caaagcatca cgtgatagtg cgggcggaat cgctgggtga gttctccgac    5520
ccatacgtaa cgaaagcttt cacggttcca ccgtgcgcgc ccagatttaa ggcgattgaa    5580
gtggccgcgc atgcgtttaa atagttcgct aacgtcacca gggctgctgt cgcttccatc    5640
acggtaggtg agcgtgagga ataccacgc accccggaag gaaccttttt tcgcttcctg     5700
atcatgcaga cgtgctccgg taatcacgga ctttcgcagc cgttgcgccc gcgctttcag    5760
cgggtcaatt tcgatggtca cggtgcctgt cgcagaggcg cgcgtgtcac ttgtttttgta    5820 atggacaagc ccaagggcca gcgctgcgcg ctggccctct gcggtcaatg cgaccggatg    5880
cgccgcgtcg aactcacgca cgcttgtacc gaccacacgc ttgttctttt ggatattctc    5940
tgcagcaatt tcagtgcggc gcgtagcggc ctgcatgacg ccgacagatg catcaaacgc    6000
agaaagctca cgcgattgcg tgggctgctc ctgcatgcgt atacgtgcgt ttttcgaggt    6060
gcatgcaaca cacaaaccgc ctggaaaaaa ataggcagtg gggtcgccgc agaaggagca    6120
tgtgccgtca gacatcgctc tcatcctcag agagcgaatc gaacaggaca tcaaagcagt    6180
```

-continued

```
cgtcgcacaa aacaccttcc tcagtgcaat gggcaaagac cgcacgatca aaacggccgc    6240
accgctcgca ctcgaaaaca agaaaatcaa ccacggcaca cctcgcgtta ggcgctacaa    6300
atcgtgacgc gtcgcgaaac agtcggcgcg accagggaaa cgtagctttc gatgatgaag    6360
acctgttcgc ggtgtgcgcg cagcgcagct tcggcgcgac ggtcaagaat ccaggcgacc    6420
aaccgggcga ggccgacgat cacggtcagc gcggaagcgc cgatcaatgc aagtgcgttg    6480
gtgtcagtcg acagtgccat taggcggcct ccgcgacggt gacaccacga acgcggaaat    6540
cgcggactac atcgccatac ttgaaaccat cggcgaccaa aaaggcaatg cgagcagcgg    6600
catcgtcacg cgctgcatta cgggtcggat gcgaagcgag gaccacccag cggcgaccgt    6660
cgcggtactg aacctgaaat cccatggtga agccccctatc ccctaccctg accgtgacc    6720 cccgggggt accgggggc ggggcgctta gccgcgctaa acgctgatgc ttgtatagtt    6780
caacgaaaca agaatgtaaa ggtcagctaa acatgagcgc cgaaaacgaa ctgatcgacc    6840
tggtgcgagc aggaggaaaa ttcagttcag acaatgcctt agctcagaag ctgggcgtca    6900
ccagggcaat ggtgagctcg tggcggtcgg gcagatatgc gatgccggac gaccaaattg    6960
cgcagctttg tgcgctagcg aagctggacg gagccagttg gatggcaagg attcacactg    7020
aacgtgctgg atcggcaaca gagcgcgccc tgtggaagtc aatcctggac cggctggccc    7080
cgatcaccgc agtggtcggg gcgctggcaa tcgtggcagt cgggctgcac gcaggtgctc    7140 atgagggct gctgacggcc ctttccccgc tcgccataac gccaaccgtc tatacattat    7200
gcgaa                                                                 7205
```

<210> SEQ ID NO 27
<211> LENGTH: 359
<212> TYPE: PRT
<213> ORGANISM: Bacteriophage XacF1

<400> SEQUENCE: 27

```
Met Leu Leu Met His Val Thr Leu Pro Trp Ser Ser Ile Val Ala Asp
1               5                   10                  15

Gly Thr Cys Ser Phe Cys Gly Asp Thr Thr Ala Tyr Phe Phe Pro Gly
                20                  25                  30

Gly Leu Cys Val Ala Cys Thr Ser Lys Asn Ala Arg Ile Arg Met His
            35                  40                  45

Glu Gln Pro Thr Gln Ser Arg Glu Leu Ser Ala Phe Asp Ala Ser Val
        50                  55                  60

Gly Val Met Gln Ala Ala Thr Arg Arg Thr Glu Ile Ala Ala Glu Lys
65                  70                  75                  80

Ile Gln Lys Asn Lys Arg Val Val Gly Thr Ser Val Arg Glu Phe Asp
                85                  90                  95

Ala Ala His Pro Ile Ala Leu Thr Ala Glu Gly Gln Arg Ala Ala Leu
            100                 105                 110

Ala Leu Gly Leu Val His Tyr Lys Thr Ser Asp Thr Arg Ala Ser Thr
        115                 120                 125

Thr Gly Thr Val Thr Ile Glu Ile Asp Pro Leu Gln Ala Arg Ala Gln
    130                 135                 140

Arg Leu Arg Lys Ser Val Ile Thr Gly Ala Leu His Asp Gln Glu
145                 150                 155                 160

Ala Lys Lys Gly Ser Phe Arg Gly Ala Trp Tyr Phe Leu Thr Leu Thr
                165                 170                 175

Tyr Arg Asp Gly Ser Asp Ser Ser Pro Arg Asp Val Ser Glu Leu Phe
```

```
            180                 185                 190
Lys Arg Met Arg Gly His Phe Asn Arg Leu Lys Ser Gly Arg Ala Arg
                195                 200                 205

Trp Asn Arg Glu Ser Phe Arg Tyr Val Trp Val Gly Glu Leu Thr Gln
            210                 215                 220

Arg Phe Arg Pro His Tyr His Val Met Leu Trp Val Pro Thr Gly Met
225                 230                 235                 240

Tyr Phe Gly Lys Val Asp Gln Arg Gly Trp Trp Pro His Gly Thr Thr
                245                 250                 255

Gln Ile Glu Lys Ala Arg Asn Cys Val Gly Tyr Leu Ala Lys Tyr Ala
            260                 265                 270

Ser Lys Phe Thr Ala Leu Thr Ala Gly Ala Phe Pro Lys Gly Phe Arg
                275                 280                 285

Thr His Gly Ile Gly Gly Leu Asp Thr Glu Ser Lys Arg Glu Leu Arg
            290                 295                 300

Trp Trp Lys Ala Pro Lys Asp Ala Arg Glu Ala Leu Gly Gly Glu Ala
305                 310                 315                 320

Asp Ile Arg Lys Ala Lys Gly Gly Trp Phe Asp Arg Leu Thr Gly Glu
                325                 330                 335

Phe Trp Pro Ser Pro Trp Lys Val Thr Phe Ile Phe Gly Arg Thr Phe
            340                 345                 350

Ala Trp Lys Val Val Pro Leu
            355

<210> SEQ ID NO 28
<211> LENGTH: 98
<212> TYPE: PRT
<213> ORGANISM: Bacteriophage XacF1

<400> SEQUENCE: 28

Met Lys Val Gln Ile Met Ser Ser Ala Val Ala Ile Arg Ser Phe Pro
1               5                   10                  15

Ala Arg Asp Gly Lys Pro Ala Thr His Phe Arg Glu Gln Thr Ala Ala
                20                  25                  30

Val Leu Arg Glu Gly Asp Phe Pro Leu Pro Phe Thr Ile Ser Leu Asp
            35                  40                  45

Glu Asp Gln Ala Pro Tyr Gly Glu Gly Phe Tyr Val Ile Asp Pro Lys
50                  55                  60

Ser Met Gln Asn Asn Lys Tyr Gly Gly Leu Glu Phe Gly Arg Arg Ile
65                  70                  75                  80

Arg Leu Ile Pro Asp Ala Thr Ala Lys Ala Ala Gln Pro Ala Ala Arg
                85                  90                  95

Val Ser

<210> SEQ ID NO 29
<211> LENGTH: 66
<212> TYPE: PRT
<213> ORGANISM: Bacteriophage XacF1

<400> SEQUENCE: 29

Met Ala Lys Val Leu Thr Cys Thr Gln Tyr Asn Asp Ser Thr Gln Gln
1               5                   10                  15

Cys Glu Val Gln Ala Trp Ile Asp Gln Ser Asp Trp Thr Thr Pro Leu
                20                  25                  30

Pro Thr Ile Glu Gln Ala Ala Met Val Gly Gly Ala Tyr Phe Ile Gly
            35                  40                  45
```

```
Leu Met Thr Leu Ala Val Ile Lys Gly Leu Leu Asn Pro Lys Ser Ile
    50                  55                  60

Glu Glu
65
```

<210> SEQ ID NO 30
<211> LENGTH: 85
<212> TYPE: PRT
<213> ORGANISM: Bacteriophage XacF1

<400> SEQUENCE: 30

```
Met Glu Lys Asn Ile Ser Thr Val Val Thr Lys Ala Lys Ser Ala Val
1               5                   10                  15

Ser Asn Ala Lys Thr Ala Ala Ile Leu Gly Ser Thr Ala Leu Met Ala
            20                  25                  30

Met Pro Gly Phe Ala Phe Ala Ser Gly Gly Gly Asp Phe Asp Gly
        35                  40                  45

Thr Ala Ile Ile Gly Lys Val Thr Thr Tyr Thr Ala Ile Gly Val Thr
    50                  55                  60

Ile Leu Ala Ala Phe Ala Leu Gly Arg Trp Thr Leu Arg Ala Leu Gly
65                  70                  75                  80

Leu Ile Gly Gly Lys
            85
```

<210> SEQ ID NO 31
<211> LENGTH: 22
<212> TYPE: PRT
<213> ORGANISM: Bacteriophage XacF1

<400> SEQUENCE: 31

```
Met Glu Gly Leu Ile Val Leu Val Phe Leu Ile His Ala Ala His Val
1               5                   10                  15

Cys Ala Thr Gly Trp Asn
            20
```

<210> SEQ ID NO 32
<211> LENGTH: 492
<212> TYPE: PRT
<213> ORGANISM: Bacteriophage XacF1

<400> SEQUENCE: 32

```
Met Arg Gly Leu Gly Gly Tyr Phe Ala Arg Ala Val Val Arg Arg Ile
1               5                   10                  15

Ala Tyr Val Val Val Ala Ala Cys Phe Gly Leu Leu Leu Gln Leu Cys
            20                  25                  30

Ser Gly Ser Ala His Ala Ala Val Asp Gln Gly Glu Ala Tyr Ser Leu
        35                  40                  45

Cys Met Lys Phe Ala Ser Asp Met Val Ala Lys Asn Pro Asp Met Arg
    50                  55                  60

Arg Asn Pro Ser Cys Pro Ser Arg Arg Ala Phe Gln Tyr Thr Cys Gln
65                  70                  75                  80

Tyr Glu Ala Ile Pro Tyr Val Gly Ala Ser Gln Trp Ser Val Asp Thr
                85                  90                  95

Cys Gly Asp Tyr Ser Tyr Asp Asp Gln Tyr Thr Cys Ala Ser Arg Asn
            100                 105                 110

Ser Asn Lys Leu Ala Asp Ala Ala Pro Trp Tyr Thr Pro Pro Asn
        115                 120                 125
```

```
Cys Ile Ser Gly Cys Gln Val Gln Gly Thr Ser Phe Ser Gly Asp Asn
        130                 135                 140

Gly Gly Val Lys Thr Tyr Gly Met Lys Asp Arg Thr Tyr Asn Gly Ser
145                 150                 155                 160

Ile Cys Thr Pro Thr Lys Pro Thr Asn Asp Ile Gly Glu Leu Gln Glu
                165                 170                 175

Glu Lys Asn Asp Ala Thr Lys Glu Lys Ala Pro Glu Cys Thr Ala Leu
            180                 185                 190

Gly Ser Gly Gln Thr Ala Cys Leu Lys Pro Asn Gly Asp Tyr Cys Ala
        195                 200                 205

Thr Ala Ser Ser Gly Lys Thr Phe Cys Trp Lys Pro Ala Glu Thr Gly
210                 215                 220

Lys Lys Thr Asp Ala Thr Asp Ala Gln Ser Lys Thr Pro Lys Gly Asp
225                 230                 235                 240

Pro Val Thr Pro Pro Pro Ile Pro Pro Asp Gly Glu Trp Gln Arg
                245                 250                 255

Lys Glu Gly His Gln Gln Thr Thr Cys Val Asn Asn Thr Cys Thr Thr
            260                 265                 270

Tyr Asn Val Thr Asn Tyr Thr Thr Val Pro Ser Gly Thr Ser Lys Asn
        275                 280                 285

Gly Thr Gly Asp Asn Ser Ala Asp Gly Ser Gly Asn Thr Ser Gly Asn
290                 295                 300

Gly Ser Asn Ser Gly Thr Gly Lys Lys Asp Asp Ser Lys Asp Ser
305                 310                 315                 320

Ala Thr Asp Ser Gly Asn Cys Asp Ala Pro Pro Ile Cys Val Gly Asp
                325                 330                 335

Thr Leu Lys Cys Leu Gln Leu Lys Phe Thr Trp Lys Ile Asp Cys Asn
            340                 345                 350

Thr Arg Gly Asn Glu Ile Thr Gln Gly Asp Ser Cys Ala Asp Gly Asp
        355                 360                 365

Val Pro Val Cys Ala Gly Lys Ser Cys Lys Ala Glu Ala Tyr Ala Gln
370                 375                 380

Val Val Gln Gln Trp Lys Gln Arg Cys Ala Val Glu Ala Met Gly Gln
385                 390                 395                 400

Gly Met Ala Ser Arg Ala Ala Ile Ser Asn Gly Asp Asp Ala Gly
                405                 410                 415

Val Val Glu Gly Ile Trp Gly Gly Glu Ser Ala Gly Ala Gly Leu Lys
            420                 425                 430

Leu Arg Gln Asp Leu Val Asn Val Gly Asn Gly Thr Gly Gly Leu
        435                 440                 445

Leu Pro Asp Val Asp Ile Glu Gly Gln His Trp Thr Val Pro Ser Gly
450                 455                 460

Phe Phe Asp Ala Ile Ala Ala Val Lys Met Val Ile Ala Met Cys
465                 470                 475                 480

Thr Val Ile Ala Met Phe Val Val Gly Arg Asn Ile
                485                 490

<210> SEQ ID NO 33
<211> LENGTH: 102
<212> TYPE: PRT
<213> ORGANISM: Bacteriophage XacF1

<400> SEQUENCE: 33

Met Phe Asp Trp Ala Arg Asp Phe Ala Asn Asn Phe Phe Glu Asn Ala
1               5                   10                  15
```

```
Ala Asp Ala Val His Lys Leu Val Lys Leu Lys Ala Ala Ile Trp Leu
         20                  25                  30

Gly Arg Leu Leu Ser Ala Leu Gly Leu Gly Phe Ala Ala Gln His Phe
     35                  40                  45

Ile Tyr Asn Pro Ile Ile Glu Tyr Ala Gln Asn Ala Trp Ser Ser Val
 50                  55                  60

Pro Ala Gly Ile Ala Ala Trp Val His Ala Leu Gly Ile Asp Ala Gly
 65                  70                  75                  80

Val Ser Ile Ile Leu Ser Ala Tyr Gly Ile Arg Gly Ala Glu Arg Ile
             85                  90                  95

Phe Ile Gln Arg Arg Asn
            100

<210> SEQ ID NO 34
<211> LENGTH: 388
<212> TYPE: PRT
<213> ORGANISM: Bacteriophage XacF1

<400> SEQUENCE: 34

Met Ile Gly Asp Thr Ala Ser Ile Ser Leu Leu Thr Gly Leu Pro Gly
 1               5                  10                  15

Ser Gly Lys Ser Leu Arg Ile Ile Gln Ala Ile Arg Tyr Leu Met Asp
             20                  25                  30

Lys Gly Ala His Val Tyr Val Cys Asn Ile Asp Gly Ile Ser Val Pro
         35                  40                  45

Gly Thr Thr Pro Trp Ala Asp Pro His Lys Trp Gln Asp Leu Pro Ala
 50                  55                  60

Gly Ser Ile Leu Phe Val Asp Glu Ala Gln His Phe Phe Pro Ala Arg
 65                  70                  75                  80

Arg Gly Gly Asp Pro Val Glu Thr Ile Lys Ala Met Ser Thr Ile Arg
             85                  90                  95

His Asp Gly Val Arg Leu Val Leu Ala Thr Gln Gln Pro Asn Tyr Leu
            100                 105                 110

Asp Thr Tyr Leu Arg Gly Leu Val Gly Tyr His Glu His Leu Leu Arg
        115                 120                 125

Gln Ser Gly Lys Gln Lys Thr Phe Ile Phe Arg Asn Ser Gln Ile Ile
    130                 135                 140

Glu Glu Val Arg Ser Pro Leu Pro Arg Ile Lys Lys Leu Tyr Asp Tyr
145                 150                 155                 160

Glu Val Trp Lys Gln Pro Thr Glu Cys Phe Lys Phe Tyr Lys Ser Ala
                165                 170                 175

Glu Val His Thr Met Lys Tyr Gln Met Pro Ala Leu Val Lys Lys Ala
            180                 185                 190

Leu Met Ile Leu Pro Val Val Ala Leu Leu Ala Gly Gly Ala Trp Tyr
        195                 200                 205

Ala Val Tyr Arg Asp Thr Met Phe Ala Lys Lys Ala Asp Ala Ala Pro
    210                 215                 220

Ala Asn Lys Thr Ala Pro Ser Gly Pro Ser Leu Ala Gly Thr Ala Ser
225                 230                 235                 240

Ala Gly Ala Ala Ala Arg Pro Lys Val Asn Ser Ala Glu Asp Tyr Val
                245                 250                 255

Gly Gln Leu Val Pro Leu Val Ala Asp Val Pro Trp Ser Ala Pro Ala
            260                 265                 270

Tyr Val Asp Arg Pro Val Val Ser Asp Pro His Val Tyr Cys Met Ala
```

```
                        275                 280                 285
Thr Glu Asn Thr Cys Arg Cys Val Thr Glu Gln Asn Ser Arg Val Val
290                 295                 300

Met Arg Asp Asp Val Cys Arg Asp Ile Ala Arg Trp Gly Glu Pro Tyr
305                 310                 315                 320

Asn Pro Tyr Lys Pro Pro His Ser Pro Ala Gln Lys Gln Gln Asp Ser
                325                 330                 335

Pro Val Ala Glu Ala Thr Gln Pro Lys Pro Gln Val Pro Gln Gln Ser
                340                 345                 350

Gly Ala Val Ser Ser Val Gln Arg Ala Thr Arg Ser Leu Gly Thr
                355                 360                 365

Phe Pro Glu Ser Pro Pro Tyr Gln Thr Thr Thr Tyr Thr Pro Pro Thr
370                 375                 380

Thr Arg Asp Leu
385

<210> SEQ ID NO 35
<211> LENGTH: 215
<212> TYPE: PRT
<213> ORGANISM: Bacteriophage XacF1

<400> SEQUENCE: 35

Met Ser Ser Ser Ala Arg Glu Leu Leu Lys Trp Ile Ala Leu Val Cys
1               5                   10                  15

Met Thr Phe Asp His Val Ala Lys Val Phe Tyr Asp Gly Tyr Val Pro
                20                  25                  30

Val Leu Ser Glu Leu Gly Arg Ile Ala Phe Pro Leu Phe Ala Leu Val
                35                  40                  45

Met Ala Tyr Asn Leu Ala Gln Pro Gly Ala Asp Val Gly Lys Ser Val
50                  55                  60

Arg Arg Leu Val Cys Trp Gly Leu Leu Ala Gln Pro Phe His Ala Trp
65                  70                  75                  80

Ala Phe Gly Tyr Trp Val Pro Val Asn Val Leu Leu Ala Phe Ala Leu
                85                  90                  95

Ala Ala Ala Ala Val Trp Ala Ile Gln Arg Gly Arg Trp Val Leu Leu
                100                 105                 110

Met Leu Cys Ala Ala Pro Ala Pro Leu Phe Val Asp Tyr Gln Trp Thr
                115                 120                 125

Gly Ile Ala Leu Val Val Ala Gly Trp Ala Tyr Tyr Ala Lys Val Met
130                 135                 140

Arg Ser Pro Ile Pro Val Val Met Ala Leu Gly Ala Leu Cys Trp Phe
145                 150                 155                 160

Asn Gly Ser Leu Trp Ala Leu Leu Ala Ile Pro Ile Ala Leu Ser
                165                 170                 175

Glu Ala Val Thr Asn Arg Gly Met Ala Ile Pro Arg Thr Arg Leu Gly
                180                 185                 190

Phe Tyr Gly Tyr Tyr Val Gly His Leu Ala Ile Leu Gly Leu Leu Ala
                195                 200                 205

Leu Lys Pro Ala Leu Ile Ser
    210                 215

<210> SEQ ID NO 36
<211> LENGTH: 130
<212> TYPE: PRT
<213> ORGANISM: Bacteriophage XacF1
```

<400> SEQUENCE: 36

Met Glu Ala Arg Phe Ala Met Leu Leu Ala Leu Ala Ile Val Val Pro
1               5                   10                  15

Cys His Ala Gln Gln Val His Lys Cys Arg Glu Arg Gly Gln Val Val
            20                  25                  30

Tyr Gln Ser Ala Pro Cys Ala Ser Gly Gln Ala Gln Lys Val Trp Asp
        35                  40                  45

Ala Ala Pro Ala Pro Glu Gln Ser Asn Ala Glu Gln Trp Arg Leu Tyr
50                  55                  60

Arg Ile Arg Lys Gln Leu Asp Ser Arg Tyr Ala Ala Asp Arg Ser Ala
65                  70                  75                  80

Ser Ala Ala Ala Tyr Val Ser Gly Pro Gln Ser Ser Asn Ala Cys Glu
                85                  90                  95

Ser Ala Lys Ala Gln Arg Lys Gln Val Tyr Asp Ala Ala Gly Leu His
            100                 105                 110

Arg Ser Tyr Glu Ile Ser Ser Tyr Trp Asp Asn Val Val Gln Asn Ala
        115                 120                 125

Cys Lys
    130

<210> SEQ ID NO 37
<211> LENGTH: 127
<212> TYPE: PRT
<213> ORGANISM: Bacteriophage XacF1

<400> SEQUENCE: 37

Met Thr Leu Asp Thr Tyr Asp Arg Val Asp Leu Thr Gly Pro Trp Ala
1               5                   10                  15

Gly Phe Gly Phe Gln Gly His Arg Phe Phe Thr Pro Glu Asn Tyr Asp
            20                  25                  30

Ile Glu Pro Cys Asp Met Arg Tyr Trp Ala Leu Thr Cys Ala Ile Ala
        35                  40                  45

Arg Glu Trp Ser Leu Leu Met Ser Glu Glu Arg Asn Ala Arg Ser Ala
50                  55                  60

Asn Pro Arg Lys Pro Thr Ala Thr Arg Ser Pro Gly Ser Arg Leu Ser
65                  70                  75                  80

Arg Gly Ala Asp Val Ile Tyr Leu Arg Asp Val Leu Leu Gln Arg Arg
                85                  90                  95

Glu Lys Arg Leu Ser Val Val Asp Gly Ala Gly Ser Ala Asp Arg Ala
            100                 105                 110

Gln Val Val Arg Arg Thr Arg Gly Pro Arg Ala Pro Arg Arg Gly
        115                 120                 125

<210> SEQ ID NO 38
<211> LENGTH: 152
<212> TYPE: PRT
<213> ORGANISM: Bacteriophage XacF1

<400> SEQUENCE: 38

Met Asp His Val Asn Asn Leu Leu Asp Thr Val Arg Lys Ser Cys Ala
1               5                   10                  15

Ile Pro Ser Asp Asn Met Leu Ser Lys Lys Ile Gly Val Thr Arg Ala
            20                  25                  30

Leu Ile Ser Gly Trp Arg Val Gly Arg Tyr Pro Val Pro Asp Ala Arg
        35                  40                  45

Ile Ala Glu Leu Cys Ala Met Ala His Leu Asp Gly Gly Glu Trp Met

Ala Lys Ile His Ala Glu Ala Ala Ser Pro Ala Glu Lys Ala Leu
 65                  70                  75                  80

Trp Arg Ser Val Leu Asp Arg Leu Ser Ala Ala Ala Val Val Ala
                 85                  90                  95

Leu Leu Val Leu Ala Val His Thr Gly Ala His Glu Ala Leu Leu Ala
            100                 105                 110

Ala Leu Ser Pro Val Ala Val Thr His Pro Leu Tyr Ile Met Arg Ser
            115                 120                 125

Val Leu Leu Thr Leu Leu Cys Ala Leu Ala Ala Tyr His Cys Trp Ser
130                 135                 140

Leu His Arg Lys Arg Thr Gly Gln
145                 150

<210> SEQ ID NO 39
<211> LENGTH: 62
<212> TYPE: PRT
<213> ORGANISM: Bacteriophage XacF1

<400> SEQUENCE: 39

Met His Pro Tyr Ser Ile Leu Gly Gln Leu Ala Leu His Ile Leu
1               5                   10                  15

Val Ser Ile Cys Val Leu Thr Gly Tyr Ala Ile Val Ala Val Ile Cys
                20                  25                  30

Trp Cys Leu Asp Arg Lys His Asp Ala Met Val Ala Gln Ile Glu Gln
                35                  40                  45

Ala Ala Leu Val Ala Ile Ala Tyr Arg Glu Val Arg Arg Gly
            50                  55                  60

<210> SEQ ID NO 40
<211> LENGTH: 108
<212> TYPE: PRT
<213> ORGANISM: Bacteriophage Cf2

<400> SEQUENCE: 40

Met Arg Asn Arg Thr Leu Thr Gly Gln Trp Ala Gly Phe Ser Phe Gln
1               5                   10                  15

Asn Gly Tyr Leu Ile Thr Pro Glu Gly Arg Ala Met Glu Pro Trp Gln
                20                  25                  30

Leu Ser Tyr Leu Ser Leu Thr Cys Asp Ile Ala Arg Glu Trp Thr Lys
            35                  40                  45

Met Met Ala Glu Gly Arg Ser Lys Thr Arg Pro Lys Arg Pro Ala Asn
 50                 55                  60

Val Ile Phe Ile Arg Asp Arg Phe Arg Lys Lys Ile Glu Thr Lys Pro
 65                 70                  75                  80

Gly Pro Gln Val Val Ala Thr Gly Phe Ala Ala Glu Cys Ala Gly Ser
                85                  90                  95

Ser Leu Pro Lys Ala Arg Lys Arg Lys Gly Arg Val
            100                 105

<210> SEQ ID NO 41
<211> LENGTH: 103
<212> TYPE: PRT
<213> ORGANISM: Bacteriophage Cf2

<400> SEQUENCE: 41

Met Ser Tyr Arg Pro Gln Asn Asn His Asp Gly Leu Trp Trp Glu Ile
1               5                   10                  15

```
Ala Leu Gly Ile Phe Val Gly Gln Leu Met Thr Ala Ala Leu Ala Gly
            20                  25                  30

Val Val Ala Leu Cys Leu Gly Tyr Phe Thr Met Arg Ser Val Ser Ala
        35                  40                  45

Ala Leu Pro Ala Gly Ala Pro Gln Arg Leu Tyr Thr Pro Arg Ser Gln
    50                  55                  60

Arg Val Val Pro Glu Pro Leu Gln Leu Arg Glu Leu Glu Ser Asn Glu
65                  70                  75                  80

Arg Cys Ile Gln His Lys Arg Phe Arg Leu Ser Asn Gly Trp Gln
                85                  90                  95

Glu Leu Pro Asn Asp Pro Cys
                100

<210> SEQ ID NO 42
<211> LENGTH: 444
<212> TYPE: PRT
<213> ORGANISM: Bacteriophage Cf2

<400> SEQUENCE: 42

Met Leu Val Phe Asn Glu Gly Val Pro Arg Ala Gly Lys Ser Tyr Asp
1               5                   10                  15

Ala Val Lys Asn His Ile Leu Pro Ala Ile Lys Lys Gly Arg Arg Val
            20                  25                  30

Phe Ala Arg Leu Asn Gly Leu Arg His Asp Arg Ile Ala Lys His Leu
        35                  40                  45

Gly Met Glu Glu Lys Asp Val Gln His Cys Leu Val Leu Val Asp Thr
    50                  55                  60

Lys Asp Val Ala Lys Leu Phe Ala Cys Thr Gln Asp Ala Ser Gly Lys
65                  70                  75                  80

Trp Cys Ile Pro Asp Glu Phe Lys Asp Ala Leu Val Val Ile Asp Glu
                85                  90                  95

Val His Glu Phe Tyr Val Asn Glu Arg Lys Pro Leu Glu Pro Ala Val
                100                 105                 110

Glu Asn Phe Trp Ala Leu Leu Gly Gln Asn Gly Gly Asp Ala Val Ile
            115                 120                 125

Met Thr Gln Trp Ile Asn Arg Leu His Ser Ala Val Lys Ala Arg Ile
    130                 135                 140

Glu Lys Lys Asn Thr Phe Gln Lys Leu Thr Ala Val Gly Met Lys Ser
145                 150                 155                 160

Arg Tyr Arg Val Thr Tyr Phe His Thr Thr Ser Pro Gly Lys Phe Glu
                165                 170                 175

Lys Val Gly Gly Gln Thr Leu Lys Tyr Asp Pro Val Ile Phe Pro Leu
            180                 185                 190

Tyr Asp Gly Tyr Ala Pro Gly Ala Glu Asn Thr Glu Val Tyr Glu Glu
        195                 200                 205

Gly Gly Lys Asn Val Trp Ala Met Ala Val Arg Ala Val Ile Phe
    210                 215                 220

Leu Val Val Gly Gly Val Gly Leu Tyr Phe Phe Ala Gly Phe Phe Ser
225                 230                 235                 240

Lys Gly Lys Gln Glu Thr His Lys Pro Ala Ala Gly Ala Thr Val
                245                 250                 255

Trp Gln Gln Ser Asp Lys Ala Ser Val Gly Ala Gly Leu Ala Asn Gly
            260                 265                 270

Ala Pro Ser Gly Ala Val Gln Ala Pro Pro Pro Asp Pro Leu Ala Asp
```

```
                275                 280                 285
Leu Thr Asp Glu Gln Arg Tyr Val Ala Gln Leu Ala Glu Lys Gly Arg
    290                 295                 300

Ile Arg Leu Ala Ala Arg Ala Arg Val Gly Ser Asp Glu Arg Ala Trp
305                 310                 315                 320

Val His Trp Ile Asp Thr Ser Asn Asn Val Ile Glu Gln Leu Asp Ile
                325                 330                 335

Asp Gln Leu Arg Ala Leu Gly Tyr Ser Val Thr Met Val Pro Tyr Gly
            340                 345                 350

Met Arg Leu Val Ala Gly Lys His Val Leu Val Ala Thr Pro Trp Pro
        355                 360                 365

Trp Arg Glu Pro Val Arg Glu Gln Asp Pro Arg Leu Tyr Asn Thr Ala
    370                 375                 380

Ser Asp Gly Lys Ser Asp Gly Ala Ala Gly Val Ala Thr Ala Gly Ser
385                 390                 395                 400

Asp Ala Gly Gly Ala Asp Arg Asp His Gln Arg Ser Ala Val Ile Gly
                405                 410                 415

His Val Pro Arg Ser Leu Gly Thr Phe Pro Glu Ser Lys Pro Tyr Gln
            420                 425                 430

Thr Thr Thr Ser Thr Pro Ala Thr Leu Asp Met
        435                 440
```

<210> SEQ ID NO 43
<211> LENGTH: 106
<212> TYPE: PRT
<213> ORGANISM: Bacteriophage Cf2

<400> SEQUENCE: 43

```
Met Tyr Ala Gly Trp Phe Thr Asp Leu Thr Trp Ile Trp Arg Ala
1               5                  10                  15

Val Lys Ala Val Trp Gln Ala Phe Ala Asp Phe Ile Gly Asp Leu Phe
            20                  25                  30

Val Met Trp Leu Glu Gln Ser Leu Ser Ala Ile Leu Tyr Val Leu Ser
        35                  40                  45

Leu Leu Pro Met Pro Asp Phe Met Lys Gly Gln Ser Ile Gly Ala Met
    50                  55                  60

Leu Gly Asn Ala Gly Ser Thr Ile Leu Trp Phe Ala Asp Val Phe Met
65                  70                  75                  80

Ile Gly Pro Ser Leu Val Ala Val Gly Ala Ala Met Ile Phe Tyr Leu
                85                  90                  95

Leu Arg Arg Val Leu Thr Leu Gly Ile Trp
            100                 105
```

<210> SEQ ID NO 44
<211> LENGTH: 397
<212> TYPE: PRT
<213> ORGANISM: Bacteriophage Cf2

<400> SEQUENCE: 44

```
Met Arg Val Ile Leu Ser Ala Leu Cys Thr Leu Val Ile Ala Leu Cys
1               5                  10                  15

Ala Ile Ser Pro Ala His Ala Ala Asp Ser Arg Ser Gln Ala Phe Ala
            20                  25                  30

Lys Cys Met Asn Asp Ala Ser Ala Tyr Gln Val Lys Asp Thr Asn Leu
        35                  40                  45

Ile Thr Ser Pro Gly Thr Cys Val Asp Lys Val Thr Glu Ala Thr Gly
```

```
            50                  55                  60
Lys Tyr Tyr Gln Cys Gln Tyr Ser Ala Ala Tyr Tyr Gln Gly Pro
 65                  70                  75                  80

Val Ser Val Val Thr Cys Gly Asp Tyr Pro Tyr Asp Asn Glu Asn
                     85                  90                  95

Cys Lys Asn Ala Pro Pro Leu Thr Asn Val Ser Val Arg Gly Ser Ile
                100                 105                 110

Tyr Ala Cys Ser Asn Gln Cys Gln Tyr Thr Met Asn Ser Ala Gly Gly
                115                 120                 125

Val Asp Val Cys Met Gly Gly Ala Asp Leu Tyr Cys Ala Ala Lys
    130                 135                 140

Asn Trp Ser Pro Thr Gly Gln Glu Cys Gln Gln Gly Asp Ala Val Pro
145                 150                 155                 160

Ser Gly Ile His Glu Pro Asp Lys Gln Thr Cys Ser Ser Thr Gly Gly
                165                 170                 175

Ala Tyr Ala Glu Cys Ile Arg Ser Asp Gly Thr His Cys Val Thr Gly
                180                 185                 190

Ala Ala Gly Ser Thr Leu Cys Trp Lys Pro Glu Leu Thr Gly Pro Arg
                195                 200                 205

Gln Thr Ala Asp Gly Thr Tyr Ala Gly Asp Arg Gln Lys Ala Pro Ala
210                 215                 220

Thr Pro Thr Pro Pro Asn Leu Lys Asp Pro Lys Glu Val Ser Asn
225                 230                 235                 240

Thr Thr Thr Thr Val Asn Asn Thr Thr Tyr Asn Thr Thr Thr Trp Ser
                245                 250                 255

Ser Ser Gly Ser Lys Gly Gly Gln Gly Asn Val Gly Glu Gly Gly Lys
                260                 265                 270

Asp Asn Gly Ser Gly Gly Ser Gly Gly Ser Gly Ser Gly Asp Gly
                275                 280                 285

Asp Gly Asp Gly Asp Gly Asp Ser Asp Pro Gly Glu Gly Ser Pro
                290                 295                 300

Ile Gly Asp Leu Tyr Thr Lys Ser Asp Lys Thr Val Glu Ser Val Val
305                 310                 315                 320

Ser Arg Phe Ala Thr Gln Val Arg Ala Thr Pro Leu Ala Gly Gly Ile
                325                 330                 335

Ala Ser Phe Met Thr Val Pro Ser Gly Gly Ser Cys Pro Val Phe Ser
                340                 345                 350

Leu Gly Ala Ser Lys Trp Trp Asp Ala Met Met Ile Asp Phe His Cys
                355                 360                 365

Ser Gly Thr Phe Leu Thr Phe Leu Arg Ala Cys Gly Trp Val Ile Leu
                370                 375                 380

Ala Ile Ala Ala Tyr Ala Ala Ile Arg Ile Ala Val Thr
385                 390                 395

<210> SEQ ID NO 45
<211> LENGTH: 42
<212> TYPE: PRT
<213> ORGANISM: Bacteriophage Cf2

<400> SEQUENCE: 45

Met Gly Asp Ile Leu Ser Gly Leu Ser Ala Ala Asp Ala Val Thr Ala
 1               5                  10                  15

Val Val Gly Ala Ala Ala Leu Ile Ala Leu Val Gly Phe Thr Lys Trp
                20                  25                  30
```

```
Gly Ala Lys Lys Val Ala Gly Phe Phe Gly
            35                  40
```

<210> SEQ ID NO 46
<211> LENGTH: 83
<212> TYPE: PRT
<213> ORGANISM: Bacteriophage Cf2

<400> SEQUENCE: 46

```
Met Ala Val Cys Val Ala Leu Gln Ala Asp Gly Thr Leu Val Pro Thr
1               5                   10                  15

Gly Gln Ser Val Gly Glu Cys Ser Gly Tyr Val Leu Val Ser Gly Ser
            20                  25                  30

Glu Tyr Ser Val Tyr Ala Leu Val Gln Glu Ala Phe Ala Met Pro Ser
        35                  40                  45

Lys Glu Asp Ala Val Ala Trp Ser Thr Gly Cys Cys Gly Val Val Ile
    50                  55                  60

Val Trp Phe Val Leu Gly Arg Leu Ala Gly Ser Val Ala Gly Met Phe
65                  70                  75                  80

Asn Asp Arg
```

<210> SEQ ID NO 47
<211> LENGTH: 92
<212> TYPE: PRT
<213> ORGANISM: Bacteriophage Cf2

<400> SEQUENCE: 47

```
Met Pro Ile Cys Arg Ile Leu Ser Ala Ala Val Glu Glu Val Asn
1               5                   10                  15

Gln Lys Thr Gly Glu Val Met Arg Gly Gln Thr Val Gly Leu Asp Leu
            20                  25                  30

Gly Asn Gly His Ala Leu Pro Phe Arg Val Gly Leu Gly Lys Arg Pro
        35                  40                  45

Ala Tyr Gln Pro Gly Glu Tyr Asp Ile Asp Pro Lys Ala Phe Ser Ile
    50                  55                  60

Gly Asn Tyr Gly Glu Leu Thr Leu Lys Arg Tyr Val Asp Leu Val Pro
65                  70                  75                  80

Leu Thr Pro Lys Ala Ala His Gln Pro Ala Lys Gly
            85                  90
```

<210> SEQ ID NO 48
<211> LENGTH: 295
<212> TYPE: PRT
<213> ORGANISM: Bacteriophage Cf2

<400> SEQUENCE: 48

```
Met Pro Glu Thr Ala Leu Glu Asp Phe Arg Cys Thr Asn Ile Asp Leu
1               5                   10                  15

Leu Leu Phe Arg Ile Phe Gly Phe Arg Gly Glu Val Val Ala Thr Ala
            20                  25                  30

Leu Arg Asn Lys Asn Trp Met Phe Tyr Ser His Ser Ala Leu Leu Met
        35                  40                  45

Asp Arg Glu Gly Glu Leu Val Gly Arg Ile Gly Met Gly Gly Asn Lys
    50                  55                  60

Ala Thr Val Cys Val Ser Leu Ser Gly Ala Gly Cys Lys Trp Val Lys
65                  70                  75                  80

Asp Trp Ala His Val Gln Arg Gln Ala Ser Ile Leu Arg Ala Arg Ile
            85                  90                  95
```

```
Ser Arg Val Asp Cys Ala His Asp Asp Tyr Glu Gly Glu Arg Leu Asp
            100                 105                 110

Val His Val Leu Arg Lys Arg Ala Ala Asp Gly Glu Phe Cys Gln Gly
        115                 120                 125

Gly Cys Pro Pro Arg His Arg Phe Leu Ser Asp Glu Gly His Gly Thr
130                 135                 140

Gly Ser Thr Leu Tyr Val Gly Ala Lys Gly His Lys Glu Leu Cys Ile
145                 150                 155                 160

Tyr Glu Lys Gly Lys Gln Met Gly Leu Lys Thr Ser Arg Trp Val Arg
                165                 170                 175

Ala Glu Val Arg Leu Tyr Gly Lys His Val Glu Ile Pro Leu Asp Val
            180                 185                 190

Leu Thr Asp Pro Gly Ala Tyr Leu Arg Gly Ser Tyr Asp Val Leu Arg
        195                 200                 205

Glu Leu Ile Thr Gly Ile Cys Thr Arg Leu Arg Thr Ile Arg Lys Gln
210                 215                 220

Val Asp Val Ser Val Glu Ala Gly Ile Glu Trp Ala His Arg Gln Val
225                 230                 235                 240

Gly Pro Phe Leu Asn Val Leu Arg Gly Ala Phe Gly His Ser Trp Ser
                245                 250                 255

Asp Val Cys Glu Ala Arg Ile Leu Arg Glu Gly His Pro Gly Arg Phe
            260                 265                 270

Arg Gly Ile Ser Lys Gly Glu Pro Leu His Arg Tyr Val Arg Glu Gln
        275                 280                 285

Leu Cys Gln Ser Ala Ala Ser
290                 295

<210> SEQ ID NO 49
<211> LENGTH: 57
<212> TYPE: PRT
<213> ORGANISM: Bacteriophage Cf2

<400> SEQUENCE: 49

Met Lys Glu Phe Ala Lys Cys Ile Gly Tyr Val Trp Ala Leu Ala Ala
1               5                   10                  15

Phe Ile Ser Leu Phe Ile Ile Gly Ala Tyr Tyr Leu Pro Glu Pro Trp
            20                  25                  30

Thr Trp Val Cys Gly Val Phe Leu Phe Leu Thr Pro Ala Gly Leu Ile
        35                  40                  45

Ala Tyr Phe Ser Gly Val Cys His Asp
50                  55

<210> SEQ ID NO 50
<211> LENGTH: 74
<212> TYPE: PRT
<213> ORGANISM: Bacteriophage Cf2

<400> SEQUENCE: 50

Met Asp Thr Asn Ala Leu Ala Leu Ile Gly Ala Ser Ala Leu Thr Val
1               5                   10                  15

Ile Val Gly Leu Ala Arg Phe Val Ala Trp Ile Leu Asp Arg Arg Ala
            20                  25                  30

Glu Ala Ala Leu Arg Ala His Arg Glu Gln Val Phe Ile Ile Glu Ser
        35                  40                  45

Tyr Val Asp Leu Val Ala Pro Thr Ile Ser Arg Arg Val Thr Ile Cys
50                  55                  60
```

Ser Ala Gln Ser Glu Met Glu Val Val Ala
65                  70

<210> SEQ ID NO 51
<211> LENGTH: 136
<212> TYPE: PRT
<213> ORGANISM: Bacteriophage Cf2

<400> SEQUENCE: 51

Met Asp Thr Leu Ser Lys Leu Leu Asp Lys Ala Arg Leu Met Cys Glu
1               5                   10                  15

Arg Asp Ser Asp Asn Cys Leu Ala Gln Thr Leu Gly Leu Gln Arg Ala
            20                  25                  30

Ala Val Ser Lys Trp Arg His Gly Gly Lys Ile Ser Pro Glu Glu Leu
        35                  40                  45

Ala Lys Leu Val Val Leu Ala Gln Ala Asp Pro Gly Ile Ala Val Leu
    50                  55                  60

Val Leu Asn Glu Gln Ala Asp Asp Ala Thr Ala Lys Lys Leu Trp Gly
65                  70                  75                  80

Pro Leu Trp Asp Arg Leu Ser Pro Val Thr Thr Val Ile Gly Ala Met
                85                  90                  95

Val Leu Ala Val Thr Leu Thr Pro Ala Thr Val Lys Ala Lys Ala Phe
            100                 105                 110

Glu Ile Asn Tyr Leu Asn Glu Ser Ser Ala Tyr Ser Leu Tyr Ile Met
        115                 120                 125

Ser Asn Ile Val Arg Ala Ser Leu
    130                 135

<210> SEQ ID NO 52
<211> LENGTH: 127
<212> TYPE: PRT
<213> ORGANISM: Bacteriophage Xf

<400> SEQUENCE: 52

Met Thr Phe Asp Thr Tyr Glu Arg Val Asp Leu Thr Gly Pro Trp Ala
1               5                   10                  15

Gly Phe Gly Phe Gln Gly His Arg Phe Phe Thr Pro Glu Asn Tyr Asp
            20                  25                  30

Ile Asp Pro Cys Gly Met Arg Tyr Trp Ala Leu Thr Cys Ala Ile Ala
        35                  40                  45

Arg Glu Trp Ser Leu Met Met Ser Glu Glu Arg Asn Ala Gln Ser Ala
    50                  55                  60

Asn Pro Arg Thr Pro Thr Ala Thr Arg Ser Pro Gly Ser Arg Ile Ser
65                  70                  75                  80

Glu Asp Ala Asn Val Ile Tyr Leu Arg Asp Val Leu Trp Arg Arg Arg
                85                  90                  95

Glu Lys Arg Leu Ser Val Gly Gly Asn Pro Gly Leu Ala Asp Ser Gly
            100                 105                 110

Lys Arg Ser Pro Thr Gly Arg Gly Arg Arg Pro Arg Arg Gly
        115                 120                 125

<210> SEQ ID NO 53
<211> LENGTH: 215
<212> TYPE: PRT
<213> ORGANISM: Bacteriophage Xf

<400> SEQUENCE: 53

Met Thr Ser Ser Gly Arg Glu Ala Leu Lys Trp Ile Ala Leu Val Leu
1               5                   10                  15

Met Thr Gly Asp His Val Ala Lys Val Leu Phe Gly Gly Tyr Val Pro
            20                  25                  30

Val Leu Ser Glu Leu Gly Arg Ile Ala Phe Pro Val Phe Ala Leu Val
        35                  40                  45

Met Ala Tyr Asn Leu Ala Gln Pro Arg Ala Asp Tyr Ala Lys Ser Val
    50                  55                  60

Leu Arg Leu Ala Gly Trp Gly Leu Leu Ala Gln Pro Phe His Ala Trp
65                  70                  75                  80

Ala Phe Gly Tyr Trp Leu Pro Leu Asn Val Leu Leu Thr Phe Ala Cys
                85                  90                  95

Ala Ala Leu Leu Val Trp Thr Val His Ala Arg His Trp Leu Tyr Ala
            100                 105                 110

Phe Val Phe Ala Val Val Val Pro Val Leu Val Asp Tyr Gln Trp Phe
        115                 120                 125

Gly Val Leu Leu Val Leu Ala Ala Trp Gly Leu Phe Arg Ser Gly Arg
    130                 135                 140

Leu Gln Trp Leu Val Gly Val Leu Ala Ser Met Ala Ala Leu Cys Trp
145                 150                 155                 160

Tyr Asn Gly Asn Val Trp Ala Leu Ala Ala Leu Pro Val Leu Ala Leu
                165                 170                 175

Gly Tyr Val Trp Trp Pro Leu Pro Arg Leu Arg Trp Ala Phe Tyr Gly
            180                 185                 190

Tyr Tyr Val Gly His Leu Gly Leu Leu Val Leu Ile Val Ser Leu Pro
        195                 200                 205

Ala Phe Arg Gln His Val Ala
    210                 215

<210> SEQ ID NO 54
<211> LENGTH: 395
<212> TYPE: PRT
<213> ORGANISM: Bacteriophage Xf

<400> SEQUENCE: 54

Met Pro Ile Glu Leu Tyr Thr Gly Gln Pro Gly Asn Gly Lys Thr Ala
1               5                   10                  15

Leu Met Met Glu Arg Leu Val Glu Ala Lys Arg Ala Glu Arg Pro
            20                  25                  30

Ile Phe Ala Ala Gly Ile Asp Gly Leu Gln Asp Gly Leu Ala Thr Val
        35                  40                  45

Leu Asp Asp Pro Arg Lys Trp Asn Asp Lys Ala Asp Asp Asn Tyr
    50                  55                  60

Val Val Pro Asn Gly Ser Leu Ile Phe Val Asp Glu Ala Trp Lys Trp
65                  70                  75                  80

Tyr Gly His Leu His Asp Ala Thr Arg Gln Gln Thr Pro Lys His Val
                85                  90                  95

Leu Asp Leu Ala Glu His Arg His Arg Gly Leu Asp Phe Val Trp Thr
            100                 105                 110

Thr Gln Gln Pro Asn Gln Leu Tyr Pro Phe Val Arg Gly Leu Ile Gly
        115                 120                 125

Ala His Thr His Val Val Arg Arg Phe Gly Thr Lys Met Ile Asp Val
    130                 135                 140

Phe Arg Trp Gly Glu Leu Asn Glu Glu Ile Lys Ser Ser Ala Lys Arg
145                 150                 155                 160

```
Asp Leu Ala Gln Arg Thr Thr Arg Leu Leu Pro Ser Ser Ile Phe Gly
                165                 170                 175

Ala Tyr Lys Ser Ala Glu Val His Thr Ile Lys Pro Arg Ile Pro Trp
            180                 185                 190

Lys Val Met Ala Leu Pro Gly Leu Val Ile Leu Ala Ile Ala Leu Gly
        195                 200                 205

Trp Leu Ala Tyr Thr Met Leu Lys Pro Ser Ala Met Ala Gly Gly Ala
    210                 215                 220

Lys Gly Thr Gln Ser Ala Ser Ala Asp Ala Ala Pro Gly Gly Ser Ala
225                 230                 235                 240

Thr Thr Ala Arg Arg Asp Gly Pro Arg Trp Glu Ser Pro Thr Glu Tyr
                245                 250                 255

Ala Lys Gln His Leu Pro Arg Phe Gly Thr Met Pro Trp Thr Ala Pro
            260                 265                 270

Val Phe Asp Asp Arg Ser Ile Thr Ala Asp Pro Met Leu Ile Cys Met
        275                 280                 285

Ser Ser Leu Ala Gly Ile Asp Ala Gln Gly Lys His Lys Glu Ala Ser
    290                 295                 300

Cys Thr Cys Met Thr Glu Gln Gly Thr Ala Tyr Asp Leu Asp Gln Pro
305                 310                 315                 320

Gln Cys Arg Thr Ile Ala Lys Arg Gly Pro Val Tyr Asn Pro Tyr Arg
                325                 330                 335

Gln Gln Arg Gln Asn Glu Gln Gln Pro Ala Gln Gln Gln Ala Ala
            340                 345                 350

Gln Gly Gly Ala Ala Pro Gly Phe Asn Gly Ile Ala Val Gln Arg
    355                 360                 365

Ser Thr Arg Thr Gln Gly Ser Phe Pro Glu Ser Lys Ala Tyr Ser Thr
    370                 375                 380

Lys Thr Thr Thr Pro Ser Thr Thr Leu Glu Met
385                 390                 395

<210> SEQ ID NO 55
<211> LENGTH: 109
<212> TYPE: PRT
<213> ORGANISM: Bacteriophage Xf

<400> SEQUENCE: 55

Met Pro Trp Leu Ile Ala Gln Leu Val Thr Ala Leu Ala Trp Leu Phe
1               5                   10                  15

Lys Ser Arg Ile Gly Leu Trp Ile Met Thr Ala Leu Val Trp Leu Gly
            20                  25                  30

Ile Asn Phe Gly Thr Ile Lys Met Val Val Glu Pro Ala Ile Asp Leu
        35                  40                  45

Leu Lys Asp Tyr Ala Gln Gly Met Gly Ser Gly Asn Gly Gln Leu Gly
    50                  55                  60

Ala Asp Ala Met Ala Trp Phe Gly Val Leu Gln Phe Asp Lys Ala Leu
65                  70                  75                  80

Thr Met Val Ile Ser Ala Val Ala Ala Lys His Ala Ile Met Gln Gly
                85                  90                  95

Arg Leu Phe Leu Phe Lys Arg Gly Phe Gly Ala Lys Pro
            100                 105

<210> SEQ ID NO 56
<211> LENGTH: 482
<212> TYPE: PRT
```

<213> ORGANISM: Bacteriophage Xf

<400> SEQUENCE: 56

| | | | | | | | | | | | | | | |
|---|---|---|---|---|---|---|---|---|---|---|---|---|---|---|
|Met|Ala|Gly|Gly|Leu|Arg|Asp|Cys|Leu|Arg|Gly|Phe|Arg|Ile|Met|Gly|
|1| | | |5| | | |10| | | |15| | |
|Trp|Leu|Ala|Arg|Val|Phe|Ala|Ser|Ala|Ile|Ala|Arg|Arg|Leu|Ala|Tyr|
| | | |20| | | |25| | | |30| | | | |
|Val|Leu|Val|Ala|Ala|Thr|Leu|Ala|Trp|Cys|Gly|Ile|Gly|Cys|Ala|Ser|
| | |35| | | |40| | | |45| | | | | |
|Ala|Gln|Asp|Phe|Gly|Thr|Gln|Gly|Ala|Ala|Tyr|Ser|Ala|Cys|Met|Ser|
| |50| | | |55| | | |60| | | | | | |
|Gln|Thr|Ala|Ala|Tyr|Leu|Ala|Ser|Leu|Gly|Arg|Gly|Ala|Asn|Asp|Arg|
|65| | | |70| | | |75| | | |80| | | |
|Asn|Pro|Glu|Cys|Asn|Val|Glu|Gln|Gly|Ser|Gln|Ala|Tyr|Arg|Gly|Gln|
| | | |85| | | |90| | | |95| | | | |
|Phe|Glu|Thr|Arg|Asp|Cys|Ser|Ser|Cys|Asp|Trp|Tyr|Arg|Ala|Tyr|Tyr|
| | |100| | | |105| | | |110| | | | | |
|Gly|Tyr|Phe|Pro|Trp|Ser|Lys|Gly|Cys|Asp|Gln|Glu|Pro|Asp|Tyr|Thr|
| |115| | | |120| | | |125| | | | | | |
|Gly|Ser|Gly|Pro|Trp|Gly|Thr|Tyr|Val|Gly|Thr|Ala|Arg|Asn|Gly|Ser|
|130| | | |135| | | |140| | | | | | | |
|Ile|Gly|Cys|Arg|Asn|Gly|Cys|Asp|Gly|Val|Trp|Phe|Gly|Asn|Gly|Asp|
|145| | | |150| | | |155| | | |160| | | |
|Asp|Thr|Met|Thr|Trp|Asn|Ala|Thr|Gly|Ala|Ile|Cys|Pro|Lys|Asp|Pro|
| | | |165| | | |170| | | |175| | | | |
|Glu|Lys|Thr|Cys|Asp|Ala|Met|Ser|Gly|Gly|Tyr|Gly|Trp|Asn|Gly|Tyr|
| | |180| | | |185| | | |190| | | | | |
|Leu|Gly|Val|Cys|Glu|Pro|Pro|Thr|Glu|Glu|Cys|Pro|Glu|Gly|Gln| |
| |195| | | |200| | | |205| | | | | | |
|Val|Pro|Asp|Gly|Lys|Gly|Gly|Cys|Ser|Ser|Lys|Cys|Pro|Glu|Gly| |
|210| | | |215| | | |220| | | | | | | |
|Met|Leu|Leu|Gln|Ala|Asp|Gly|Thr|Cys|Ala|Pro|Lys|Lys|Asn|Asp|Cys|
|225| | | |230| | | |235| | | |240| | | |
|Pro|Ala|Gly|Gln|Ile|Arg|Ser|Pro|Ser|Gly|Ser|Cys|Leu|Pro|Gly|Asp|
| | | |245| | | |250| | | |255| | | | |
|Gly|Gln|Cys|Ala|Ala|Gly|Glu|Val|Arg|Gly|Pro|Asp|Gly|Thr|Cys|Lys|
| | |260| | | |265| | | |270| | | | | |
|Lys|Asp|Gly|Asp|Gly|Asp|Gly|Glu|Pro|Asp|Glu|Pro|Gly|Glu|Gly|Asp|
| |275| | | |280| | | |285| | | | | | |
|Lys|Ser|Gln|Phe|Ser|Gly|Gly|Asp|Ser|Cys|Asp|Ser|Pro|Pro|Ser|Cys|
|290| | | |295| | | |300| | | | | | | |
|Ser|Gly|Asp|Ala|Ile|Met|Cys|Gly|Gln|Ala|Arg|Ile|Gln|Trp|Arg|Ile|
|305| | | |310| | | |315| | | |320| | | |
|Asp|Cys|Asn|Thr|Arg|Arg|Asp|Val|Asn|Ile|Thr|Gly|Gly|Ser|Cys|Ala|
| | | |325| | | |330| | | |335| | | | |
|Ser|Met|Pro|Val|Cys|Val|Gly|Glu|Asn|Cys|Lys|Ala|Leu|Glu|Tyr|Ser|
| | |340| | | |345| | | |350| | | | | |
|Gln|Leu|Leu|Met|Gln|Trp|Arg|Ala|Ala|Cys|Ala|Leu|Glu|Lys|Ala|Ala|
| |355| | | |360| | | |365| | | | | | |
|Asn|Asn|Ser|Gly|Gly|Thr|Gly|Asn|Asn|Ala|Asp|Val|Lys|Ala|Ile| |
|370| | | |375| | | |380| | | | | | | |
|Arg|Asp|Ala|Ile|Thr|Gly|Asn|Gly|Thr|Ala|Asp|Ile|Gly|Ala|Asp|Gly|
|385| | | |390| | | |395| | | |400| | | |

Lys Pro Ala Asp Ala Phe Ser Asp Glu Ser Gly Tyr Gly Glu His Gly
                405                 410                 415

Tyr Pro Thr Gly Glu Leu Asp Thr His Gly Phe Gly Tyr Ser Arg Thr
            420                 425                 430

Cys Pro Thr Ile Pro Asp Val Ala Val Phe Gly Gln Thr Leu His Phe
        435                 440                 445

Asp Thr Ser Lys Phe Cys Gln Trp Met Val Leu Gly Gln Ile Val
450                 455                 460

Leu Val Met Ala Ser Leu Val Ser Leu Arg Leu Met Ser Gln Gly Gly
465                 470                 475                 480

Ser Ala

<210> SEQ ID NO 57
<211> LENGTH: 76
<212> TYPE: PRT
<213> ORGANISM: Bacteriophage Xf

<400> SEQUENCE: 57

Met Arg Lys Leu Lys Thr Leu Phe Lys Asn Lys Thr Ala Ala Leu Ala
1               5                   10                  15

Ala Val Gly Ser Ala Ala Leu Val Ser Ala Pro Ala Phe Ala Ser Gly
            20                  25                  30

Gly Gly Gly Val Asp Val Gly Asp Val Val Ser Ala Ile Gln Gly Ala
        35                  40                  45

Ala Gly Pro Ile Ala Ser Ile Gly Gly Ala Val Leu Thr Val Leu Val
    50                  55                  60

Gly Ile Lys Val Tyr Lys Trp Val Arg Arg Ala Met
65                  70                  75

<210> SEQ ID NO 58
<211> LENGTH: 98
<212> TYPE: PRT
<213> ORGANISM: Bacteriophage Xf

<400> SEQUENCE: 58

Met Lys Val Gln Val Met Ser Ser Ala Val Ala Val Arg Ser Phe Pro
1               5                   10                  15

Ala Arg Glu Gly Lys Pro Ala Thr His Phe Arg Glu Gln Thr Ala Ala
            20                  25                  30

Val Leu Arg Asp Gly Asp Phe Pro Leu Pro Phe Ile Ile Gly Leu Asp
        35                  40                  45

Glu Asp Gln Ala Pro Tyr Gly Glu Gly Phe Tyr Ile Ile Asp Pro Lys
    50                  55                  60

Ser Leu Gln Asn Asn Lys Phe Gly Gly Leu Glu Phe Gly Arg Arg Ile
65                  70                  75                  80

Arg Leu Ile Pro Asp Ala Thr Ala Lys Ala Val Gln Pro Ala Ala Arg
                85                  90                  95

Val Ala

<210> SEQ ID NO 59
<211> LENGTH: 346
<212> TYPE: PRT
<213> ORGANISM: Bacteriophage Xf

<400> SEQUENCE: 59

Met Ser Asp Gly Thr Cys Ser Phe Cys Gly Asp Pro Thr Ala Tyr Phe
1               5                   10                  15

Phe Pro Gly Gly Leu Cys Val Ala Cys Thr Ser Lys Asn Ala Arg Ile
            20                  25                  30

Arg Met Gln Glu Gln Pro Thr Gln Ser Arg Glu Leu Ser Ala Phe Asp
        35                  40                  45

Ala Ser Val Gly Val Met Gln Ala Ala Thr Arg Arg Thr Glu Ile Ala
    50                  55                  60

Ala Glu Asn Ile Gln Lys Asn Lys Arg Val Val Gly Thr Ser Val Arg
65                  70                  75                  80

Glu Phe Asp Ala Ala His Pro Val Ala Leu Thr Ala Glu Gly Gln Arg
                85                  90                  95

Ala Ala Leu Ala Leu Gly Leu Val His Tyr Lys Thr Ser Asp Thr Arg
            100                 105                 110

Ala Ser Ala Thr Gly Thr Val Thr Ile Glu Ile Asp Pro Leu Lys Ala
        115                 120                 125

Arg Ala Gln Arg Leu Arg Lys Ser Val Ile Thr Gly Ala Arg Leu His
    130                 135                 140

Asp Gln Glu Ala Lys Lys Gly Ser Phe Arg Gly Ala Trp Tyr Phe Leu
145                 150                 155                 160

Thr Leu Thr Tyr Arg Asp Gly Ser Asp Ser Ser Pro Gly Asp Val Ser
                165                 170                 175

Glu Leu Phe Lys Arg Met Arg Gly His Phe Asn Arg Leu Lys Ser Gly
            180                 185                 190

Arg Ala Arg Trp Asn Arg Glu Ser Phe Arg Tyr Val Trp Val Gly Glu
        195                 200                 205

Leu Thr Gln Arg Phe Arg Pro His Tyr His Val Met Leu Trp Val Pro
    210                 215                 220

Thr Gly Met Tyr Phe Gly Lys Val Asp Gln Arg Gly Trp Trp Pro His
225                 230                 235                 240

Gly Thr Thr Gln Ile Glu Lys Ala Arg Asn Cys Val Gly Tyr Leu Ala
                245                 250                 255

Lys Tyr Ala Ser Lys Phe Thr Ala Leu Thr Ala Gly Ala Phe Pro Lys
            260                 265                 270

Gly Phe Arg Thr His Gly Ile Gly Gly Leu Asp Thr Glu Ser Lys Arg
        275                 280                 285

Glu Leu Arg Trp Trp Lys Ala Pro Lys Asp Ala Arg Glu Ala Leu Gly
    290                 295                 300

Gly Glu Ala Asp Ile Arg Lys Ala Lys Gly Gly Trp Phe Asp Arg Leu
305                 310                 315                 320

Thr Gly Glu Phe Trp Pro Ser Pro Trp Lys Val Thr Phe Ile Phe Gly
                325                 330                 335

Arg Thr Phe Ala Trp Lys Val Val Gln Leu
            340                 345

<210> SEQ ID NO 60
<211> LENGTH: 70
<212> TYPE: PRT
<213> ORGANISM: Bacteriophage Xf

<400> SEQUENCE: 60

Met Ala Leu Ser Thr Asp Thr Asn Ala Leu Ala Leu Ile Gly Ala Ser
1               5                   10                  15

Ala Leu Thr Val Ile Val Gly Leu Ala Arg Leu Val Ala Trp Ile Leu
            20                  25                  30

Asp Arg Arg Ala Glu Ala Ala Leu Arg Ala His Arg Glu Gln Val Phe
        35                  40                  45

```
Ile Ile Glu Ser Tyr Val Ser Leu Val Ala Pro Thr Val Ser Arg Arg
 50                  55                  60

Val Thr Ile Cys Ser Ala
 65                  70

<210> SEQ ID NO 61
<211> LENGTH: 61
<212> TYPE: PRT
<213> ORGANISM: Bacteriophage Xf

<400> SEQUENCE: 61

Met Gly Phe Gln Val Gln Tyr Arg Asp Gly Arg Arg Trp Val Val Leu
 1               5                  10                  15

Ala Ser His Pro Thr Arg Asn Ala Ala Arg Asp Ala Ala Ala Arg
                20                  25                  30

Ile Ala Phe Leu Val Ala Asp Gly Phe Lys Tyr Gly Asp Val Val Arg
                35                  40                  45

Asp Phe Arg Val Arg Gly Val Thr Val Ala Glu Ala Ala
 50                  55                  60

<210> SEQ ID NO 62
<211> LENGTH: 223
<212> TYPE: PRT
<213> ORGANISM: Bacteriophage Xf

<400> SEQUENCE: 62

Met Tyr Ser Ser Thr Lys Gln Glu Cys Lys Gly Gln Leu Asn Met Ser
 1               5                  10                  15

Ala Glu Asn Glu Leu Ile Asp Leu Val Arg Ala Gly Gly Lys Phe Ser
                20                  25                  30

Ser Asp Asn Ala Leu Ala Gln Lys Leu Gly Val Thr Arg Ala Met Val
                35                  40                  45

Ser Ser Trp Arg Ser Gly Arg Tyr Ala Met Pro Asp Asp Gln Ile Ala
                50                  55                  60

Gln Leu Cys Ala Leu Ala Lys Leu Asp Gly Ala Ser Trp Met Ala Arg
 65                  70                  75                  80

Ile His Thr Glu Arg Ala Gly Ser Ala Thr Glu Arg Ala Leu Trp Lys
                85                  90                  95

Ser Ile Leu Asp Arg Leu Ala Pro Ile Thr Ala Val Val Gly Ala Leu
                100                 105                 110

Ala Ile Val Ala Val Gly Leu His Ala Gly Ala His Glu Gly Leu Leu
                115                 120                 125

Thr Ala Leu Ser Pro Leu Ala Ile Thr Pro Thr Val Tyr Thr Leu Cys
                130                 135                 140

Glu Met Arg Asn Arg Thr Val Asp Ala Ala Leu His Arg Arg Gly Leu
145                 150                 155                 160

Leu Leu Gln Pro Thr Pro Gln Glu Ala Asp Trp Thr Met Thr Phe Asp
                165                 170                 175

Thr Tyr Glu Arg Val Asp Leu Thr Gly Pro Trp Ala Gly Asp Cys Arg
                180                 185                 190

Ala Gly Asn Ala Pro Val Pro Ala Gly Ile His Pro Ile Cys Arg Gly
                195                 200                 205

His Thr Pro His Ile Ser Arg Ser Leu Asp Lys Ser Pro Gln Leu
                210                 215                 220

<210> SEQ ID NO 63
```

```
<211> LENGTH: 15
<212> TYPE: DNA
<213> ORGANISM: lysogenic filamentous bacteriophage

<400> SEQUENCE: 63
tatacattat gcgaa                                                      15

<210> SEQ ID NO 64
<211> LENGTH: 13
<212> TYPE: DNA
<213> ORGANISM: Bacteriophage Cf2

<400> SEQUENCE: 64
taattatgtc aaa                                                        13

<210> SEQ ID NO 65
<211> LENGTH: 500
<212> TYPE: DNA
<213> ORGANISM: Bacteriophage Cf16

<400> SEQUENCE: 65
tgacgacgaa ttgcagagct atgcgctatg gcacatctgg atggcggcga atggatggcg      60
aaaattcagg ccgaagcagc ggcatcgccg gctgaaaaag cgctatggcg atcagtgttg     120
gacaggctaa gcgcggccgc cgcggtggtc gcgctgctgg tcctggcggt acacacaggg     180
gcgcatgagc cggtgctagc ggccctctcg ccggtagccc ttaccacccc tctatacatt     240
atgcgaagtg tgctgttgac gctgctgtgc gccctggcgg cctatcactg ctgctccctc     300
cacaggaagc ggactggaca atgacgctag acacgtacga tcgcgtagac ctgacggccc     360
ttgggccggt tttggttttc accggcaccg cttcttcacc ccggagaatt acgacatcga     420
accgtgcgat atgcggtatt cggcgctgac atgcgcgatc gcacgcgaat ggtcactgtt     480
gatgtcagaa gaacgcaatg                                                 500

<210> SEQ ID NO 66
<211> LENGTH: 250
<212> TYPE: DNA
<213> ORGANISM: Xanthomonas citri

<400> SEQUENCE: 66
catgcaagct tactcaacgg cgcccccgtc cgcgtggact cgggctcggt attgaccatc      60
gctggctgag gcgggcggcg cggtgcagcc gcaagtgaaa tcaaagagaa gcacgaacaa     120
tatttgacat aatatacatt atgcgaaatt ggccgcgtcc ccgtacgggc cggcgccatg     180
tgcactgcag ctcgagcacc aggcagaaca gttccgcacc gccaggctga tgcagtccct     240
gacgtcaggc                                                            250

<210> SEQ ID NO 67
<211> LENGTH: 1220
<212> TYPE: DNA
<213> ORGANISM: Bacteriophage Cf-tv2

<400> SEQUENCE: 67
gccacgatag aactccatgg cccatggcag cgttacgtgc atcagcagca tcggtgcgcg      60
atgcaaaata gctctgttca acagcgttgc cgttgacgac gatggtcaag acgtaaatgc     120
gggggccgcc ctgcactcga gctggcgcaa tcatccatgc aacagatcga gactcagcca     180
cgacgcacct cgagatagcg accaatgagg cttgatcaat ttgagcaacc atcgcgtcgt     240
gcttgagatc aagacaccaa cagatcacag cgacgattgc gtaccggtg agcacgcaga     300
```

```
tcgacacgag aatgtgcagc gccaaaagct ggcccaggac cgaatatgga tgcacggtgt    360
agcccctcc cctgcccctt gacgcggacc ccggagggga gccggggtg cgcggtgctt     420
agggttgcct aagcacggga gcatgtatag ttttcactgt cctctctgtc aagaaaaacc   480
tgtcatggac catgtaaata atttgcttga caccgtgcgc aagtcgtgcg ccataccgtc   540
agacaacatg ttgagcaaaa aaattggagt gacgcgggcg ctgataagcg gctggcgcgt   600
tggccggtac ccgtggcctg acgcacgaat tgcagagcta tgcgctatgc cacatctgga   660
tggcggcgaa tggatggcga aaattcacgc cgaagcagcg gcatcgccgg ctgaaaaagc   720
gctatggcga tcagtgttgg acaggctaag gcggccgcc gcgtggtcg cgctgctggt    780
cctggcggta cacacagggg cgcatgaggc gctgctagcg gccctctcgc cggtagccgt   840
tacccaccct ctatacatta tgcgaactgt gctgttgacg ctgctgtgcg ccctggcggc   900
ctatcactgc tggtccctcc acaggaagcg cactggacaa tgacgctaga cacctacgat   960
cgcgtagacc tgaccggccc ttgggccggt tttggttttc aggggcaccg gttcttcacc   1020
ccggagaatt acgacatcga accgtgcgat atgcggtatt gggcgctgac atgcgcgatc   1080
gcacgggaat ggtcactgtt gatgtcagaa gaacgcaatg cgcgatcggc gaatcctcga   1140
aagcctactg ccacaagatc tccagggtct cgtttgtctc gaggcgcaga cgtgatctat   1200
ctgcgggacg tgctgctgca                                               1220
```

<210> SEQ ID NO 68
<211> LENGTH: 166
<212> TYPE: PRT
<213> ORGANISM: Bacteriophage Cf-tv2

<400> SEQUENCE: 68

```
Met Tyr Ser Phe His Cys Pro Leu Cys Gln Glu Lys Pro Val Met Asp
1               5                   10                  15

His Val Asn Asn Leu Leu Asp Thr Val Arg Lys Ser Cys Ala Ile Pro
            20                  25                  30

Ser Asp Asn Met Leu Ser Lys Lys Ile Gly Val Thr Arg Ala Leu Ile
        35                  40                  45

Ser Gly Trp Arg Val Gly Arg Tyr Pro Val Pro Asp Ala Arg Thr Ala
    50                  55                  60

Glu Leu Tyr Ala Met Ala Met Leu Asp Gly Gly Glu Trp Met Ala Lys
65                  70                  75                  80

Ile Met Ala Glu Ala Ala Ala Ser Pro Ala Glu Lys Ala Leu Trp Arg
                85                  90                  95

Ser Val Leu Asp Arg Leu Ser Ala Ala Ala Val Ala Leu Leu
            100                 105                 110

Val Leu Ala Val Arg Thr Gly Ala Glu Glu Ala Leu Ala Ala Leu
            115                 120                 125

Ser Pro Val Ala Val Thr His Pro Leu Tyr Thr Met Arg Ser Val Leu
        130                 135                 140

Leu Thr Leu Leu Cys Ala Leu Ala Ala Tyr Arg Cys Trp Ser Leu His
145                 150                 155                 160

Arg Lys Arg Thr Gly Gln
                165
```

<210> SEQ ID NO 69
<211> LENGTH: 27
<212> TYPE: DNA
<213> ORGANISM: Artificial Sequence

```
<220> FEATURE:
<223> OTHER INFORMATION: synthetic necleic acid sequence of a primer

<400> SEQUENCE: 69
caggatcgaa tatggatgca cggtgta                                              27

<210> SEQ ID NO 70
<211> LENGTH: 27
<212> TYPE: DNA
<213> ORGANISM: Artificial Sequence
<220> FEATURE:
<223> OTHER INFORMATION: Synthetic neclei acid sequence of a primer

<400> SEQUENCE: 70
tgacagagag gacagtgaaa actatac                                              27

<210> SEQ ID NO 71
<211> LENGTH: 143
<212> TYPE: DNA
<213> ORGANISM: Bacteriophage Cf

<400> SEQUENCE: 71
gtaccaggta ctgtccaaaa agaactgtct ctcctgtcac ttttgatatg tacgagggca          60
cgaatccgtt gggattcgtg gcgcgtgggg gccgagggag gccccaggcg cagttccccg         120 tccctcccc cgatgtggca cgt                                                 143

<210> SEQ ID NO 72
<211> LENGTH: 145
<212> TYPE: DNA
<213> ORGANISM: Bacteriophage Cf

<400> SEQUENCE: 72
catggtccat gacaggtttt tcttgacaga gaggacagtg aaaactatac atgctcccgt          60
gcttaggcaa ccctaagcac cgcgacaccc ccggctcccc tccggggtcc gcgtcaaggg         120
gcaggggagg gggctacacc gtgca                                              145

<210> SEQ ID NO 73
<211> LENGTH: 209
<212> TYPE: PRT
<213> ORGANISM: Bacteriophage Cf2

<400> SEQUENCE: 73
```

| Val | Ile | Leu | Ser | Ala | Leu | Cys | Thr | Leu | Val | Ile | Ala | Leu | Cys | Ala | Ile |
|---|---|---|---|---|---|---|---|---|---|---|---|---|---|---|---|
| 1 | | | | 5 | | | | | 10 | | | | | 15 | |

| Ser | Pro | Ala | His | Ala | Ala | Asp | Ser | Phe | Ser | Gln | Ala | Phe | Ala | Lys | Cys |
| | | | 20 | | | | | 25 | | | | | 30 | | |

| Met | Asn | Asp | Ala | Ser | Ala | Tyr | Gln | Val | Lys | Asp | Thr | Asn | Leu | Ile | Thr |
| | | 35 | | | | | 40 | | | | | 45 | | | |

| Ser | Pro | Gly | Thr | Cys | Val | Asp | Lys | Val | Thr | Glu | Ala | Thr | Gly | Lys | Tyr |
| 50 | | | | | 55 | | | | | 60 | | | | | |

| Tyr | Gln | Cys | Gln | Tyr | Ser | Ala | Ala | Ala | Tyr | Tyr | Gln | Gly | Pro | Val | Ser |
| 65 | | | | | 70 | | | | | 75 | | | | | 80 |

| Val | Val | Thr | Cys | Gly | Asp | Tyr | Pro | Tyr | Asp | Asn | Glu | Asn | Asn | Cys | Lys |
| | | | | 85 | | | | | 90 | | | | | 95 | |

| Asn | Ala | Pro | Pro | Leu | Thr | Asn | Val | Ser | Val | Arg | Gly | Ser | Ile | Tyr | Ala |
| | | | 100 | | | | | 105 | | | | | 110 | | |

| Cys | Ser | Trp | Gln | Cys | Gln | Tyr | Thr | Met | Asn | Ser | Ala | Gly | Gly | Val | Asp |
| | | | 115 | | | | | 120 | | | | | 125 | | |

```
Val Cys Met Gly Gly Ala Asp Leu Tyr Cys Ala Ala Lys Asn Trp
    130                 135                 140

Ser Pro Thr Gly Gln Glu Cys Gln Gln Gly Asp Ala Val Pro Ser Gly
145                 150                 155                 160

Ile His Glu Pro Asp Lys Gln Thr Cys Ser Ser Thr Gly Gly Ala Tyr
                165                 170                 175

Ala Glu Cys Thr Arg Glu Asp Gly Thr His Cys Val Thr Gly Ala Ala
            180                 185                 190

Gly Ser Thr Leu Cys Trp Lys Pro Glu Leu Thr Gly Pro Arg Gln Thr
        195                 200                 205

Ala

<210> SEQ ID NO 74
<211> LENGTH: 211
<212> TYPE: PRT
<213> ORGANISM: Bacteriophage Cf1c

<400> SEQUENCE: 74

Val Val Val Ala Ala Cys Phe Gly Leu Leu Gln Leu Cys Ser Gly
1               5                   10                  15

Ser Ala His Ala Ala Val Asp Gln Gly Glu Ala Tyr Ser Leu Cys Met
                20                  25                  30

Lys Phe Ala Ser Asp Met Val Ala Lys Asn Pro Asp Met Arg Arg Met
            35                  40                  45

Pro Ser Cys Arg Ser Arg Ala Phe Gln Tyr Thr Cys Gln Tyr Glu
    50                  55                  60

Ala Ile Pro Tyr Val Gly Lys Ser Gln Trp Ser Val Asp Thr Cys Gly
65                  70                  75                  80

Asp Tyr Ser Tyr Asp Asp Gln Tyr Thr Cys Ala Ser Arg Asn Ser Asn
                85                  90                  95

Lys Leu Ala Asp Ala Ala Pro Trp Tyr Thr Pro Pro Asn Cys Ile
            100                 105                 110

Ser Gly Cys Gln Val Gln Gly Thr Ser Phe Ser Gly Asp Asn Gly Gly
        115                 120                 125

Val Lys Thr Tyr Gly Met Lys Asp Arg Thr Tyr Asn Gly Ser Ile Cys
    130                 135                 140

Thr Pro Thr Lys Pro Thr Asn Asp Ile Gly Glu Leu Gln Glu Lys
145                 150                 155                 160

Asn Asp Ala Thr Lys Glu Lys Ala Pro Glu Cys Thr Ala Leu Gly Ser
                165                 170                 175

Gly Gln Thr Ala Cys Leu Lys Pro Asn Gly Asp Tyr Cys Ala Thr Ala
            180                 185                 190

Ser Ser Gly Lys Thr Phe Cys Trp Lys Pro Ala Glu Thr Gly Lys Lys
        195                 200                 205

Thr Asp Ala
    210

<210> SEQ ID NO 75
<211> LENGTH: 80
<212> TYPE: PRT
<213> ORGANISM: Bacteriophage Cf2

<400> SEQUENCE: 75

Ser Pro Thr Gly Asp Leu Tyr Thr Lys Ser Asp Lys Thr Val Glu Ser
1               5                   10                  15

Val Val Ser Arg Phe Ala Thr Gln Val Arg Ala Thr Pro Leu Ala Gly
```

```
                20                  25                  30
Gly Ile Ala Ser Phe Met Thr Val Pro Ser Gly Gly Ser Cys Phe Val
            35                  40                  45

Phe Ser Leu Gly Ala Ser Lys Trp Trp Asp Ala Met Met Ile Asp Phe
        50                  55                  60

His Cys Ser Gly Thr Phe Leu Thr Phe Leu Arg Ala Cys Gly Trp Val
65                  70                  75                  80
```

<210> SEQ ID NO 76
<211> LENGTH: 80
<212> TYPE: PRT
<213> ORGANISM: Bacteriophage phiLf

<400> SEQUENCE: 76

```
Ala Pro Met Ser Glu Leu Tyr Lys Lys Ser Gly Lys Thr Val Glu Ser
1               5                   10                  15

Val Leu Ser Lys Phe Asn Thr Gln Val Arg Gly Thr Pro Met Val Ala
            20                  25                  30

Gly Ile Gly Asp Phe Met Lys Val Pro Ser Gly Gly Ser Cys Pro Val
            35                  40                  45

Phe Ser Leu Gly Ala Ser Lys Trp Trp Asp Ala Met Thr Ile Asn Phe
        50                  55                  60

His Cys Gly Gly Asp Phe Leu Ala Phe Leu Arg Ala Ala Gly Trp Val
65                  70                  75                  80
```

<210> SEQ ID NO 77
<211> LENGTH: 36
<212> TYPE: DNA
<213> ORGANISM: Bacteriophage Cf1c

<400> SEQUENCE: 77
gtagccgtta cccaccctct atacattatg cgaagt                                 36

<210> SEQ ID NO 78
<211> LENGTH: 36
<212> TYPE: DNA
<213> ORGANISM: Bacteriophage XacF1

<400> SEQUENCE: 78
gtagccgtta cccaccctct atacattatg cgaagt                                 36

<210> SEQ ID NO 79
<211> LENGTH: 36
<212> TYPE: DNA
<213> ORGANISM: Bacteriophage Cf2

<400> SEQUENCE: 79
gagtcgagtg cgtatagtct gtatattatg tcaaat                                 36

<210> SEQ ID NO 80
<211> LENGTH: 36
<212> TYPE: DNA
<213> ORGANISM: Bacteriophage phiLf

<400> SEQUENCE: 80
ctcgccctaa cggcaccttc tatacattat gcgaaa                                 36

<210> SEQ ID NO 81
<211> LENGTH: 36
<212> TYPE: DNA
<213> ORGANISM: Bacteriophage Xf

<400> SEQUENCE: 81
ctcgccataa cgccaaccgt ctatacatta tgcgaa    36

<210> SEQ ID NO 82
<211> LENGTH: 12
<212> TYPE: PRT
<213> ORGANISM: Bacteriophage Cf1c

<400> SEQUENCE: 82

Val Ala Val Thr His Pro Leu Tyr Ile Met Arg Ser
1               5                   10

<210> SEQ ID NO 83
<211> LENGTH: 12
<212> TYPE: PRT
<213> ORGANISM: Bacteriophage XacF1

<400> SEQUENCE: 83

Val Ala Val Thr His Pro Leu Tyr Ile Met Arg Ser
1               5                   10

<210> SEQ ID NO 84
<211> LENGTH: 12
<212> TYPE: PRT
<213> ORGANISM: Bacteriophage Cf2

<400> SEQUENCE: 84

Glu Ser Ser Ala Tyr Ser Leu Tyr Ile Met Ser Asn
1               5                   10

<210> SEQ ID NO 85
<211> LENGTH: 12
<212> TYPE: PRT
<213> ORGANISM: Bacteriophage phiLf

<400> SEQUENCE: 85

Leu Ala Leu Thr Ala Pro Ser Ile His Tyr Ala Lys
1               5                   10

<210> SEQ ID NO 86
<211> LENGTH: 12
<212> TYPE: PRT
<213> ORGANISM: Bacteriophage Xf

<400> SEQUENCE: 86

Leu Ala Ile Thr Pro Thr Val Tyr Thr Leu Cys Glu
1               5                   10

<210> SEQ ID NO 87
<211> LENGTH: 132
<212> TYPE: DNA
<213> ORGANISM: Bacteriophage Cf1c

<400> SEQUENCE: 87 agcccctcc cctgcccttg acgcggaccc cggaggggag ccgggggtgc gcggtgctta    60
gggttgccta agcacgggag catgtatagt tttcactgtc ctctctgtca agaaaaacct   120
gtcatggacc at                                                      132

<210> SEQ ID NO 88
<211> LENGTH: 133
<212> TYPE: DNA
<213> ORGANISM: Bacteriophage XacF1

-continued

<400> SEQUENCE: 88

```
agccccctcc cctgcccctt gacgcggacc ccggagggga gccgggggtg cgcggtactt     60
agggttgcct aagcacggga gcatatatag ttttcactgt cctctctgtc aagaaaaacc    120
cgtcatggac cat                                                       133
```

<210> SEQ ID NO 89
<211> LENGTH: 134
<212> TYPE: DNA
<213> ORGANISM: Bacteriophage Cf2

<400> SEQUENCE: 89

```
agcccctatc ccctgcccct tgacgcggac cccggagggg agccgggggt gcgcggtgta     60
tcgcgtccgg atacacgggg agcatgtaaa ctcgttggag acagtgctgt caaccggcga    120
gatacatgga caca                                                      134
```

UNITED STATES PATENT AND TRADEMARK OFFICE
CERTIFICATE OF CORRECTION

PATENT NO. : 10,626,375 B2
APPLICATION NO. : 15/321942
DATED : April 21, 2020
INVENTOR(S) : Ting-Yu Yeh It is certified that error appears in the above-identified patent and that said Letters Patent is hereby corrected as shown below:

On the Title Page
Item (86), PCT No.: delete "PCT/US2015/374880" and insert -- PCT/US2015/037488 --.

Signed and Sealed this
Tenth Day of May, 2022

Katherine Kelly Vidal
*Director of the United States Patent and Trademark Office*